(12) United States Patent
Gruber

(10) Patent No.: US 10,889,634 B2
(45) Date of Patent: Jan. 12, 2021

(54) ANTI-AGE ANTIBODIES AND METHODS OF USE THEREOF

(71) Applicant: Siwa Corporation, Chicago, IL (US)

(72) Inventor: Lewis S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 35 days.

(21) Appl. No.: 15/768,425

(22) PCT Filed: May 27, 2016

(86) PCT No.: PCT/US2016/034880
§ 371 (c)(1),
(2) Date: Apr. 13, 2018

(87) PCT Pub. No.: WO2017/065837
PCT Pub. Date: Apr. 20, 2017

(65) Prior Publication Data
US 2018/0312577 A1  Nov. 1, 2018

Related U.S. Application Data

(63) Continuation-in-part of application No. 14/974,561, filed on Dec. 18, 2015, now Pat. No. 10,358,502.

(60) Provisional application No. 62/241,007, filed on Oct. 13, 2015.

(51) Int. Cl.
| | |
|---|---|
| *C07K 16/18* | (2006.01) |
| *C07K 16/46* | (2006.01) |
| *A61K 47/68* | (2017.01) |
| *A61P 21/00* | (2006.01) |
| *A61K 39/00* | (2006.01) |

(52) U.S. Cl.
CPC .......... *C07K 16/18* (2013.01); *A61K 47/6803* (2017.08); *A61P 21/00* (2018.01); *C07K 16/468* (2013.01); *A61K 47/6843* (2017.08); *A61K 2039/505* (2013.01); *C07K 2317/24* (2013.01); *C07K 2317/30* (2013.01); *C07K 2317/31* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,470,521 B2 | 12/2008 | O'Keefe | |
| 2004/0142391 A1 | 7/2004 | Schmidt | |
| 2010/0249038 A1 | 9/2010 | Logsdon | |
| 2017/0240632 A1 | 8/2017 | Thomas | |
| 2020/0231706 A1 | 7/2020 | Gruber | |

FOREIGN PATENT DOCUMENTS

| | | |
|---|---|---|
| AU | 2009248945 | 11/2012 |
| AU | 2009248945 | 4/2013 |
| AU | 2009248945 | 2/2014 |
| AU | 2011332143 | 6/2015 |
| AU | 2014202548 | 6/2015 |
| AU | 2011332143 | 1/2016 |
| AU | 2014202548 | 1/2016 |
| AU | 2014202548 | 4/2016 |
| AU | 2014202548 | 6/2016 |
| AU | 2016204196 | 8/2016 |
| CA | 2724886 | 6/2014 |
| CA | 2724886 | 2/2015 |
| CA | 2724886 | 9/2015 |
| CA | 2724886 | 4/2016 |
| CA | 2818647 | 10/2016 |
| CA | 2724886 | 2/2017 |
| CA | 2818647 | 4/2017 |
| CA | 2724886 | 5/2017 |
| CA | 2818647 | 10/2017 |
| CA | 2818647 | 11/2017 |
| CA | 2818647 | 6/2018 |
| CA | 2818647 | 7/2018 |
| CN | 200980118817.6 | 5/2012 |
| CN | 200980118817.6 | 2/2013 |
| CN | 200980118817.6 | 10/2013 |
| CN | 200980118817.6 | 5/2014 |

(Continued)

OTHER PUBLICATIONS

Ward et al. (Nature 341:544-546 (1989)) (Year: 1989).*
Smith-Gill et al. (J. Immunol. 139:4135-4144 (1987)) (Year: 1987).*
Song et al. (Biochem Biophys Res Comm 268:390-394 (2000)) (Year: 2000).*
Padlan et al. (PNAS 1989, 86:5938-5942) (Year: 1989).*
Lamminmaki et al. (JBC 2001,276:36687-36694) (Year: 2001).*
U.S. Appl. No. 12/994,421, filed Jun. 14, 2012.
U.S. Appl. No. 12/951,768, filed Jul. 2, 2012.
U.S. Appl. No. 12/951,768, filed Mar. 30, 2012.
U.S. Appl. No. 12/994,421, filed Jul. 20, 2012.

(Continued)

*Primary Examiner* — Daniel C Gamett
(74) *Attorney, Agent, or Firm* — Evan Law Group LLC

(57) ABSTRACT

An anti-AGE antibody comprises a protein or peptide that comprises at least one amino acid sequence having at least 90% sequence identity, preferably at least 95% sequence identity, more preferably at least 98% sequence identity, with specific amino acid sequences. The anti-AGE antibody binds to a protein or peptide that exhibits a carboxymethyllysine modification. The anti-AGE antibody may be used for killing senescent cells, killing partially-functional or non-functional cells, treating sarcopenia, promoting tissue or organ regeneration, promoting regenerative processes or overcoming aging effects, treating atherosclerosis, preventing or delaying the onset of cataracts, preventing or delaying the onset of loss of adipose tissue, increasing health span, preventing or delaying the onset of lordokyphosis, treating inflammation or autoimmune disorders, treating neurodegenerative disorders or treating cancer.

26 Claims, 1 Drawing Sheet
Specification includes a Sequence Listing.

(56) References Cited

FOREIGN PATENT DOCUMENTS

| | | |
|---|---|---|
| CN | 200980118817.6 | 10/2014 |
| CN | 200980118817.6 | 3/2015 |
| CN | 201510303227.8 | 6/2016 |
| CN | 201510303227.8 | 12/2016 |
| CN | 201510303227.8 | 5/2017 |
| CN | 201580056616.3 | 4/2020 |
| EP | 09 751 639.7 | 11/2011 |
| EP | 09 751 639.7 | 6/2012 |
| EP | 09 751 639.7 | 1/2013 |
| EP | 09751639.7 | 7/2013 |
| EP | 09751639.7 | 1/2014 |
| EP | 14170802.4 | 9/2014 |
| EP | 14170802.4 | 7/2015 |
| EP | 14170802.4 | 12/2015 |
| EP | 14170802.4 | 4/2016 |
| EP | 14170802.4 | 11/2016 |
| EP | 16198527.0 | 2/2017 |
| EP | 11776932.3 | 3/2017 |
| EP | 11776932.3 | 8/2017 |
| EP | 11776932.3 | 9/2017 |
| EP | 11776932.3 | 1/2018 |
| EP | 11776932.3 | 2/2018 |
| EP | 11776932.3 | 3/2018 |
| EP | 15772116.8 | 9/2018 |
| EP | 15772116.8 | 1/2019 |
| EP | 17708098.3 | 1/2019 |
| EP | 18184822.7 | 1/2019 |
| EP | 11776932.3 | 2/2019 |
| EP | 15772116.8 | 2/2019 |
| EP | 17708098.3 | 2/2019 |
| EP | 18184822.7 | 6/2019 |
| EP | 17708098.3 | 7/2019 |
| EP | 17737078.0 | 8/2019 |
| EP | 18726656.4 | 12/2019 |
| EP | 15772116.8 | 3/2020 |
| EP | 17737078.0 | 6/2020 |
| EP | 15772116.8 | 7/2020 |
| EP | 19210193.9 | 7/2020 |
| IL | 209513 | 8/2012 |
| IL | 209513 | 5/2013 |
| IL | 209513 | 5/2014 |
| IL | 209513 | 12/2014 |
| IL | 240242 | 4/2016 |
| IL | 240242 | 1/2017 |
| IL | 248652 | 5/2017 |
| IL | 251210 | 6/2020 |
| IN | 4875/KOLNP/2010 | 12/2016 |
| IN | 201737009367 | 6/2020 |
| JP | 2011-511734 | 11/2013 |
| JP | 2011-511734 | 12/2014 |
| JP | 2015-076575 | 6/2015 |
| JP | 2015-076575 | 1/2016 |
| JP | 2016-098558 | 7/2016 |
| JP | 2016-098558 | 12/2016 |
| JP | 2017-086871 | 4/2018 |
| JP | 2017086871 | 3/2019 |
| JP | 2017-515740 | 7/2019 |
| JP | 2017-515740 | 1/2020 |
| JP | 2018-543120 | 3/2020 |
| JP | 2018-566505 | 6/2020 |
| JP | 2020-106264 | 8/2020 |
| KR | 10-2012-7026063 | 7/2012 |
| KR | 10-2010-7026063 | 2/2013 |
| KR | 10-2010-7026063 | 9/2013 |
| KR | 10-2010-7026063 | 12/2013 |
| KR | 10-2013-7028228 | 6/2014 |
| KR | 10-2010-7026063 | 7/2014 |
| KR | 10-2012-7026483 | 7/2014 |
| KR | 10-2012-7026483 | 2/2015 |
| KR | 10-2013-7028228 | 4/2015 |
| KR | 10-2015-7007520 | 4/2015 |
| KR | 10-2015-7007520 | 11/2015 |
| MX | 2010/012473 | 7/2013 |
| MX | 2010/012473 | 3/2014 |
| MX | 2010/012473 | 6/2014 |
| MX | MX/a/2013/013310 | 7/2015 |
| MX | MX/a/2013/013310 | 4/2016 |
| MX | MX/a/2013/013310 | 2/2017 |
| RU | 2010152693 | 12/2012 |
| RU | 2010152693 | 4/2013 |
| RU | 201052693 | 5/2014 |
| RU | 2010152693 | 12/2014 |
| RU | 2015114990 | 7/2016 |
| RU | 2015114990 | 1/2017 |
| RU | 2017113349 | 5/2017 |
| RU | 2015114990 | 8/2017 |
| RU | 2015114990 | 10/2017 |
| RU | 2017113349 | 12/2018 |
| RU | 2017113349 | 4/2019 |
| RU | 2018110885 | 1/2020 |
| RU | 2017113349 | 3/2020 |
| WO | PCT/US2009/44951 | 7/2009 |
| WO | PCT/US2009/44951 | 12/2010 |
| WO | PCT/US2011/053399 | 4/2012 |
| WO | PCT/US12/31446 | 6/2012 |
| WO | PCT/US2011/061387 | 6/2012 |
| WO | 11776932.3 | 4/2013 |
| WO | PCT/US2011/061387 | 5/2013 |
| WO | PCT/US2012/031446 | 10/2013 |
| WO | PCT/US2015/050154 | 3/2016 |
| WO | PCT/US2016/034880 | 8/2016 |
| WO | PCT/US2016/039076 | 12/2016 |
| WO | PCT/US2015/050154 | 3/2017 |
| WO | PCT/US2017/018185 | 5/2017 |
| WO | PCT/US2017/027773 | 9/2017 |
| WO | PCT/US2017/018185 | 8/2018 |
| WO | PCT/US2017/027773 | 10/2018 |
| WO | PCT/US2016/039076 | 12/2018 |
| WO | PCT/US2018/030931 | 11/2019 |

OTHER PUBLICATIONS

U.S. Appl. No. 12/994,421, filed Sep. 10, 2012.
U.S. Appl. No. 12/951,768, filed Nov. 5, 2012.
U.S. Appl. No. 12/994,421, filed Feb. 26, 2013.
U.S. Appl. No. 12/951,768, filed Mar. 21, 2013.
U.S. Appl. No. 12/951,768, filed Mar. 27, 2013.
U.S. Appl. No. 12/994,421, filed May 21, 2013.
U.S. Appl. No. 12/994,421, filed Jul. 18, 2013.
U.S. Appl. No. 12/951,768, file Jul. 29, 2013.
U.S. Appl. No. 12/951,768, filed Nov. 15, 2013.
U.S. Appl. No. 12/951,768, filed Dec. 20, 2013.
U.S. Appl. No. 13/332,976, filed Sep. 3, 2014.
U.S. Appl. No. 14/247,081, filed Sep. 9, 2014.
U.S. Appl. No. 13/332,976, filed Nov. 18, 2014.
U.S. Appl. No. 12/994,421, filed Nov. 18, 2014.
U.S. Appl. No. 14/247,081, filed Jan. 13, 2015.
U.S. Appl. No. 14/247,081, filed Feb. 2, 2015.
U.S. Appl. No. 12/994,421, filed Mar. 13, 2015.
U.S. Appl. No. 13/332,976, filed Mar. 13, 2015.
U.S. Appl. No. 12/994,421, filed Mar. 27, 2015.
U.S. Appl. No. 13/332,976, filed Apr. 1, 2015.
U.S. Appl. No. 13/332,976, filed Apr. 23, 2015.
U.S. Appl. No. 13/332,976, filed May 1, 2015.
U.S. Appl. No. 14/247,081, filed May 6, 2015.
U.S. Appl. No. 13/332,976, filed Jun. 11, 2015.
U.S. Appl. No. 14/247,081, filed Jul. 10, 2015.
U.S. Appl. No. 14/278,081, filed Jul. 21, 2015.
U.S. Appl. No. 13/876,157, filed Sep. 10, 2015.
U.S. Appl. No. 12/994,421, filed Sep. 2, 2015.
U.S. Appl. No. 12/994,421, filed Jan. 19, 2016.
U.S. Appl. No. 13/876,157, filed Mar. 30, 2016.
U.S. Appl. No. 13/876,157, filed Oct. 17, 2016.
U.S. Appl. No. 14/974,095, filed Sep. 22, 2016.
U.S. Appl. No. 13/876,157, filed Jan. 5, 2017.
U.S. Appl. No. 14/974,095, filed Feb. 13, 2017.
U.S. Appl. No. 14/974,561, filed Jun. 13, 2017.
U.S. Appl. No. 14/974,095, filed Jun. 27, 2017.
U.S. Appl. No. 14/974,095, filed Sep. 22, 2017.

(56) References Cited

OTHER PUBLICATIONS

U.S. Appl. No. 14/974,561, filed Nov. 15, 2017.
U.S. Appl. No. 14/932,200, filed Nov. 30, 2017.
U.S. Appl. No. 14/974,095, filed Jan. 11, 2018.
U.S. Appl. No. 14/974,095, filed Jan. 30, 2018.
U.S. Appl. No. 14/974,561, filed Feb. 8, 2018.
U.S. Appl. No. 14/932,200, filed Feb. 21, 2018.
U.S. Appl. No. 14/974,095, filed May 11, 2018.
U.S. Appl. No. 14/920,737, filed May 14, 2018.
U.S. Appl. No. 15/511,731, filed May 21, 2018.
U.S. Appl. No. 15/489,624, filed May 21, 2018.
U.S. Appl. No. 14/974,561, filed May 29, 2018.
U.S. Appl. No. 14/932,200, filed Sep. 5, 2018.
U.S. Appl. No. 14/920,737, filed Sep. 12, 2018.
U.S. Appl. No. 14/974,561, filed Sep. 25, 2018.
U.S. Appl. No. 15/489,624, filed Oct. 23, 2018.
U.S. Appl. No. 15/511,731, filed Nov. 15, 2018.
U.S. Appl. No. 15/720,912, filed Nov. 28, 2018.
U.S. Appl. No. 14/932,200, filed Dec. 13, 2018.
U.S. Appl. No. 15/489,624, filed Jan. 23, 2019.
U.S. Appl. No. 15/863,811, filed Feb. 4, 2019.
U.S. Appl. No. 14/974,561, filed Feb. 6, 2019.
U.S. Appl. No. 15/863,784, filed Feb. 11, 2019.
U.S. Appl. No. 15/511,731, filed Feb. 14, 2019.
U.S. Appl. No. 14/920,737, filed Mar. 4, 2019.
U.S. Appl. No. 14/974,561, filed Mar. 12, 2019.
U.S. Appl. No. 15/720,912, filed Mar. 26, 2019.
U.S. Appl. No. 15/863,741, filed Apr. 10, 2019.
U.S. Appl. No. 15/863,828, filed Mar. 20, 2019.
U.S. Appl. No. 14/932,200, filed Jun. 7, 2019.
U.S. Appl. No. 14/920,737, filed Aug. 15, 2019.
U.S. Appl. No. 15/511,731, filed Jun. 27, 2019.
U.S. Appl. No. 15/863,811, filed Sep. 25, 2019.
U.S. Appl. No. 15/863,784, filed Sep. 30, 2019.
U.S. Appl. No. 15/863,828, filed Oct. 7, 2019.
U.S. Appl. No. 15/953,244, filed Oct. 11, 2019.
U.S. Appl. No. 16/092,743, filed Oct. 15, 2019.
U.S. Appl. No. 15/511,731, filed Oct. 21, 2019.
U.S. Appl. No. 15/720,912, filed Oct. 30, 2019.
U.S. Appl. No. 15/863,811, filed Nov. 1, 2019.
U.S. Appl. No. 14/932,200, filed Nov. 20, 2019.
U.S. Appl. No. 15/863,784, filed Nov. 21, 2019.
U.S. Appl. No. 15/863,741, filed Dec. 5, 2019.
U.S. Appl. No. 15/977,587, filed Dec. 11, 2019.
U.S. Appl. No. 15/863,828, filed Dec. 20, 2019.
U.S. Appl. No. 14/920,737, filed Jan. 13, 2020.
U.S. Appl. No. 15/511,731, filed Jan. 27, 2020.
U.S. Appl. No. 15/863,741, filed Feb. 13, 2020.
U.S. Appl. No. 15/863,784, filed Feb. 7, 2020.
U.S. Appl. No. 15/863,811, filed Feb. 11, 2020.
U.S. Appl. No. 15/953,244, filed Mar. 20, 2020.
U.S. Appl. No. 14/920,737, filed Mar. 31, 2020.
U.S. Appl. No. 16/092,743, filed Mar. 18, 2020.
U.S. Appl. No. 15/863,828, filed Apr. 16, 2020.
U.S. Appl. No. 15/863,741, filed Apr. 20, 2020.
"New biomarker for the prevention of arteriosclerosis", Atherosclerosis Prevention, vol. 14, No. 1, pp. 22-27, (2015).
Baxevanis, C.N. "Antibody-based cancer therapy", Expert Opinion Drug Discovery, vol. 3, No. 4, pp. 441-452, (2008).
U.S. Appl. No. 14/920,737, filed Jun. 23, 2020.
U.S. Appl. No. 15/720,912, filed Jul. 23, 2020.
U.S. Appl. No. 15/863,784, filed Jul. 24, 2020.
U.S. Appl. No. 15/863,811, filed Jul. 20, 2020.
U.S. Appl. No. 14/920,737, filed Aug. 4, 2020.
U.S. Appl. No. 15/953,244, filed Aug. 6, 2020.
U.S. Appl. No. 16/077,713, filed Aug. 12, 2020.
U.S. Appl. No. 16/440,747, filed Sep. 9, 2020.
U.S. Appl. No. 15/863,784, filed Sep. 16, 2020.
U.S. Appl. No. 15/953,244, filed Sep. 16, 2020.
U.S. Appl. No. 15/863,811, filed Sep. 29, 2020.
U.S. Appl. No. 15/863,828, filed Sep. 17, 2020.
U.S. Appl. No. 15/863,741, filed Oct. 13, 2020.
U.S. Appl. No. 16/311,149, filed Oct. 21, 2020.
U.S. Appl. No. 15/863,811, filed Oct. 22, 2020.
Malatesta, M. "skeletal muscle features in myotonic dystrophy and sarcopenia: do similar nuclear mechanisms lead to skeletal wasting?", European Journal of Histochemistry, vol. 56, pp. 228-230, (2012).
Wingerchuk, D.M. et al., "Multiple sclerosis: Current and emerging disease-modifying therapies and treatment strategies", Mayo Clinic Proceedings, vol. 89, No. 2, pp. 225-240, (2014).
Matias-Guiu J.A. et al., "Amyloid proteins and their role in multiple sclerosis. Considerations in the use of amyloid-PET imaging", Frontiers in Neurology, vol. 7, article 53, pp. 1-7, (2016).
Sternberg, Z. et al., "Diagnostic potential of plasma carbxymethyllysine and carboxyethyllysine in multiple sclerosis", Journal of Neuroinflammation, vol. 7, No. 72, pp. 1-8, (2010).
U.S. Appl. No. 15/953,244, filed Nov. 12, 2020.
U.S. Appl. No. 14/920,737, filed Nov. 9, 2020.
U.S. Appl. No. 16/228,293, filed Nov. 19, 2020.
U.S. Appl. No. 15/863,828, filed Oct. 27, 2020.
U.S. Appl. No. 15/863,741, filed Oct. 27, 2020.
U.S. Appl. No. 15/863,741, filed Nov. 5, 2020.
U.S. Appl. No. 16/092,743, filed Nov. 6, 2020.

* cited by examiner

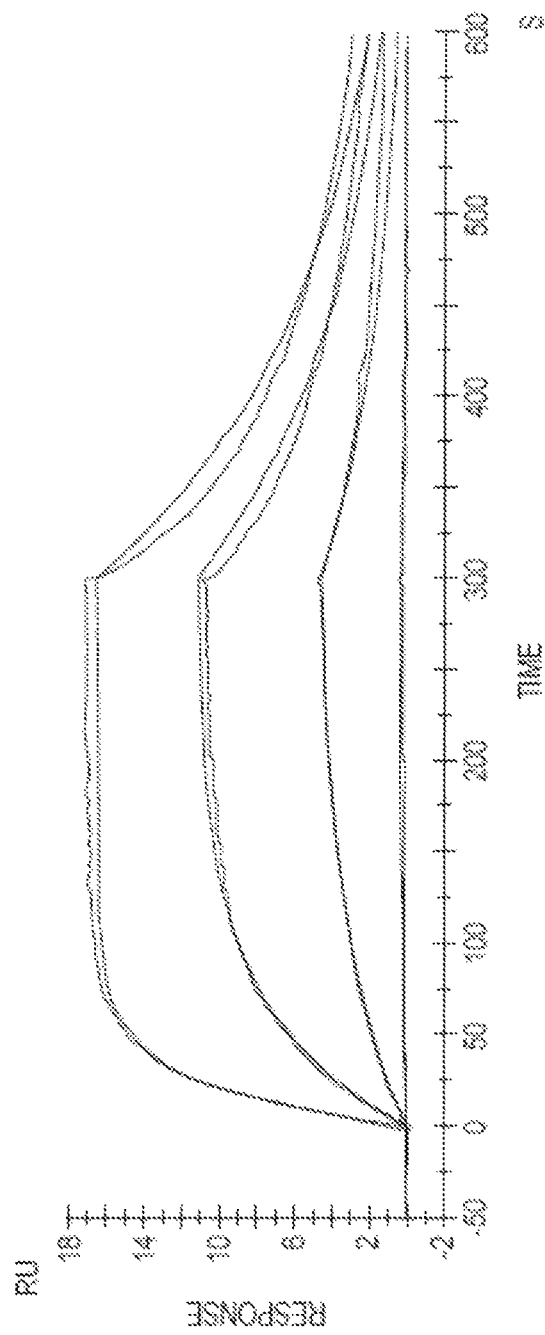

ANTI-AGE ANTIBODIES AND METHODS OF USE THEREOF

BACKGROUND

Sarcopenia is the loss of muscle mass, quality and strength associated with aging. Humans begin to lose muscle mass and function at some point in the third decade of life. This loss of muscle mass typically accelerates around age 75. Sarcopenia develops in both physically active and physically inactive people. As the average human lifespan continues to increase, sarcopenia is becoming a significant health concern. The loss of muscle mass from sarcopenia may lead to poor balance, reduced gait speed and frailty. Individuals suffering from sarcopenia are more susceptible to injury and disability, and may be unable to live independently as a result. The spread of sarcopenia will likely result in increases in health care and assisted living expenses.

Sarcopenia has been considered to be an inevitable result of aging and the natural deterioration of the body over time. The primary treatment for sarcopenia is exercise. Physical exercise, particularly resistance training or strength training, can reduce the impact of sarcopenia. Testosterone, anabolic steroids, ghrelin, vitamin D, angiotensin converting enzyme inhibitors (ACE inhibitors), eicosapentaenoic add (EPA), myostatin, selective androgen receptor modulators (SARMs), urocortin II (Ucn2) and hormone replacement therapy have been investigated or are being studied as potential treatments for sarcopenia. Despite this research, there are currently no U.S. Food and Drug Administration (FDA)-approved agents for treating sarcopenia.

A recent study has identified a causal link between cellular senescence and age-related disorders, such as sarcopenia. A research team at the Mayo Clinic in Rochester, Minn., demonstrated that effects of aging in mice could be delayed by eliminating senescent cells in their fat and muscle tissues without overt side effects (Baker, D. J. et al., "Clearance of p16$^{Ink4a}$-positive senescent cells delays aging-associated disorders", Nature, Vol. 479, pp. 232-236, (2011)). Elimination of senescent cells in transgenic mice was shown to substantially delay the onset of sarcopenia and cataracts, and to reduce senescence indicators in skeletal muscle and the eye. The study established that life-long and late-life treatment of transgenic mice for removal of senescent cells has no negative side effects and selectively delays age-related phenotypes that depend on cells (Id., page 234, col. 2, line 16 through page 235, col. 1, line 2). The authors theorized that removal of senescent cells may represent an avenue for treating or delaying age-related diseases in humans and improving healthy human lifespan (Id., page 235, col. 2, lines 38-51).

Senescent cells are cells that are partially-functional or non-functional and are in a state of irreversible proliferative arrest. Senescence is a distinct state of a cell, and is associated with biomarkers, such as activation of the biomarker p16$^{Ink4a}$, and expression of β-galactosidase.

Advanced glycation end-products (AGEs; also referred to AGE-modified proteins, or glycation end-products) arise from a non-enzymatic reaction of sugars with protein sidechains in aging cells (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between the reducing sugar and the amino group to form a Schiff base, which proceeds to form a covalently-bonded Amadori rearrangement product. Once formed, the Amadori product undergoes further rearrangement to produce AGEs. Hyperglycemia, caused by diabetes mellitus (DM), and oxidative stress promote this post-translational modification of membrane proteins (Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009)). AGEs have been associated with several pathological conditions including diabetic complications, inflammation, retinopathy, nephropathy, atherosclerosis, stroke, endothelial cell dysfunction, and neurodegenerative disorders (Bierhaus A, "AGEs and their interaction with AGE-receptors in vascular disease and diabetes mellitus. I. The AGE concept," Cardiovasc Res, Vol. 37(3), 586-600 (1998)).

AGE-modified proteins are also a marker of senescent cells. This association between glycation end-product and senescence is well known in the art. See, for example, Gruber, L. (WO 2009/143411, 26 Nov. 2009), Ando, K. et al. (Membrane Proteins of Human Erythrocytes Are Modified by Advanced Glycation End Products during Aging in the Circulation, *Biochem Biophys Res Commun.*, Vol. 258, 123, 125 (1999)), Ahmed, E. K. et al. ("Protein Modification and Replicative Senescence of WI-38 Human Embryonic Fibroblasts" *Aging Cells*, vol. 9, 252, 260 (2010)), Vlassara, H. et al. (Advanced Glycosylation Endproducts on Erythrocyte Cell Surface Induce Receptor-Mediated Phagocytosis by Macrophages, *J. Exp. Med.*, Vol. 166, 539, 545 (1987)) and Vlassara et al. ("High-affinity-receptor-mediated Uptake and Degradation of Glucose-modified Proteins: A Potential Mechanism for the Removal of Senescent Macromolecules" *Proc. Natl. Acad. Sci. USA*, Vol. 82, 5588, 5591 (1985)). Furthermore, Ahmed, E. K. et al. indicates that glycation end-products are "one of the major causes of spontaneous damage to cellular and extracellular proteins" (Ahmed, E. K. et al., see above, page 353). Accordingly, the accumulation of glycation end-products is associated with senescence and lack of function.

Cellular senescence and the accumulation of AGEs have been implicated in a number of diseases and disorders in addition to sarcopenia and age-related disorders. Senescence of cells in the central nervous system such as glial cells, astrocytes and microglial cells has been associated with neurodegenerative disorders. Abnormal accumulation of senescent astrocytes has been associated with Alzheimer's disease (AD) (Bhat, R. et al., "Astrocyte Senescence as a Component of Alzheimer's Disease", *PLOS ONE*, Vol. 7(9), e45069, pp. 1-10 (September 2012)). Microglial cell senescence associated with normal aging is exacerbated by the presence of the amyloid plaques indicative of AD (Flanary, B. E. et al., "Evidence That Aging And Amyloid Promote Microglial Cell Senescence", *Rejuvenation Research*, Vol. 10(1), pp. 61-74 (March 2007)). The presence of AGEs with astrocytes and microglial cells in AD is further evidence of the presence of senescent cells (Takeda, A., et al. "Advanced glycation end products co-localize with astrocyes and microglial cells in Alzheimer's disease brain", *Acta Neuropathologica*, Vol. 95, pp. 555-558 (1998)). On the basis of recently reported findings, Chinta et al. proposed that environmental stressors associated with Parkinson's disease (PD) may act in part by eliciting senescence within non-neuronal glial cells, contributing to the characteristic decline in neuronal integrity that occurs in this disorder (Chinta, S. J. et al. "Environmental stress, ageing and glial cell senescence: a novel mechanistic link to Parkinson's disease?", *J Intern Med*, Vol. 273, pp. 429-436 (2013)). Astrocyte senescence is also associated with PD (M. Mori, "The Parkinsonian Brain: Cellular Senescence and Neurodegeneration, *SAGE* (Jun.

30, 2015) (sage.buckinstitute.org/the-parkinsonian-brain-cellular-senescence-and-neurodegeneration/). In a rodent model of familial amyotrophic lateral sclerosis (ALS) overexpressing mutant superoxide dismutase-1 (m-SOD1), the rate of astrocytes acquiring a senescent phenotype is accelerated (Das, M. M. and Svendsen, C. N., "Astrocytes show reduced support of motor neurons with aging that is accelerated in a rodent model of ALS", Neurobiology of Aging, Vol. 36, pp. 1130-1139 (2015)). Even in multiple sclerosis (MS), microglia and macrophages are shifted toward a strongly proinflammatory phenotype, reminiscent of SASP, and may potentiate neuronal damage by releasing proinflammatory cytokines and molecules (Luessi, F., et al. "Neurodegeneration in multiple sclerosis: novel treatment strategies" Expert Rev. Neurother., Vol 9, pp. 1061-1077 (2012)).

Some neurodegenerative disorders are associated with abnormal cellular senescence outside the central nervous system. Most satellite cells, also known as myosatellite cells, present in the muscle tissue of ALS patients exhibit an abnormal senescent-like morphology, although they may be capable of proliferating in vitro (Pradat, P.-F. et al., "Abnormalities of satellite cells function in amyotrophic lateral sclerosis" Amyotrophic Lateral Sclerosis, Vol. 12, pp. 264-271 (2011)). Satellite cells are small multipotent cells found in mature muscle, which are able to give rise to additional satellite cells, or differentiate into myoblasts as well as provide additional myonuclei. In an animal model of Duchenne muscular dystrophy (MD), reduced proliferative capacity and premature senescence of myoblasts was observed (Wright, W. E., "Myoblast Senescence in Muscular Dystrophy" Exp Cell Res, Vol. 157, pp. 343-354 (1985)). Myoblasts are precursor cells which differentiate into myocytes (also referred to as muscle cells).

Neurodegenerative disorders are also associated with abnormal protein accumulations (King, O. D., et al., "The tip of the iceberg: RNA-binding proteins with prion-like domains in neurodegenerative disease" Brain Res. Vol. 1462, pp. 61-80 (2012)). A characteristic of PD and Lewy body dementia is the formation of Lewy bodies that form inside nerve cells. The primary structural component of the Lewy bodies is alpha-synuclein protein, in the form of fibrils. The presence of tangles and plaques are a characteristic of AD, the presence of which is used to definitively diagnose the condition. Plaques, composed of beta-amyloid protein (also referred to as amyloid beta, Aβ or Abeta), accumulate between nerve cells. Tangles, composed of tau protein, form twisted fibers within cells. Prion diseases (also known as transmissible spongiform encephalopathies (TSEs)), include a variety of human and animal disorder such as Creutzfeldt-Jakob disease, variant Creutzfeldt-Jakob disease, bovine spongiform encephalopathy ("mad cow" disease), scrapie (in sheep and goats), chronic wasting disease (in deer and elk), kuru and fatal familial insomnia. Prion protein is a misfolded protein molecule which may propagate by transmitting a misfolded protein state, resulting in the accumulation of the misfolded protein and causing tissue damage and cell death (Dobson, D. M., "The structural basis of protein folding and its links with human disease" Phil. Trans. R. Soc. Lond. B, Vol. 356, pp. 133-145 (2001)). In these diseases, it is believed the protein is a normal protein which misfolds or forms an abnormal aggregate. In the case of some patients with familial ALS, a mutated superoxide dismutase-1 (SOD1) forms inclusions and accumulates (Kato, S., et al. "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation" Acta Neuropathol, Vol. 100, pp. 490-505 (2000)).

Senescent cells are also known to fuel the growth of cancer cells. Senescent cells are associated with secretion of many factors involved in intercellular signaling, including pro-inflammatory factors; secretion of these factors has been termed the senescence-associated secretory phenotype, or SASP. One study showed that senescent mesenchymal stem cells promote proliferation and migration of breast cancer cells by the secretion of IL-6 (Di, G-h. et al. IL-6 Secreted from Senescent Mesenchymal Stem Cells Promotes Proliferation and migration of Breast Cancer Cells, PLOS One, Vol. 9, 11, e113572 (2014)). Another study showed that senescent human fibroblasts increase the growth of tumors by the secretion of matrix metalloproteinase (Liu, D. et al. Senescent Human Fibroblasts Increase the Early Growth of Xenograft Tumors via Matrix Metalloproteinase Secretion, Cancer Res, Vol. 67, 3117-3126 (2007)).

SUMMARY

In a first aspect, the present invention is an anti-AGE antibody, comprising a protein or peptide comprising at least one amino acid sequence having at least 90% sequence identity, preferably at least 95% sequence identity, more preferably at least 98% sequence identity, with an amino acid sequence selected from the group consisting of SEQ ID NO: 1, SEQ ID NO: 3, SEQ ID NO: 17, SEQ ID NO: 19, SEQ ID NO: 29, SEQ ID NO: 31, SEQ ID NO: 33, SEQ ID NO: 35, SEQ ID NO: 37, and SEQ ID NO: 39. The antibody binds to a protein or peptide that exhibits a carboxymethyllysine modification.

In a second aspect, the present invention is an anti-AGE antibody, comprising a protein or peptide comprising at least one amino acid sequence having at least 90% sequence identity, preferably at least 95% sequence identity, more preferably at least 98% sequence identity, with an amino acid sequence selected from the group consisting of SEQ ID NO: 22, SEQ ID NO: 23, SEQ ID NO: 24, SEQ ID NO: 25, SEQ ID NO: 26, SEQ ID NO: 27, and SEQ ID NO: 28. The antibody binds to a protein or peptide that exhibits a carboxymethyllysine modification.

In a third aspect, the present invention is an anti-AGE antibody comprising a heavy chain and a light chain. The heavy chain comprises an amino acid sequence having at least 90% sequence identity, preferably at least 95% sequence identity, more preferably at least 98% sequence identity, with an amino acid sequence selected from the group consisting of SEQ ID NO: 1, SEQ ID NO: 17, SEQ ID NO: 29, SEQ ID NO: 31, and SEQ ID NO: 33, or the light chain comprises an amino acid sequence having at least 90% sequence identity, preferably at least 95% sequence identity, more preferably at least 98% sequence identity, with an amino acid sequence selected from the group consisting of SEQ ID NO: 3, SEQ ID NO: 19, SEQ ID NO: 35, SEQ ID NO: 37, and SEQ ID NO: 39. The antibody binds to a protein or peptide that exhibits a carboxymethyllysine modification.

In a fourth aspect, the present invention is an anti-AGE antibody comprising a heavy chain and a light chain. The heavy chain comprises an amino acid sequence having at least 90% sequence identity, preferably at least 95% sequence identity, more preferably at least 98% sequence identity, with an amino acid sequence selected from the group consisting of SEQ ID NO: 1, SEQ ID NO: 17, SEQ ID NO: 29, SEQ ID NO: 31, and SEQ ID NO: 33, and the light chain comprises an amino acid sequence having at least 90% sequence identity, preferably at least 95% sequence identity, more preferably at least 98% sequence identity, with an amino acid sequence selected from the group consisting of SEQ ID NO: 3, SEQ ID NO: 19, SEQ ID NO: 35, SEQ ID NO: 37, and SEQ ID NO: 39. The antibody binds to a protein or peptide that exhibits a carboxymethyllysine modification.

In a fifth aspect, the present invention is an anti-AGE antibody, comprising complementary determining region comprising at least one amino acid sequence having at least 90% sequence identity, preferably at least 95% sequence identity, more preferably at least 98% sequence identity, with an amino acid sequence selected from the group consisting of SEQ ID NO: 23, SEQ ID NO: 24, SEQ ID NO: 25, SEQ ID NO: 26, SEQ ID NO: 27, and SEQ ID NO: 28. The antibody binds to a protein or peptide that exhibits a carboxymethyllysine modification. The antibody is substantially non-immunogenic to a species selected from the group consisting of mice, rats, goats, sheep, cows, horses, dogs and cats.

In a sixth aspect, the present invention is an antibody conjugate, comprising an anti-AGE antibody fragment comprising a protein or peptide comprising at least one amino acid sequence having at least 90% sequence identity, preferably at least 95% sequence identity, more preferably at least 98% sequence identity, with an amino acid sequence selected from the group consisting of SEQ ID NO: 1, SEQ ID NO: 3, SEQ ID NO: 17, SEQ ID NO: 19, SEQ ID NO: 29, SEQ ID NO: 31, SEQ ID NO: 33, SEQ ID NO: 35, SEQ ID NO: 37, and SEQ ID NO: 39, and an agent that causes the destruction of AGE-modified cells. The agent that causes the destruction of AGE-modified cells is conjugated to the anti-AGE antibody fragment. The antibody binds to a protein or peptide that exhibits a carboxymethyllysine modification.

Definitions

The term "peptide" means a molecule composed of 2-50 amino acids.

The term "protein" means a molecule composed of more than 50 amino acids.

The term "sarcopenia" means the syndrome characterized by the presence of (1) low muscle mass and (2) low muscle function (low muscle strength or reduced physical performance). Muscle mass may be measured by body imaging techniques, such as computed tomography scanning (CT scan), magnetic resonance imaging (MRI) or dual energy X-ray absorptiometry (DXA or DEXA); bioimpedance analysis (BIA); body potassium measurement, such as total body potassium (TBK) or partial body potassium (PBK); or anthropometric measurements, such as mid-upper arm circumference, skin fold thickness or calf circumference. Preferably, muscle mass is measured by CT scan, MRI or DXA. Muscle strength may be measured by handgrip strength, knee flexion/extension or peak expiratory flow. Preferably, muscle strength is measured by handgrip strength. Physical performance may be measured by the Short Physical Performance Battery, gait speed measurement, timed get-up-and-go (TGUG) or the stair climb power test. Preferably, physical performance is measured by gait speed measurement. A subject may be identified as having sarcopenia or in need of treatment if (1) the subject is at least 25 years old and (2) his or her measured muscle mass and measured muscle function are two standard deviations or more below the mean value for healthy 25 year olds of the same gender and no alternative pathology has been identified to account for the reduced muscle mass and reduced muscle function. Preferably, a subject being treated for sarcopenia is at least 40 years old. More preferably, a subject being treated for sarcopenia is at least 50 years old. Most preferably, a subject being treated for sarcopenia is at least 60 years old. Alternatively, a subject may be identified as having sarcopenia or in need of treatment if (1) his or her gait speed is less than 1.0 m/s across a 4 m course and (2) he or she has an objectively measured low muscle mass, such as, for example, an appendicular mass relative to the square of height less than or equal to 7.23 kg/m$^2$ for male subjects or less than or equal to 5.67 kg/m$^2$ for female subjects (Fielding, R. A., et al., "Sarcopenia: an undiagnosed condition in older adults. Current consensus definition: prevalence, etiology, and consequences", *Journal of the American Medical Directors Association*, Vol. 12(4), pp. 249-256 (May 2011).

The term "neurodegenerative disorder" means disorders which result in neurons loosing function and/or dying, in the central nervous system including the brain. Such disorders included central nervous system neurodegenerative disorders such as AD, PD, Lewy body dementia, MS, prion diseases (also known as transmissible spongiform encephalopathies (TSEs), including Creutzfeldt-Jakob disease, variant Creutzfeldt-Jakob disease, bovine spongiform encephalopathy ("mad cow" disease), scrapie (in sheep and goats), chronic wasting disease (in deer and elk), kuru and fatal familial insomnia), and ALS.

"Neurodegenerative proteins" are proteins which accumulate in a patient having a neurodegenerative disorders and which are associated with the neurodegenerative disorder. Examples include, beta-amyloid protein plaques (associated with AD), tau protein tangles (associated with AD), mutated superoxide dismutase-1 (associated with ALS), prion protein aggregates (associated with TSEs) and alpha-synuclein protein fibrils (associated with PD and Lewy Body dementia). A "neurodegenerative protein" is the form of the protein which accumulates during the neurodegenerative disorder, typically a mutant or mis-folded form.

The terms "advanced glycation end-product," "AGE," "AGE-modified protein or peptide," "glycation end-product" and "AGE antigen" refer to modified proteins or peptides that are formed as the result of the reaction of sugars with protein side chains that further rearrange and form irreversible cross-links. This process begins with a reversible reaction between a reducing sugar and an amino group to form a Schiff base, which proceeds to form a covalently-bonded Amadori rearrangement product. Once formed, the Amadori product undergoes further rearrangement to produce AGEs. AGE-modified proteins and antibodies to AGE-modified proteins are described in U.S. Pat. No. 5,702,704 to Bucala ("Bucala") and U.S. Pat. No. 6,380,165 to Al-Abed et al. ("Al-Abed"). Glycated proteins or peptides that have not undergone the necessary rearrangement to form AGEs, such as N-deoxyfructosyllysine found on glycated albumin, are not AGEs. AGEs may be identified by the presence of AGE modifications (also referred to as AGE epitopes or AGE moieties) such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; and pentosidine. ALI, another AGE, is described in Al-Abed.

"An antibody that binds to an AGE-modified protein on a cell", "anti-AGE antibody" or "AGE antibody" means an antibody, antibody fragment or other protein or peptide that binds to an AGE-modified protein or peptide which preferably includes a constant region of an antibody, where the protein or peptide which has been AGE-modified is a protein or peptide normally found bound on the surface of a cell, preferably a mammalian cell, more preferably a human, cat, dog, horse, camelid (for example, camel or alpaca), cattle, sheep, or goat cell. "An antibody that binds to an AGE-modified protein on a cell", "anti-AGE antibody" or "AGE antibody" does not include an antibody or other protein which binds with the same specificity and selectivity to both the AGE-modified protein or peptide, and the same non-AGE-modified protein or peptide (that is, the presence of the AGE modification does not increase binding). AGE-modified albumin is not an AGE-modified protein on a cell, because albumin is not a protein normally found bound on the surface of cells. "An antibody that binds to an AGE-modified protein on a cell", "anti-AGE antibody" or "AGE antibody" only includes those antibodies which lead to removal, destruction, or death of the cell. Also included are antibodies which are conjugated, for example to a toxin, drug, or other chemical or particle. Preferably, the antibodies are monoclonal antibodies, but polyclonal antibodies are also possible.

The term "senescent cell" means a cell which is in a state of irreversible proliferative arrest and expresses one or more biomarkers of senescence, such as activation of p16$^{Ink4a}$ or expression of senescence-associated β-galactosidase. Also included are cells which express one or more biomarkers of senescence, do not proliferate in vivo, but may proliferate in vitro under certain conditions, such as some satellite cells found in the muscles of ALS patients.

The term "increasing health span" means reducing age-related phenotypes. Age-related phenotypes include, for example, sarcopenia, cataracts, loss of adipose tissue and lordokyphosis.

The term "variant" means a nucleotide, protein or amino acid sequence different from the specifically identified sequences, wherein one or more nucleotides, proteins or amino acid residues is deleted, substituted or added. Variants may be naturally-occurring allelic variants, or non-naturally-occurring variants. Variants of the identified sequences may retain some or all of the functional characteristics of the identified sequences.

The term "percent (%) sequence identity" is defined as the percentage of amino acid residues in a candidate sequence that are identical to the amino acid residues in a reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using publicly available computer software such as BLAST, BLAST-2, ALIGN or Megalign (DNASTAR) software. Preferably, % sequence identity values are generated using the sequence comparison computer program ALIGN-2. The ALIGN-2 sequence comparison computer program is publicly available from Genentech, Inc. (South San Francisco, Calif.), or may be compiled from the source code, which has been filed with user documentation in the U.S. Copyright Office and is registered under U.S. Copyright Registration No. TXU510087. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained using the ALIGN-2 computer program.

BRIEF DESCRIPTION OF THE DRAWING

FIG. 1 is a graph of the response versus time in an antibody binding experiment.

DETAILED DESCRIPTION

The identification of a link between cellular senescence and sarcopenia allows for new treatment possibilities. For example, if anti-AGE antibodies are administered to a subject, the antibodies will specifically and selectively target senescent cells, and kill or induce apoptosis in such cells expressing an AGE-modified protein or peptide.

The present invention makes use of the discovery that enhanced clearance of cells expressing AGE-modified proteins or peptides (AGE-modified cells) is beneficial in treating or ameliorating sarcopenia. This may be accomplished by administering anti-AGE antibodies to a subject.

Administering anti-AGE antibodies to a subject may also be used for increasing health span. Health span may be increased by reducing age-related phenotypes. Administering anti-AGE antibodies may be used, for example, to prevent or delay the onset of cataracts, lordokyphosis or loss of adipose tissue.

Other diseases or disorders that are associated with cellular senescence may also be treated or ameliorated with anti-AGE antibodies. For example, anti-AGE antibodies may be used therapeutically to treat neurodegenerative disorders or cancer.

An antibody that binds to an AGE-modified protein on a cell ("anti-AGE antibody" or "AGE antibody") is known in the art. Examples include those described in U.S. Pat. No. 5,702,704 (Bucala) and U.S. Pat. No. 6,380,165 (Al-Abed et al.). Examples include an antibody that binds to one or more AGE-modified proteins having an AGE modification such as FFI, pyrraline, AFGP, ALI, carboxymethyllysine, carboxyethyllysine and pentosidine, and mixtures of such antibodies. Preferably, the antibody binds carboxymethyllysine-modified proteins. Preferably, the antibody is non-immunogenic to the animal in which it will be used, such as non-immunogenic to humans; companion animals including cats, dogs and horses; and commercially important animals, such camels (or alpaca), cattle (bovine), sheep, and goats. More preferably, the antibody has the same species constant region as antibodies of the animal to reduce the immune response against the antibody, such as being humanized (for humans), felinized (for cats), caninized (for dogs), equuinized (for horses), camelized (for camels or alpaca), bovinized (for cattle), ovinized (for sheep), or caperized (for goats). Most preferably, the antibody is identical to that of the animal in which it will be used (except for the variable region), such as a human antibody, a cat antibody, a dog antibody, a horse antibody, a camel antibody, a bovine antibody, a sheep antibody or a goat antibody. Details of the constant regions and other parts of antibodies for these animals are described below. Preferably, the antibody is a monoclonal antibody.

A particularly preferred anti-AGE antibody is an antibody which binds to a protein or peptide that exhibits a carboxymethyllysine modification. Carboxymethyllysine (also known as CML, N(epsilon)-(carboxymethyl)lysine, N(6)-carboxymethyllysine, or 2-Amino-6-(carboxymethylamino) hexanoic acid) is found on proteins or peptides and lipids as a result of oxidative stress and chemical glycation, and has been correlated with aging. CML-modified proteins or peptides are recognized by the receptor RAGE which is expressed on a variety of cells. CML has been well-studied and CML-related products are commercially available. For example, Cell Biolabs, Inc. sells CML-BSA antigens, CML polyclonal antibodies, CML immunoblot kits, and CML competitive ELISA kits (www.cellbiolabs.com/cml-assays). A particularly preferred antibody includes the variable region of the commercially available mouse anti-glycation end-product antibody raised against carboxymethyl lysine conjugated with keyhole limpet hemocyanin, the carboxymethyl lysine MAb (Clone 318003) available from R&D Systems, Inc. (Minneapolis, Minn.; catalog no. MAB3247), modified to have a human constant region (or the constant region of the animal into which it will be administered). Commercially-available antibodies, such as the carboxymethyl lysine antibody corresponding to catalog no. MAB3247 from R&D Systems, Inc., may be intended for diagnostic purposes and may contain material that is not suited for use in animals or humans. Preferably, commercially-available antibodies are purified and/or isolated prior to use in animals or humans to remove toxins or other potentially-harmful material.

The anti-AGE antibody has low rate of dissociation from the antibody-antigen complex, or $k_d$ (also referred to as $k_{back}$ or off-rate), preferably at most $9 \times 10^{-3}$, $8 \times 10^{-3}$, $7 \times 10^{-3}$ or $6 \times 10^{-3}$ (sec$^{-1}$). The anti-AGE antibody has a high affinity for the AGE-modified protein of a cell, which may be expressed as a low dissociation constant $K_D$ of at most $9 \times 10^{-6}$, $8 \times 10^{-6}$, $7 \times 10^{-6}$, $6 \times 10^{0.6}$, $5 \times 10^{-6}$, $4 \times 10^{-6}$ or $3 \times 10^{-6}$ (M). Preferably, the binding properties of the anti-AGE antibody are similar to, the same as, or superior to the carboxymethyl lysine MAb (Clone 318003) available from R&D Systems, Inc. (Minneapolis, Minn.; catalog no. MAB3247), illustrated in FIG. 1.

The anti-AGE antibody may destroy AGE-modified cells through antibody-dependent cell-mediated cytotoxicity (ADCC). ADCC is a mechanism of cell-mediated immune defense in which an effector cell of the immune system actively lyses a target cell whose membrane-surface antigens have been bound by specific antibodies. ADCC may be mediated by natural killer (NK) cells, macrophages, neutrophils or eosinophils. The effector cells bind to the Fc portion of the bound antibody.

The anti-AGE antibody may be conjugated to an agent that causes the destruction of AGE-modified cells. Such agents may be a toxin, a cytotoxic agent, magnetic nanoparticles, and magnetic spin-vortex discs.

A toxin, such as pore-forming toxins (PFT) (Aroian R. et al., "Pore-Forming Toxins and Cellular Non-Immune Defenses (CNIDs)," *Current Opinion in Microbiology*, 10:57-61 (2007)), conjugated to an anti-AGE antibody may be injected into a patient to selectively target and remove AGE-modified cells. The anti-AGE antibody recognizes and binds to AGE-modified cells. Then, the toxin causes pore formation at the cell surface and subsequent cell removal through osmotic lysis.

Magnetic nanoparticles conjugated to the anti-AGE antibody may be injected into a patient to target and remove AGE-modified cells. The magnetic nanoparticles can be heated by applying a magnetic field in order to selectively remove the AGE-modified cells.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to anti-AGE antibodies specifically target AGE-modified cell types, without removing other cells.

Antibodies typically comprise two heavy chains and two light chains of polypeptides joined to form a "Y" shaped molecule. The constant region determines the mechanism used to target the antigen. The amino acid sequence in the tips of the "Y" (the variable region) varies among different antibodies. This variation gives the antibody its specificity for binding antigen. The variable region, which includes the ends of the light and heavy chains, is further subdivided into hypervariable (HV—also sometimes referred to as complementarity determining regions, or CDRs) and framework (FR) regions. When antibodies are prepared recombinantly, it is also possible to have a single antibody with variable regions (or complementary determining regions) that bind to two different antigens, with each tip of the "Y" being specific to each antigen; these are referred to as bi-specific antibodies.

A humanized anti-AGE antibody according to the present invention may have the human constant region sequence of amino acids shown in SEQ ID NO: 22. The heavy chain complementarity determining regions of the humanized anti-AGE antibody may have one or more of the protein sequences shown in SEQ ID NO: 23 (CDR1H), SEQ ID NO: 24 (CDR2H) and SEQ ID NO: 25 (CDR3H). The light chain complementarity determining regions of the humanized anti-AGE antibody may have one or more of the protein sequences shown in SEQ ID NO: 26 (CDR1L), SEQ ID NO: 27 (CDR2L) and SEQ ID NO: 28 (CDR3L).

The heavy chain of human (*Homo sapiens*) antibody immunoglobulin G1 may have or may include the protein sequence of SEQ ID NO: 1. The variable domain of the heavy chain may have or may include the protein sequence of SEQ ID NO: 2. The complementarity determining regions of the variable domain of the heavy chain (SEQ ID NO: 2) are shown in SEQ ID NO: 41, SEQ ID NO: 42 and SEQ ID NO: 43. The kappa light chain of human (*Homo sapiens*) antibody immunoglobulin G1 may have or may include the protein sequence of SEQ ID NO: 3. The variable domain of the kappa light chain may have or may include the protein sequence of SEQ ID NO: 4. Optionally, the arginine (Arg or R) residue at position 128 of SEQ ID NO: 4 may be omitted. The complementarity determining regions of the variable domain of the light chain (SEQ ID NO: 4) are shown in SEQ ID NO: 44, SEQ ID NO: 45 and SEQ ID NO: 46. The variable regions may be codon-optimized, synthesized and cloned into expression vectors containing human immunoglobulin G1 constant regions. In addition, the variable regions may be used in the humanization of non-human antibodies.

The antibody heavy chain may be encoded by the DNA sequence of SEQ ID NO: 12, a murine anti-AGE immunoglobulin G2b heavy chain. The protein sequence of the murine anti-AGE immunoglobulin G2b heavy chain encoded by SEQ ID NO: 12 is shown in SEQ ID NO: 16. The variable region of the murine antibody is shown in SEQ ID NO: 20, which corresponds to positions 25-142 of SEQ ID NO: 16. The antibody heavy chain may alternatively be encoded by the DNA sequence of SEQ ID NO: 13, a chimeric anti-AGE human immunoglobulin G1 heavy chain. The protein sequence of the chimeric anti-AGE human immunoglobulin G1 heavy chain encoded by SEQ ID NO: 13 is shown in SEQ ID NO: 17. The chimeric anti-AGE human immunoglobulin includes the murine variable region of SEQ ID NO: 20 in positions 25-142. The antibody light chain may be encoded by the DNA sequence of SEQ ID NO: 14, a murine anti-AGE kappa light chain. The protein sequence of the murine anti-AGE kappa light chain encoded by SEQ ID NO: 14 is shown in SEQ ID NO: 18. The variable region of the murine antibody is shown in SEQ ID NO: 21, which corresponds to positions 21-132 of SEQ ID NO: 18. The antibody light chain may alternatively be encoded by the DNA sequence of SEQ ID NO: 15, a chimeric anti-AGE human kappa light chain. The protein sequence of the chimeric anti-AGE human kappa light chain encoded by SEQ ID NO: 15 is shown in SEQ ID NO: 19. The chimeric anti-AGE human immunoglobulin includes the murine variable region of SEQ ID NO: 21 in positions 21-132.

A humanized anti-AGE antibody according to the present invention may have or may include one or more humanized heavy chains or humanized light chains. A humanized heavy chain may be encoded by the DNA sequence of SEQ ID NO: 30, 32 or 34. The protein sequences of the humanized heavy chains encoded by SEQ ID NOs: 30, 32 and 34 are shown in SEQ ID NOs: 29, 31 and 33, respectively. A humanized light chain may be encoded by the DNA sequence of SEQ ID NO: 36, 38 or 40. The protein sequences of the humanized light chains encoded by SEQ ID NOs: 36, 38 and 40 are shown in SEQ ID NOs: 35, 37 and 39, respectively. Preferably, the humanized anti-AGE antibody maximizes the amount of human sequence while retaining the original antibody specificity. A complete humanized antibody may be constructed that contains a heavy chain having a protein sequence chosen from SEQ ID NOs: 29, 31 and 33 and a light chain having a protein sequence chosen from SEQ ID NOs: 35, 37 and 39.

The protein sequence of an antibody from a non-human species may be modified to include the variable domain of the heavy chain having the sequence shown in SEQ ID NO: 2 or the kappa light chain having the sequence shown in SEQ ID NO: 4. The non-human species may be a companion animal, such as the domestic cat or domestic dog, or livestock, such as cattle, the horse or the camel. Preferably, the non-human species is not the mouse. The heavy chain of the horse (*Equus caballus*) antibody immunoglobulin gamma 4 may have or may include the protein sequence of SEQ ID NO: 5 (EMBL/GenBank accession number AY445518). The heavy chain of the horse (*Equus caballus*) antibody immunoglobulin delta may have or may include the protein sequence of SEQ ID NO: 6 (EMBL/GenBank accession number AY631942). The heavy chain of the dog (*Canis familiaris*) antibody immunoglobulin A may have or may include the protein sequence of SEQ ID NO: 7 (GenBank accession number L36871). The heavy chain of the dog (*Canis familiaris*) antibody immunoglobulin E may have or may include the protein sequence of SEQ ID NO: 8 (GenBank accession number L36872). The heavy chain of the cat (*Felis catus*) antibody immunoglobulin G2 may have or may include the protein sequence of SEQ ID NO: 9 (DDBJ/EMBL/GenBank accession number KF811175).

Animals of the camelid family, such as camels (*Camelus dromedarius* and *Camelus bactrianus*), llamas (*Lama glama, Lama pacos* and *Lama vicugna*), alpacas (*Vicugna pacos*) and guanacos (*Lama guanicoe*), have a unique antibody that is not found in other mammals. In addition to conventional immunoglobulin G antibodies composed of heavy and light chain tetramers, camelids also have heavy chain immunoglobulin G antibodies that do not contain light chains and exist as heavy chain dimers. These antibodies are known as heavy chain antibodies, HCAbs, single-domain antibodies or sdAbs, and the variable domain of a camelid heavy chain antibody is known as the VHH. The camelid heavy chain antibodies lack the heavy chain CH1 domain and have a hinge region that is not found in other species. The variable region of the Arabian camel (*Camelus dromedarius*) single-domain antibody may have or may include the protein sequence of SEQ ID NO: 10 (GenBank accession number AJ245148). The variable region of the heavy chain of the Arabian camel (*Camelus dromedarius*) tetrameric immunoglobulin may have or may include the protein sequence of SEQ ID NO: 11 (GenBank accession number AJ245184).

In addition to camelids, heavy chain antibodies are also found in cartilaginous fishes, such as sharks, skates and rays. This type of antibody is known as an immunoglobulin new antigen receptor or IgNAR, and the variable domain of an IgNAR is known as the VNAR. The IgNAR exists as two identical heavy chain dimers composed of one variable domain and five constant domains each. Like camelids, there is no light chain.

The protein sequences of additional non-human species may be readily found in online databases, such as the International ImMunoGeneTics Information System (www.imgt.org), the European Bioinformatics Institute (www.ebi.ac.uk), the DNA Databank of Japan (ddbj.nig.ac.jp/arsa) or the National Center for Biotechnology Information (www.ncbi.nlm.nih.gov).

An anti-AGE antibody or a variant thereof may include a heavy chain variable region having at least 90%, 91%, 92%, 93%, 94%, 95%, 96%, 97%, 98%, 99%, or 100% sequence identity to the amino acid sequence of SEQ ID NO: 2 or SEQ ID NO: 20, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

An anti-AGE antibody or a variant thereof may include a light chain variable region having at least 90%, 91%, 92%, 93%, 94%, 95%, 96%, 97%, 98%, 99%, or 100% sequence identity to the amino acid sequence of SEQ ID NO: 4 or SEQ ID NO: 21, including post-translational modifications thereof. A variable region having at least 90%, 91%, 92%, 93%, 94%, 95%, 96%, 97%, 98%, or 99% sequence identity may contain substitutions (e.g., conservative substitutions), insertions, or deletions relative to the reference sequence, but an anti-AGE antibody including that sequence retains the ability to bind to AGE. The substitutions, insertions, or deletions may occur in regions outside the variable region.

Alternatively, the antibody may have the complementarity determining regions of commercially available mouse anti-glycation end-product antibody raised against carboxymethyl lysine conjugated with keyhole limpet hemocyanin (CML-KLH), the carboxymethyl lysine MAb (Clone 318003) available from R&D Systems, Inc. (Minneapolis, Minn.; catalog no. MAB3247).

The antibody may have or may include constant regions which permit destruction of targeted cells by a subject's immune system.

Mixtures of antibodies that bind to more than one type AGE of AGE-modified proteins may also be used.

Bi-specific antibodies, which are anti-AGE antibodies directed to two different epitopes, may also be used. Such antibodies will have a variable region (or complementary determining region) from those of one anti-AGE antibody, and a variable region (or complementary determining region) from a different antibody.

Antibody fragments may be used in place of whole antibodies. For example, immunoglobulin G may be broken down into smaller fragments by digestion with enzymes. Papain digestion cleaves the N-terminal side of inter-heavy chain disulfide bridges to produce Fab fragments. Fab fragments include the light chain and one of the two N-terminal domains of the heavy chain (also known as the Fd fragment). Pepsin digestion cleaves the C-terminal side of the inter-heavy chain disulfide bridges to produce $F(ab')_2$ fragments. $F(ab')_2$ fragments include both light chains and the two N-terminal domains linked by disulfide bridges. Pepsin digestion may also form the Fv (fragment variable) and Fc (fragment crystallizable) fragments. The Fv fragment contains the two N-terminal variable domains. The Fc fragment contains the domains which interact with immunoglobulin receptors on cells and with the initial elements of the complement cascade. Pepsin may also cleave immunoglobulin G before the third constant domain of the heavy chain ($C_H3$) to produce a large fragment F(abc) and a small fragment pFc'. Antibody fragments may alternatively be produced recombinantly.

If additional antibodies are desired, they can be produced using well-known methods. For example, polyclonal antibodies (pAbs) can be raised in a mammalian host by one or more injections of an immunogen, and if desired, an adjuvant. Typically, the immunogen (and adjuvant) is injected in a mammal by a subcutaneous or intraperitoneal injection. The immunogen may be an AGE-modified protein of a cell, such as AGE-antithrombin III, AGE-calmodulin, AGE-insulin, AGE-ceruloplasmin, AGE-collagen, AGE-cathepsin B, AGE-albumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-$Na^+/K^+$-ATPase, AGE-plasminogen, AGE-myelin, AGE-lysozyme, AGE-immunoglobulin, AGE-red cell Glu transport protein, AGE-$\beta$-N-acetyl hexominase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$\beta_2$-microglobulin, AGE-sorbitol dehydrogenase, AGE-$\alpha_1$-antitrypsin, AGE-carbonate dehydratase, AGE-RNAse, AGE-low density lipoprotein, AGE-hexokinase, AGE-apo C-I, AGE-RNAse, AGE-hemoglobin such as AGE-human hemoglobin, AGE-albumin such as AGE-bovine serum albumin (AGE-BSA) and AGE-human serum albumin, AGE-low density lipoprotein (AGE-LDL) and AGE-collagen IV. AGE-modified cells, such as AGE-modified erythrocytes, whole, lysed, or partially digested, may also be used as AGE antigens. Examples of adjuvants include Freund's complete, monophosphoryl Lipid A synthetic-trehalose dicorynomycolate, aluminum hydroxide (alum), heat shock proteins HSP 70 or HSP96, squalene emulsion containing monophosphoryl lipid A, $\alpha$2-macroglobulin and surface active substances, including oil emulsions, pleuronic polyols, polyanions and dinitrophenol. To improve the immune response, an immunogen may be conjugated to a polypeptide that is immunogenic in the host, such as keyhole limpet hemocyanin (KLH), serum albumin, bovine thyroglobulin, cholera toxin, labile enterotoxin, silica particles or soybean trypsin inhibitor. Alternatively, pAbs may be made in chickens, producing IgY molecules.

Monoclonal antibodies (mAbs) may also be made by immunizing a host or lymphocytes from a host, harvesting the mAb-secreting (or potentially secreting) lymphocytes, fusing those lymphocytes to immortalized cells (for example, myeloma cells), and selecting those cells that secrete the desired mAb. Other techniques may be used, such as the EBV-hybridoma technique. Techniques for the generation of chimeric antibodies by splicing genes encoding the variable domains of antibodies to genes of the constant domains of human (or other animal) immunoglobulin result in "chimeric antibodies" that are substantially human (humanized) or substantially "ized" to another animal (such as cat, dog, horse, camel or alpaca, cattle, sheep, or goat) at the amino acid level. If desired, the mAbs may be purified from the culture medium or ascites fluid by conventional procedures, such as protein A-sepharose, hydroxylapatite chromatography, gel electrophoresis, dialysis, ammonium sulfate precipitation or affinity chromatography. Additionally, human monoclonal antibodies can be generated by immunization of transgenic mice containing a third copy IgG human trans-loci and silenced endogenous mouse Ig loci or using human-transgenic mice. Production of humanized monoclonal antibodies and fragments thereof can also be generated through phage display technologies.

A "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include water, saline, Ringer's solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions or dispersions for the extemporaneous preparation of sterile injectable solutions or dispersion. Various excipients may be included in pharmaceutical compositions of antibodies suitable for injection. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin. Sterile injectable solutions can be prepared by incorporating antibodies, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

For administration by inhalation, the antibodies may be delivered as an aerosol spray from a nebulizer or a pressurized container that contains a suitable propellant, for example, a gas such as carbon dioxide. Antibodies may also be delivered via inhalation as a dry powder, for example using the iSPERSE™ inhaled drug delivery platform (PULMATRIX, Lexington, Mass.). The use of anti-AGE antibodies which are chicken antibodies (IgY) may be non-immunogenic in a variety of animals, including humans, when administered by inhalation.

An appropriate dosage level of each type of antibody will generally be about 0.01 to 500 mg per kg patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Although each type of antibody may be administered on a regimen of 1 to 4 times per day, such as once or twice per day, antibodies typically have a long half-life in vivo. Accordingly, each type of antibody may be administered once a day, once a week, once every two or three weeks, once a month, or once every 60 to 90 days.

A subject that receives administration of an anti-AGE antibody may be tested to determine if it has been effective to treat the sarcopenia, by measuring changes in muscle mass over time. For example, a baseline muscle mass in a subject may be measured followed by administration of the anti-AGE antibody. The effectiveness of the treatment may be determined by periodically measuring muscle mass in the subject and comparing the subsequent measurements to the baseline measurement. A subject may be considered to have effective treatment of sarcopenia if he or she does not demonstrate loss of muscle mass between subsequent measurements or over time. Alternatively, the concentration and/or number of senescent cells in fat or muscle tissue may also be monitored. Administration of antibody and subsequent testing may be repeated until the desired therapeutic result is achieved.

Unit dosage forms can be created to facilitate administration and dosage uniformity. Unit dosage form refers to physically discrete units suited as single dosages for the subject to be treated, containing a therapeutically effective quantity of one or more types of antibodies in association with the required pharmaceutical carrier. Preferably, the unit dosage form is in a sealed container and is sterile.

Any mammal that could develop sarcopenia or other diseases or disorders associated with cellular senescence may be treated by the methods herein described. Humans are a preferred mammal for treatment. Other mammals that may be treated include mice, rats, goats, sheep, cows, horses and companion animals, such as dogs or cats. A subject in need of treatment may be identified by the diagnosis of a disease or disorder that is known to cause elevated levels of AGEs such as, for example, diabetes (both Type 1 and Type 2), or the presence of a pathological condition associated with AGEs such as, for example, atherosclerosis, inflammation, retinopathy, nephropathy, stroke, endothelial cell dysfunction, neurodegenerative disorders or cancer. In addition, subjects may be identified for treatment based on their age. For example, a human over 75 years of age may be treated for sarcopenia, while a human under 30 years of age might not be identified as in need of treatment for sarcopenia. Alternatively, any of the mammals or subjects identified above may be excluded from the patient population in need of treatment for sarcopenia.

A subject may be identified as having sarcopenia or in need of treatment if (1) the subject is at least 25 years old and (2) his or her measured muscle mass and measured muscle function are two standard deviations or more below the mean value for healthy 25 year olds of the same gender and no alternative pathology has been identified to account for the reduced muscle mass and reduced muscle function. Preferably, a subject being treated for sarcopenia is at least 40 years old. More preferably, a subject being treated for sarcopenia is at least 50 years old. Most preferably, a subject being treated for sarcopenia is at least 60 years old. Alternatively, a subject may be identified as having sarcopenia or in need of treatment if (1) his or her gait speed is less than 1.0 m/s across a 4 m course and (2) he or she has an objectively measured low muscle mass, such as, for example, an appendicular mass relative to the square of height less than or equal to 7.23 kg/m$^2$ for male subjects or less than or equal to 5.67 kg/m$^2$ for female subjects.

In the case of central nervous system neurodegenerative disorders, it may be preferable to administer a composition containing the anti-AGE antibody directly into the central nervous system. Examples of such administration include intrathecal administration; administration into the ventricular system of the brain (intraventricular administration), for example, through a catheter or a permanent shunt, or other administration device which may be placed during a ventriculostomy (see, for example, Takami, A. et al. "Treatment of primary central nervous system lymphoma with induction of complement-dependent cytotoxicity by intraventricular administration of autologous-serum-supplemented rituximab", *Cancer Sci.* Vol. 97, pp. 80-83 (January 2006)); and administered by convection enhanced delivery (CED) (see, for example, Chen, K. S., et al. "MONOCLONAL ANTIBODY THERAPY FOR MALIGNANT GLIOMA" chapter 10 of *Glioma: lmmunotherapeutic Approaches*, pp. 132-141 (ed. R. Yamanaka; Landes Bioscience and Springer Science+Business Media, 2012)). All such central nervous system administration may optionally also include administration of a serum supplement (such as autologous serum), to enhance the cell killing properties of the AGE antibody; administration of serum supplement may be prior to, simultaneous with, or subsequent to, the administration of the AGE antibody. Optionally, any of the composition containing AGE antibodies described herein may further contain a serum supplement (such as an autologous serum supplement). In place of a serum supplement, or in addition to a serum supplement, purified immune system cells may also be used, either autologous immune system cells, or immune system cells from a donor; examples of such cells include natural killer cells. In addition to, or instead of, the patient's or a donor's natural killer cells, artificial natural killer cells such as those of NANTKWEST®, engineered to bind directly to antibodies, or engineered to bind directly to an AGE antigen (such as carboxymethyllysine) (see www.nantkwest.com).

In the case of cancer, a mammal that could develop metastatic cancer may be treated by the methods herein described. Humans are a preferred mammal for treatment. Other mammals that may be treated include mice, rats, goats, sheep, cows, horses and companion animals, such as dogs or cats. A subject in need of treatment may be identified by the diagnosis of a cancer. Cancers which are particularly subject to metastasis include lung cancer, melanoma, colon cancer, renal cell carcinoma, prostate cancer, cancer of the cervix, bladder cancer, rectal cancer, esophageal cancer, liver cancer, mouth and throat cancer, multiple myeloma, ovarian cancer, and stomach cancer. Treatment may be of patients experiencing metastatic cancer. Treatment may also be administered to patients who have cancer, but prior to any identified metastasis, in order to prevent metastasis. A subject that receives administration of an anti-AGE antibody may be tested to determine if it has been effective to treat the cancer by examining the patient for the spread of the cancer to different parts of the body, particularly in lymph nodes. Administration of antibody and subsequent testing may be repeated until the desired therapeutic result is achieved.

The anti-AGE antibodies may be used in cellular purification processes, such as immunopanning and immunoadsorption. Purification processes are useful in isolating desirable or unwanted cells from tissue cultures, cell cultures or blood. Cellular purification may be used in transplantations, such as a bone marrow transplant, or transfusions, such as a blood transfusion. Cellular purification is especially useful in autologous stem cell transplantation during chemotherapy to remove malignant cells and concentrate beneficial stem cells, such as hematopoietic cells expressing the CD34 protein (CD34$^+$ cells). Immunopanning or immunoadsorption using an anti-AGE antibody may isolate partially-functional or non-functional cells, such as senescent cells, from a tissue culture, cell culture or blood sample. For example, an immunopanning process may involve immobilizing the anti-AGE antibody on a surface, such as a cell culture plate. A tissue culture or cell culture may then be applied to the surface. Any senescent cells present in the tissue culture or cell culture will bind to the anti-AGE antibody, leaving a purified tissue culture or cell culture that is free from senescent cells. Similarly, an immunoadsorption process may involve binding the anti-AGE antibody to senescent cells in a cell culture. The cells may then be passed through a column packed with beads that are coated with a protein that binds to the anti-AGE labeled senescent cells. The cells which pass through the column without binding will be cells that do not express AGE, such as fully-functional cells. An immunoadsorption process may be carried out with a CEPRATE SC Stem Cell Concentration System (CellPro, Inc., Bothell, Wash.) or similar apparatus.

The one-letter amino acid sequence that corresponds to SEQ ID NO: 1 is shown below:

```
            10         20         30         40         50
    MNLLLILTFV AAAVAQVQLL QPGAELVKPG ASVKLACKAS GYLFTTYVVMH 60         70         80         90
    WLKQRPGQGL EWIGEISPTN GRAYYNARFK SEATLTVDKS 100        110        120        130
    SNTAYMQLSS LTSEASAVYY CARAYGNYEF AYWGQGTLVT 140        150        160        170
    VSVASTKGPS VFPLAPSSKS TSGGTAALGC LVKDYFPEPV 180        190        200        210        220
    TVSWNSGALT SGVHTFPAVL QSSGLYSLSS VVTVPSSSLG TQTYICNVNH 230        240        250        260
    KPSNTKVDKK VEPKSCDKTH TCPPCPAPEL LGGPSVFLFP 270        280        290        300
    PKPKDTLMIS RTPEVTCVVV DVSHEDPEVK FNVVYVDGVEV 310        320        330        340
    HNAKTKPREE QYNSTYRVVS VLTVLHQDWL NGKEYKCKVS 350        360        370        380        390
    NKALPAPIEK TISKAKGQPR EPQVYTLPPS REEMTKNQVS LTCLVKGFYP 400        410        420        430
    SDIAVEWESN GQPENNYKTT PPVLDSDGSF FLYSKLTVDK 440        450        460
    SRWQQGNVFS CSVMHEALHN HYTQKSLSLS PGK
```

Positions 16-133 of the above amino acid sequence correspond to SEQ ID NO: 2. Positions 46-50 of the above amino acid sequence correspond to SEQ ID NO: 41. Positions 65-81 of the above amino acid sequence correspond to SEQ ID NO: 42. Positions 114-122 of the above amino acid sequence correspond to SEQ ID NO: 43.

The one-letter amino acid sequence that corresponds to SEQ ID NO: 3 is shown below:

```
            10         20         30         40         50
    MNLLLILTFV AAAVADVVMT QTPLSLPVSL GDQASISCRS RQSLVNSNGN 60         70         80         90        100
    TFLQWYLQKP GQSPKLLIYK VSLRFSGVPD RFSGSGSGTD FTLKISRVEA
```

```
         110        120        130        140        150
EDLGLYFCSQ STHVPPTFGG GTKLEIKRTV AAPSVFIFPP SDEQLKSGTA 160        170        180        190
SVVCLLNNFY PREAKVQWKV DNALQSGNSQ ESVTEQDSKD 200        210        220        230
STYSLSSTLT LSKADYEKHK VYACEVTHQG LSSPVTKSFN RGEC
```

Positions 16-128 of the above amino acid sequence correspond to SEQ ID NO: 4. Optionally, the arginine (Arg or R) residue at position 128 of SEQ ID NO: 4 may be omitted. Positions 39-54 of the above amino acid sequence correspond to SEQ ID NO: 44. Positions 70-76 of the above amino acid sequence correspond to SEQ ID NO: 45. Positions 109-117 of the above amino acid sequence correspond to SEQ ID NO: 46.

The DNA sequence that corresponds to SEQ ID NO: 12 is shown below:

```
ATGGACCCCAAGGGCAGCCTGAGCTGGAGAATCCTGCTGTTCCTGAGC
CTGGCCTTCGAGCTGAGCTACGGCCAGGTGCAGCTGCTGCAGCCAGGT
GCCGAGCTCGTGAAACCTGGCGCCTCTGTGAAGCTGGCCTGCAAGGCT
TCCGGCTACCTGTTCACCACCTACTGGATGCACTGGCTGAAGCAGAGGC
CAGGCCAGGGCCTGGAATGGATCGGCGAGATCTCCCCCACCAACGGCA
GAGCCTACTACAACGCCCGGTTCAAGTCCGAGGCCACCCTGACCGTGG
ACAAGTCCTCCAACACCGCCTACATGCAGCTGTCCTCCCTGACCTCTGA
GGCCTCCGCCGTGTACTACTGCGCCAGAGCTTACGGCAACTACGAGTTC
GCCTACTGGGGCCAGGGCACCCTCGTGACAGTGTCTGTGGCTAAGACC
ACCCCTCCCTCCGTGTACCCTCTGGCTCCTGGCTGTGGCGACACCACCG
GATCCTCTGTGACCCTGGGCTGCCTCGTGAAGGGCTACTTCCCTGAGTC
CGTGACCGTGACCTGGAACTCCGGCTCCCTGTCCTCCTCCGTGCACACC
TTTCCAGCCCTGCTGCAGTCCGGCCTGTACACCATGTCCTCCAGCGTGA
CAGTGCCCTCCTCCACCTGGCCTTCCCAGACCGTGACATGCTCTGTGGC
CCACCCTGCCTCTTCCACCACCGTGGACAAGAAGCTGGAACCCTCCGGC
CCCATCTCCACCATCAACCCTTGCCCTCCCTGCAAAGAATGCCACAAGT
GCCCTGCCCCCAACCTGGAAGGCGGCCCTTCCGTGTTCATCTTCCCACC
CAACATCAAGGACGTGCTGATGATCTCCCTGACCCCCAAAGTGACCTGC
GTGGTGGTGGACGTGTCCGAGGACGACCCTGACGTGCAGATCAGTTGG
TTCGTGAACAACGTGGAAGTGCACACCGCCCAGACCCAGACACACAGAG
AGGACTACAACAGCACCATCAGAGTGGTGTCTACCCTGCCCATCCAGCA
CCAGGACTGGATGTCCGGCAAAGAATTCAAGTGCAAAGTGAACAACAAG
GACCTGCCCAGCCCCATCGAGCGGACCATCTCCAAGATCAAGGGCCTC
GTGCGGGCTCCCCAGGTGTACATTCTGCCTCCACCAGCCGAGCAGCTG
TCCCGGAAGGATGTGTCTCTGACATGTCTGGTCGTGGGCTTCAACCCCG
GCGACATCTCCGTGGAATGGACCTCCAACGGCCACACCGAGGAAAACTA
CAAGGACACCGCCCCTGTGCTGGACTCCGACGGCTCCTACTTCATCTAC
TCCAAGCTGAACATGAAGACCTCCAAGTGGGAAAAGACCGACTCCTTCT
CCTGCAACGTGCGGCACGAGGGCCTGAAGAACTACTACCTGAAGAAAAC
CATCTCCCGGTCCCCCGGCTAG
```

The DNA sequence that corresponds to SEQ ID NO: 13 is shown below:

```
ATGGACCCCAAGGGCAGCCTGAGCTGGAGAATCCTGCTGTTCCTGAGC
CTGGCCTTCGAGCTGAGCTACGGCCAGGTGCAGCTGCTGCAGCCAGGT
GCCGAGCTCGTGAAACCTGGCGCCTCTGTGAAGCTGGCCTGCAAGGCT
TCCGGCTACCTGTTCACCACCTACTGGATGCACTGGCTGAAGCAGAGGC
CAGGCCAGGGCCTGGAATGGATCGGCGAGATCTCCCCCACCAACGGCA
GAGCCTACTACAACGCCCGGTTCAAGTCCGAGGCCACCCTGACCGTGG
ACAAGTCCTCCAACACCGCCTACATGCAGCTGTCCTCCCTGACCTCTGA
GGCCTCCGCCGTGTACTACTGCGCCAGAGCTTACGGCAACTACGAGTTC
GCCTACTGGGGCCAGGGCACCCTCGTGACAGTGTCTGTGGCTAGCACC
AAGGGCCCCAGCGTGTTCCCTCTGGCCCCCAGCAGCAAGAGCACCAGC
GGCGGAACCGCCGCCCTGGGCTGCCTGGTGAAGGACTACTTCCCCGAG
CCCGTGACCGTGTCCTGGAACAGCGGCGCTCTGACCAGCGGAGTGCAC
ACCTTCCCTGCCGTGCTGCAGAGCAGCGGCCTGTACTCCCTGAGCAGC
GTGGTGACCGTGCCCAGCAGCAGCCTGGGCACCCAGACCTACATCTGC
AACGTGAACCACAAGCCCTCCAACACCAAGGTGGACAAGAAGGTGGAG
CCTAAGAGCTGCGACAAGACCCACACCTGCCCTCCCTGCCCCGCCCCC
GAGCTGCTGGGCGGACCCAGCGTGTTCCTGTTCCCTCCCAAGCCCAAG
GACACCCTGATGATCAGCCGCACCCCCGAGGTGACCTGCGTGGTGGTG
GACGTGAGCCACGAGGACCCCGAGGTGAAGTTCAACTGGTACGTGGAC
GGCGTGGAGGTGCACAACGCCAAGACCAAGCCTCGGGAGGAGCAGTAC
AACTCCACCTACCGCGTGGTGAGCGTGCTGACCGTGCTGCACCAGGAC
TGGCTGAACGGCAAGGAGTACAAGTGCAAGGTGAGCAACAAGGCCCTG
CCCGCTCCCATCGAGAAGACCATCAGCAAGGCCAAGGGCCAGCCCCGG
GAGCCTCAGGTGTACACCCTGCCCCCCAGCCGCGACGAGCTGACCAAG
AACCAGGTGAGCCTGACCTGCCIGGTGAAGGGCTTCTACCCCTCCGACA
TCGCCGTGGAGTGGGAGAGCAACGGCCAGCCTGAGAACAACTACAAGA
CCACCCCTCCCGTGCTGGACAGCGACGGCAGCTTCTTCCTGTACAGCAA
GCTGACCGTGGACAAGTCCCGGTGGCAGCAGGGCAACGTGTTCAGCTG
CAGCGTGATGCACGAGGCCCTGCACAACCACTACACCCAGAAGAGCCT
GAGCCTGAGCCCCGGATAG
```

The DNA sequence that corresponds to SEQ ID NO: 14 is shown below:

ATGGAGACCGACACCCTGCTGCTCTGGGTGCTGCTGCTCTGGGTGCCC
GGCTCCACCGGAGACGTCGTGATGACCCAGACCCCTCTGTCCCTGCCT
GTGTCTCTGGGCGACCAGGCCTCCATCTCCTGCCGGTCTAGACAGTCCC
TCGTGAACTCCAACGGCAACACCTTCCTGCAGTGGTATCTGCAGAAGCC
CGGCCAGTCCCCCAAGCTGCTGATCTACAAGGTGTCCCTGCGGTTCTCC
GGCGTGCCCGACAGATTTTCCGGCTCTGGCTCTGGCACCGACTTCACCC
TGAAGATCTCCCGGGTGGAAGCCGAGGACCTGGGCCTGTACTTCTGCA
GCCAGTCCACCCACGTGCCCCCTACATTTGGCGGAGGCACCAAGCTGG
AAATCAAACGGGCAGATGCTGCACCAACTGTATCCATCTTCCCACCATCC
AGTGAGCAGTTAACATCTGGAGGTGCCTCAGTCGTGTGCTTCTTGAACA
ACTTCTACCCCAAAGACATCAATGTCAAGTGGAAGATTGATGGCAGTGAA
CGACAAAATGGCGTCCTGAACAGTTGGACTGATCAGGACAGCAAAGACA
GCACCTACAGCATGAGCAGCACCCTCACGTTGACCAAGGACGAGTATGA
ACGACATAACAGCTATACCTGTGAGGCCACTCACAAGACATCAACTTCAC
CCATTGTCAAGAGCTTCAACAGGAATGAGTGTTGA

The DNA sequence that corresponds to SEQ ID NO: 15 is shown below:

ATGGAGACCGACACCCTGCTGCTCTGGGTGCTGCTGCTCTGGGTGCCC
GGCTCCACCGGAGACGTCGTGATGACCCAGACCCCTCTGTCCCTGCCT
GTGTCTCTGGGCGACCAGGCCTCCATCTCCTGCCGGTCTAGACAGTCCC
TCGTGAACTCCAACGGCAACACCTTCCTGCAGTGGTATCTGCAGAAGCC
CGGCCAGTCCCCCAAGCTGCTGATCTACAAGGTGTCCCTGCGGTTCTCC
GGCGTGCCCGACAGATTTTCCGGCTCTGGCTCTGGCACCGACTTCACCC
TGAAGATCTCCCGGGTGGAAGCCGAGGACCTGGGCCTGTACTTCTGCA
GCCAGTCCACCCACGTGCCCCCTACATTTGGCGGAGGCACCAAGCTGG
AAATCAAGCGGACCGTGGCCGCCCCCAGCGTGTTCATCTTCCCTCCCAG
CGACGAGCAGCTGAAGTCTGGCACCGCCAGCGTGGTGTGCCTGCTGAA
CAACTTCTACCCCGCGAGGCCAAGGTGCAGTGGAAGGTGGACAACGC
CCTGCAGAGCGGCAACAGCCAGGAGAGCGTGACCGAGCAGGACTCCAA
GGACAGCACCTACAGCCTGAGCAGCACCCTGACCCTGAGCAAGGCCGA
CTACGAGAAGCACAAGGTGTACGCCTGCGAGGTGACCCACCAGGGACT
GTCTAGCCCCGTGACCAAGAGCTTCAACCGGGGCGAGTGCTAA

The one-letter amino acid sequence that corresponds to SEQ ID NO: 16 is shown below:

MDPKGSLSWRILLFLSLAFELSYGQVQLLQPGAELVKPGASVKLACKASG
YLFTTYVVMHWLKQRPGQGLEWIGEISPINGRAYYNARFKSEATLTVDKS
SNTAYMQLSSLTSEASAVYYCARAYGNYEFAYWGQGTLVTVSVAKTIPPS
VYPLAPGCGDTTGSSVTLGCLVKGYFPESVIVTWNSGSLSSSVHTFPALL

QSGLYTMSSSVTVPSSTWPSQTVTCSVAHPASSTIVDKKLEPSGPISTIN
PCPPCKECHKCPAPNLEGGPSVFIFPPNIKDVLMISLTPKVTCVVVDSE
DDPDVQISVVFVNNVEVHTAQTQTHREDYNSTIRVVSTLPIQHQDWMSGK
EFKCKVNNKDLPSPIERTISKIKGLVRAPQVYILPPPAEQLSRKDVSLTC
LVVGFNPGDISVEVVTSNGHTEENYKDTAPVLDSDGSYFIYSKLNMKTSK
WEKTDSFSCNVRHEGLKNYYLKKTISRSPG*

The shaded region of the above amino acid sequence corresponds to SEQ ID NO: 20.

The one-letter amino acid sequence that corresponds to SEQ ID NO: 17 is shown below:

MDPKGSLSWRILLFLSLAFELSYGQVQLLQPGAELVKPGASVKLACKASG
YLFTTYWMHWLKQRPGQGLEWIGEISPTNGRAYYNARFKSEATLTVDKSS
NTAYMQLSSLTSEASAVYYCARAYGNYEFAYWGQGTLVTVSVASTKGPSV
FPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHT
CPPCPAPELLGGPSVFLFPPKPKDILMISRTPEVTCVVVDVSHEDPEVKF
NWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSC
SVMHEALHNHYTQKSLSLSPG*

The one-letter amino acid sequence that corresponds to SEQ ID NO: 18 is shown below:

METDTLLLWVLLLWVPGSTGDVVMTQTPLSLPVSLGDQASISCRSRQSLV
NSNGNTFLQWYLQKPGQSPKLLIYKVSLRFSGVPDRFSGSGSGTDFTLKI
SRVEAEDLGLYFCSQSTHVPPTFGGGTKLEIKRADAAPTVSIFPPSSEQL
TSGGASVVCFLNNFYPKDINVKWKIDGSERQNGVLNSWTDQDSKDSTYSM
SSTLTLTKDEYERHNSYTCEATHKTSTSPIVKSFNRNEC*

The shaded region of the above amino acid sequence corresponds to SEQ ID NO: 21.

The one-letter amino acid sequence that corresponds to SEQ ID NO: 19 is shown below:

METDTLLLWVLLLWVPGSTGDVVMTQTPLSLPVSLGDQASISCRSRQSLV
NSNGNTFLQWYLQKPGQSPKLLIYKVSLRFSGVPDRFSGSGSGTDFTLKI
SRVEAEDLGLYFCSQSTHVPPTFGGGTKLEIKRTVAAPSVFIFPPSDEQL
KSGTASVVCLLNNFYPREAKVQWKVDNALQSGNSQESVTEQDSKDSTYSL
SSTLTLSKADYEKHKVYACEVTHQGLSSPVTKSFNRGEC*

The one-letter amino acid sequence that corresponds to SEQ ID NO: 22 is shown below:

```
             10         20         30         40
      ASTKGPSVFP LAPCSRSTSE STAALGCLVK DYFPEPVTVS
             50         60         70         80
      WNSGALTSGV HTFPAVLQSS GLYSLSSVVT VPSSNFGTQT
```

```
            90        100       110        120
YTCNVDHKPS NTKVDKTVER KCCVECPPCP APPVAGPSVF 130        140       150        160
LFPPKPKDTL MISRTPEVTC VVVDVSHEDP EVQFNWYVDG 170        180       190        200
VEVHNAKTKP REEQFNSTFR VVSVLTVVHQ DWLNGKEYKC 210        220       230        240
KVSNKGLPAP IEKTISKTKG QPREPQVYTL PPSREEMTKN 250        260       270        280
QVSLTCLVKG FYPSDISVEW ESNGQPENNY KTTPPMLDSD 290        300       310        320
GSFFLYSKLT VDKSRWQQGN VFSCSVMHEA LHNHYTQKSL SLSPGK
```

The one-letter amino acid sequence that corresponds to SEQ ID NO: 23 is SYTMGVS.

The one-letter amino acid sequence that corresponds to SEQ ID NO: 24 is TISSGGGSTYYPDSVKG.

The one-letter amino acid sequence that corresponds to SEQ ID NO: 25 is QGGWLPPFAX, where X may be any naturally occurring amino acid.

The one-letter amino acid sequence that corresponds to SEQ ID NO: 26 is RASKSVSTSSRGYSYMH.

The one-letter amino acid sequence that corresponds to SEQ ID NO: 27 is LVSNLES.

The one-letter amino acid sequence that corresponds to SEQ ID NO: 28 is QHIRELTRS.

The one-letter amino acid sequence that corresponds to SEQ ID NO: 29 is

MDPKGSLSWRILLFLSLAFELSYGQVQLVQSGAEVKKPGASVKVSCKASG
YLFTTYWMHWVRQAPGQGLEWMGEISPTNGRAYYNQKFQGRVTMTVDKST
NTVYMELSSLRSEDTAVYYCARAYGNYFAYWGQGTLVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELKNQVSLTCLVKGFYPSDIA
VEWESNGQPENNYKTTPPVLDSDGSFFLYSKLTVDKSRWQQGNVFSCSVM
HEALHNHYTQKSLSLSPG.

The DNA sequence that corresponds to SEQ ID NO: 30 is

ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA
CAACAGAAATTCCAGGGCAGAGTGACCATGACCGTGGACAAGTCCACCAA
CACCGTGTACATGGAACTGTCCTCCCTGCGGAGCGAGGACACCGCCGTGT
ACTACTGCGCTAGAGCCTACGGCAACTACGATTCGCCTACTGGGGCCAGG
GCACCCTCGTGACAGTGTCCTCTGCTAGCACCAAGGGCCCCAGCGTGTTC
CCTCTGGCCCCCAGCAGCAAGAGCACCAGCGGCGGAACCGCCGCCCTGGG
CTGCCTGGGAAGGACTACTTCCCCGAGCCCGTGACCGTGTCCTGGAACAG
CGGCGCTCTGACCAGCGGAGTGCACACCTTCCCTGCCGTGCTGCAGAGCA
GCGGCCTGTACTCCCTGAGCAGCGTGGTGACCGTGCCAGCAGCAGCCTGG
GCACCCAGACCTACATCTGCAACGTGAACCACAAGCCCTCCAACACCAAG
GTGGACAAGAAGGTGGAGCCTAAGAGCTGCGACAAGACCCACACCTGCCC
TCCCTGCCCCGCCCCGAGCTGCTGGGCGGACCCAGCGTGTTCCTGTTCCC
TCCCAAGCCCAAGGACACCCTGATGATCAGCCGCACCCCCGAGGTGACCT
GCGTGGTGGTGGACGTGAGCCACGAGGACCCCGAGGTGAGTTCAACTGGT
ACGTGGACGGCGTGGAGGTGCACAACGCCAAGACCAAGCCTCGGGAGGAG
CAGTACAACTCCACCTACCGCGTGGTGAGCGTGCTGACCGTGCTGCACCA
GGACTGGCTGAACGGCAGGAGTACAAGTGCAAGGTGAGCAACAAGGCCCT
GCCCGCTCCCATCGAGAAGACCATCAGCAAGGCCAAGGGCCAGCCCCGGG
AGCCTCAGGTGTACACCCTGCCCCCAGCCGCGACGAGCTGACAAGAACC
AGGTGAGCCTGACCTGCCTGGTGAAGGGCTTCTACCCCTCCGACATCGCC
GTGGAGTGGGAGAGCAACGGCCAGCCTGAGAACAACTACAAGACCACCCC
TCCCGTGCTGGACAGCGACGCAGCTTCTTCCTGTACAGCAAGCTGACCGT
GGACAAGTCCCGGTGGCAGCAGGGCAACGTGTTCAGCTGCAGCGTGATGC
ACGAGGCCCTGCACAACCACTACACCCAGAAGAGCCTGAGCCTGAGCCCG
GATAGTAA.

The one-letter amino acid sequence that corresponds to SEQ ID NO: 31 is

MDPKGSLSWRILLFLSLAFELSYGQVQLVQSGAEVKKPGASVKVSCKASG
YLFTTYWMHWVRQAPGQGLEWMGEISPTNGRAYYNAKFQGRVTMTVDKST
NTAYMELSSLRSEDTAVYYCARAYGNYFAYWGQGTLVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELKNQVSLTCLVKGFYPSDIA
VEWESNGQPENNYKTTPPVLDSDGSFFLYSKLTVDKSRWQQGNVFSCSVM
HEALHNHYTQKSLSLSPG.

The DNA sequence that corresponds to SEQ ID NO: 32 is

ATGGACCCCAAGGGCAGCCTGAGCTGGAGAATCCTGCTGTTCCTGAGCCT
GGCCTTCGAGCTGAGCTACGGCCAGGTGCAGCTGGTGCAGTCTGGCGCCG
AAGTGAAGAAACCTGGCGCCTCCGTGAGGTGTCCTGCAAGGCTTCCGGCT
ACCTGTTCACCACCTACTGGATGCACTGGGTGCGACAGGCCCCTGGACAG
GGCCTGGAATGGATGGGCGAGATCTCCCCTACCAACGGCAGAGCCTACTA

-continued

CAACCAAAATTCCAGGGCAGAGTGACCATGACCGTGGACAAGTCCACCAA

CACCGCTTACATGGAACTGTCCTCCCTGCGGAGCGAGGACACCGCCGTGT

ACTACTGCGCTAGAGCCTACGGCAACTACGATTCGCCTACTGGGGCCAGG

GCACCCTCGTGACAGTGTCCTCTGCTAGCACCAAGGGCCCCAGCGTGTTC

CCTCTGGCCCCCAGCAGCAAGAGCACCAGCGGCGGAACCGCCGCCCTGGG

CTGCCTGGGAAGGACTACTTCCCCGAGCCCGTGACCGTGTCCTGGAACAG

CGGCGCTCTGACCAGCGGAGTGCACACCTTCCCTGCCGTGCTGCAGAGCA

GCGGCCTGTACTCCCTGAGCAGCGTGGTGACCGTGCCAGCAGCAGCCTGG

GCACCCAGACCTACATCTGCAACGTGAACCACAAGCCCTCCAACACCAAG

GTGGACAAGAAGGTGGAGCCTAAGAGCTGCGACAAGACCCACACCTGCCC

TCCCTGCCCCGCCCCGAGCTGCTGGGCGGACCCAGCGTGTTCCTGTTCCC

TCCCAAGCCCAAGGACACCCTGATGATCAGCCGCACCCCCGAGGTGACCT

GCGTGGTGGTGGACGTGAGCCACGAGGACCCCGAGGTGAGTTCAACTGGT

ACGTGGACGGCGTGGAGGTGCACAACGCCAAGACCAAGCCTCGGGAGGAG

CAGTACAACTCCACCTACCGCGTGGTGAGCGTGCTGACCGTGCTGCACCA

GGACTGGCTGAACGGCAGGAGTACAAGTGCAAGGTGAGCAACAAGGCCCT

GCCCGCTCCCATCGAGAAGACCATCAGCAAGGCCAAGGGCCAGCCCCGGG

AGCCTCAGGTGTACACCCTGCCCCCCAGCCGCGACGAGCTGACAAGAACC

AGGTGAGCCTGACCTGCCTGGTGAAGGGCTTCTACCCCTCCGACATCGCC

GTGGAGTGGGAGAGCAACGGCCAGCCTGAGAACAACTACAAGACCACCCC

TCCCGTGCTGGACAGCGACGCAGCTTCTTCCTGTACAGCAAGCTGACCGT

GGACAAGTCCCGGTGGCAGCAGGGCAACGTGTTCAGCTGCAGCGTGATGC

ACGAGGCCCTGCACAACCACTACACCCAGAAGAGCCTGAGCCTGAGCCCG

GATAGTAA.

The one-letter amino acid sequence that corresponds to SEQ ID NO: 33 is

MDPKGSLSWRILLFLSLAFELSYGQVQLVQSGAEVKKPGASVKVSCKASG

YLFTTYWMHWVRQAPGQGLEWMGEISPTNGRAYYNAKFQGRVTMTVDKSI

NTAYMELSRLRSDDTAVYYCARAYGNYFAYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELKNQVSLTCLVKGFYPSDIA

VEWESNGQPENNYKTTPPVLDSDGSFFLYSKLTVDKSRWQQGNVFSCSVM

HEALHNHYTQKSLSLSPG.

The DNA sequence that corresponds to SEQ ID NO: 34 is

ATGGACCCCAAGGGCAGCCTGAGCTGGAGAATCCTGCTGTTCCTGAGCCT

GGCCTTCGAGCTGAGCTACGGCCAGGTGCAGCTGGTGCAGTCTGGCGCCG

AAGTGAAGAAACCTGGCGCCTCCGTGAGGTGTCCTGCAAGGCTTCCGGCT

ACCTGTTCACCACCTACTGGATGCACTGGGTGCGACAGGCCCCTGGACAG

GGCCTGGAATGGATGGGCGAGATCTCCCCTACCAACGGCAGAGCCTACTA

CAACCAAAATTCCAGGGCAGAGTGACCATGACCGTGGACAAGTCCATCAA

CACCGCTTACATGGAACTGTCCAGACTGCGGAGCGATGACACCGCCGTGT

ACTACTGCGCTAGAGCCTACGGCAACTACGATTCGCCTACTGGGGCCAGG

GCACCCTCGTGACAGTGTCCTCTGCTAGCACCAAGGGCCCCAGCGTGTTC

CCTCTGGCCCCCAGCAGCAAGAGCACCAGCGGCGGAACCGCCGCCCTGGG

CTGCCTGGGAAGGACTACTTCCCCGAGCCCGTGACCGTGTCCTGGAACAG

CGGCGCTCTGACCAGCGGAGTGCACACCTTCCCTGCCGTGCTGCAGAGCA

GCGGCCTGTACTCCCTGAGCAGCGTGGTGACCGTGCCAGCAGCAGCCTGG

GCACCCAGACCTACATCTGCAACGTGAACCACAAGCCCTCCAACACCAAG

GTGGACAAGAAGGTGGAGCCTAAGAGCTGCGACAAGACCCACACCTGCCC

TCCCTGCCCCGCCCCGAGCTGCTGGGCGGACCCAGCGTGTTCCTGTTCCC

TCCCAAGCCCAAGGACACCCTGATGATCAGCCGCACCCCCGAGGTGACCT

GCGTGGTGGTGGACGTGAGCCACGAGGACCCCGAGGTGAGTTCAACTGGT

ACGTGGACGGCGTGGAGGTGCACAACGCCAAGACCAAGCCTCGGGAGGAG

CAGTACAACTCCACCTACCGCGTGGTGAGCGTGCTGACCGTGCTGCACCA

GGACTGGCTGAACGGCAGGAGTACAAGTGCAAGGTGAGCAACAAGGCCCT

GCCCGCTCCCATCGAGAAGACCATCAGCAAGGCCAAGGGCCAGCCCCGGG

AGCCTCAGGTGTACACCCTGCCCCCCAGCCGCGACGAGCTGACAAGAACC

AGGTGAGCCTGACCTGCCTGGTGAAGGGCTTCTACCCCTCCGACATCGCC

GTGGAGTGGGAGAGCAACGGCCAGCCTGAGAACAACTACAAGACCACCCC

TCCCGTGCTGGACAGCGACGCAGCTTCTTCCTGTACAGCAAGCTGACCGT

GGACAAGTCCCGGTGGCAGCAGGGCAACGTGTTCAGCTGCAGCGTGATGC

ACGAGGCCCTGCACAACCACTACACCCAGAAGAGCCTGAGCCTGAGCCCG

GATAGTAA.

The one-letter amino acid sequence that corresponds to SEQ ID NO: 35 is

METDTLLLWVLLLWVPGSTGDVVMTQSPLSLPVTLGQPASISCRSSQSLV

NSNGNTFLQWYQQRPGQSPRLLIYKVSLRFSGVPDRFSGSGSGTDFTLKI

SRVEAEDVGVYYCSQSTHVPPTFGGGTVEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC.

The DNA sequence that corresponds to SEQ ID NO: 36 is

ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCTCCCAGTCCCTCGTGA

```
ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.
```

The one-letter amino acid sequence that corresponds to SEQ ID NO: 37 is

```
METDTLLLWVLLLWVPGSTGDVVMTQSPLSLPVTLGQPASISCRSRQSLV

NSNGNTFLQWYQQRPGQSPRLLIYKVSLRFSGVPDRFSGSGSGTDFTLKI

SRVEAEDVGVYYCSQSTHVPPTFGGGTVEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC.
```

The DNA sequence that corresponds to SEQ ID NO: 38 is

```
ATGGAGACCGACACCCTGCTGCTCTGGGTGCTGCTGCTCTGGGTGCCCGG

CTCCACCGGAGACGTCGTGATGACCCAGTCCCCTCTGTCCCTGCCTGTGA

CCCTGGGACAGCCTGCCTCCATCTCCTCAGATCCAGGCAGTCCCTCGTGA

ACTCCAACGGCAACACCTTCCTGCAGTGGTATCAGCAGCGGCCTGGCCAG

AGCCCCAGACTGCTGATCTACAAGGTGTCCCTGCGGTTCTCCGGCGTGCC

CGACGATTTTCCGGCTCTGGCTCTGGCACCGACTTCACCCTGAAGATCTC

CCGGGTGGAAGCCGAGGACGTGGGCGTGTACTACTGCTCCCAGAGCACCC

ACGTGCCCCCTACATTTGGCGGAGGCACCAAGTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.
```

The one-letter amino acid sequence that corresponds to SEQ ID NO: 39 is

```
METDTLLLWVLLLWVPGSTGDVVMTQSPLSSPVTLGQPASISCRSSQSLV

NSNGNTFLQWYHQRPGQPPRLLIYKVSLRFSGVPDRFSGSGAGKDFTLKI

SRVEAEDVGVYYCSQSTHVPPTFGQGTLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC.
```

The DNA sequence that corresponds to SEQ ID NO: 40 is

```
ATGGAGACCGACACCCTGCTGCTCTGGGTGCTGCTGCTCTGGGTGCCCGG

CTCCACCGGAGACGTCGTGATGACCCAGTCCCCTCTGTCCAGTCCTGTGA

CCCTGGGACAGCCTGCCTCCATCTCCTCAGATCCTCCCAGTCCCTCGTGA

ACTCCAACGGCAACACCTTCCTGCAGTGGTATCACCAGCGGCCTGGCCAG

CCTCCCAGACTGCTGATCTACAAGGTGTCCCTGCGGTTCTCCGGCGTGCC

CGACGATTTTCCGGCTCTGGCGCTGGCAAGGACTTCACCCTGAAGATCTC

CCGGGTGGAAGCCGAGGACGTGGGCGTGTACTACTGCTCCCAGAGCACCC

ACGTGCCCCCTACATTTGGCCAGGGCACCAACTGGAAATCAAGCGGACCG

TGGCCGCCCCCAGCGTGTTCATCTTCCCTCCCAGCGACGAGCAGCTGAAG

TCTGGCACCGCCAGCGTGGTGTGCCTGCTGAACAACTTCTACCCCCGCGA

GGCCAAGGGCAGTGGAAGGTGGACAACGCCCTGCAGAGCGGCAACAGCCA

GGAGAGCGTGACCGAGCAGGACTCCAAGGACAGCACCTACAGCCTGAGCA

GCACCCTGACCCTGAGCAAGGCCGACTACGAGAAGACAAGGTGTACGCCT

GCGAGGTGACCCACCAGGGACTGTCTAGCCCCGTGACCAAGAGCTTCAAC

CGGGGCGAGTGCTAA.
```

EXAMPLES

Example 1: In Vivo Study of the Administration of Anti-Glycation End-Product Antibody To examine the effects of an anti-glycation end-product antibody, the antibody was administered to the aged CD1 (ICR) mouse (Charles River Laboratories), twice daily by intravenous injection, once a week, for three weeks (Days 1, 8 and 15), followed by a 10 week treatment-free period. The test antibody was a commercially available mouse anti-glycation end-product antibody raised against carboxymethyl lysine conjugated with keyhole limpet hemocyanin, the carboxymethyl lysine MAb (Clone 318003) available from R&D Systems, Inc. (Minneapolis, Minn.; catalog no. MAB3247). A control reference of physiological saline was used in the control animals.

Mice referred to as "young" were 8 weeks old, while mice referred to as "old" were 88 weeks (±2 days) old. No adverse events were noted from the administration of the antibody. The different groups of animals used in the study are shown in Table 1.

TABLE 1

The different groups of animals used in the study

| Group No. | Test Material | Mice | Dose Level (μg/gm/ BID/week) | Number of Animals Main Study Females | Treatment-Free Females |
|---|---|---|---|---|---|
| 1 | Saline | young | 0 | 20 | — |
| 2 | Saline | old | 0 | 20 | 20 |
| 3 | Antibody | old | 2.5 | 20 | 20 |
| 4 | None | old | 0 | 20 | pre |
| 5 | Antibody | old | 5.0 | 20 | 20 |

— = Not Applicable, Pre = Subset of animals euthanized prior to treatment start for collection of adipose tissue.

$P16^{Ink4a}$ mRNA, a marker for senescent cells, was quantified in adipose tissue of the groups by Real Time-qPCR. The results are shown in Table 2. In the table $\Delta\Delta Ct = \Delta Ct$ mean control Group (2) $-\Delta Ct$ mean experimental Group (1 or 3 or 5); Fold Expression = $2^{-\Delta\Delta Ct}$.

TABLE 2

$P16^{INK4a}$ mRNA quantified in adipose tissue

| Calculation | Group 2 vs Group 1 | | Group 2 vs Group 3 | | Group 2 vs Group 5 | |
|---|---|---|---|---|---|---|
| (unadjusted to Group 4: 5.59) | Group 2 | Group 1 | Group 2 | Group 3 | Group 2 | Group 5 |
| Mean ΔCt | 5.79 | 7.14 | 5.79 | 6.09 | 5.79 | 7.39 |
| ΔΔCt | −1.35 | | −0.30 | | −1.60 | |
| Fold Expression | 2.55 | | 1.23 | | 3.03 | |

The table above indicates that untreated old mice (Control Group 2) express 2.55-fold more $p16^{Ink4a}$ mRNA than the untreated young mice (Control Group 1), as expected. This was observed when comparing Group 2 untreated old mice euthanized at end of recovery Day 85 to Group 1 untreated young mice euthanized at end of treatment Day 22. When results from Group 2 untreated old mice were compared to results from Group 3 treated old mice euthanized Day 85, it was observed that $p16^{Ink4a}$ mRNA was 1.23-fold higher in Group 2 than in Group 3. Therefore, the level of $p16^{Ink4a}$ mRNA expression was lower when the old mice were treated with 2.5 μg/gram/BID/week of antibody.

When results from Group 2 (Control) untreated old mice were compared to results from Group 5 (5 μg/gram) treated old mice euthanized Day 22, it was observed that $p16^{Ink4a}$ mRNA was 3.03-fold higher in Group 2 (controls) than in Group 5 (5 μg/gram). This comparison indicated that the Group 5 animals had lower levels of $p16^{Ink4a}$ mRNA expression when they were treated with 5.0 μg/gram/BID/week, providing $p16^{Ink4a}$ mRNA expression levels comparable to that of the young untreated mice (i.e. Group 1). Unlike Group 3 (2.5 μg/gram) mice that were euthanized at end of recovery Day 85, Group 5 mice were euthanized at end of treatment Day 22.

These results indicate the antibody administration resulted in the killing of senescent cells.

The mass of the gastrocnemius muscle was also measured, to determine the effect of antibody administration on sarcopenia. The results are provided in Table 3. The results indicate that administration of the antibody increased muscle mass as compared to controls, but only at the higher dosage of 5.0 μg/gm/BID/week.

TABLE 3

Effect of antibody administration on mass of the gastrocnemius muscle

| Group | Summary Information | Absolute weight of Gastrocnemius Muscle | Weight relative to body mass of Gastrocnemius Muscle |
|---|---|---|---|
| 1 | Mean | 0.3291 | 1.1037 |
|   | SD | 0.0412 | 0.1473 |
|   | N | 20 | 20 |
| 2 | Mean | 0.3304 | 0.7671 |
|   | SD | 0.0371 | 0.1246 |
|   | N | 20 | 20 |
| 3 | Mean | 0.3410 | 0.7706 |
|   | SD | 0.0439 | 0.0971 |
|   | N | 19 | 19 |
| 5 | Mean | 0.4074 | 0.9480 |
|   | SD | 0.0508 | 0.2049 |
|   | N | 9 | 9 |

Example 2: Affinity and Kinetics of Test Antibody

The affinity and kinetics of the test antibody used in Example 1 were analyzed using Nα,Nα-bis(carboxymethyl)-L-lysine trifluoroacetate salt (Sigma-Aldrich, St. Louis, Mo.) as a model substrate for an AGE-modified protein of a cell. Label-free interaction analysis was carried out on a BIACORE™ T200 (GE Healthcare, Pittsburgh, Pa.), using a Series S sensor chip CM5 (GE Healthcare, Pittsburgh, Pa.), with Fc1 set as blank, and Fc2 immobilized with the test antibody (molecular weigh of 150,000 Da). The running buffer was a HBS-EP buffer (10 mM HEPES, 150 mM NaCl, 3 mM EDTA and 0.05% P-20, pH of 7.4), at a temperature of 25° C. Software was BIACORE™ T200 evaluation software, version 2.0. A double reference (Fc2-1 and only buffer injection), was used in the analysis, and the data was fitted to a Langmuir 1:1 binding model.

TABLE 4

Experimental set-up of affinity and kinetics analysis
Association and dissociation

| | |
|---|---|
| Flow path | Fc1 and Fc2 |
| Flow rate (μl/min.) | 30 |
| Association time (s) | 300 |
| Dissociation time (s) | 300 |
| Sample concentration (μM) | 20 − 5 − 1.25 (×2) − 0.3125 − 0.078 − 0 |

A graph of the response versus time is illustrated in FIG. 1. The following values were determined from the analysis: $k_a$ (1/Ms)=1.857×10$^3$; $k_d$ (1/s)=6.781×10$^{-3}$; $K_D$ (M)=3.651× 10$^{-6}$; $R_{max}$ (RU)=19.52; and Chi$^2$=0.114. Because the Chi$^2$ value of the fitting is less than 10% of $R_{max}$, the fit is reliable.

Example 3: Construction and Production of Murine Anti-AGE IgG2b Antibody and Chimeric Anti-AGE IgG1 Antibody Murine and chimeric human anti-AGE antibodies were prepared. The DNA sequence of murine anti-AGE antibody IgG2b heavy chain is shown in SEQ ID NO: 12. The DNA sequence of chimeric human anti-AGE antibody IgG1 heavy chain is shown in SEQ ID NO: 13. The DNA sequence of murine anti-AGE antibody kappa light chain is shown in SEQ ID NO: 14. The DNA sequence of chimeric human anti-AGE antibody kappa light chain is shown in SEQ ID NO: 15. The gene sequences were synthesized and cloned into high expression mammalian vectors. The sequences were codon optimized. Completed constructs were sequence confirmed before proceeding to transfection.

HEK293 cells were seeded in a shake flask one day before transfection, and were grown using serum-free chemically defined media. The DNA expression constructs were transiently transfected into 0.03 liters of suspension HEK293 cells. After 20 hours, cells were sampled to obtain the viabilities and viable cell counts, and titers were measured (Octet QKe, ForteBio). Additional readings were taken throughout the transient transfection production runs. The cultures were harvested on day 5, and an additional sample for each was measured for cell density, viability and titer.

The conditioned media for murine and chimeric anti-AGE antibodies were harvested and clarified from the transient transfection production runs by centrifugation and filtration. The supernatants were run over a Protein A column and eluted with a low pH buffer. Filtration using a 0.2 μm membrane filter was performed before aliquoting. After purification and filtration, the protein concentrations were calculated from the OD280 and the extinction coefficient. A summary of yields and aliquots is shown in Table 5:

TABLE 5

Yields and aliquots

| Protein | Concentration (mg/mL) | Volume (mL) | No. of vials | Total Yield (mg) |
|---|---|---|---|---|
| Murine anti-AGE | 0.08 | 1.00 | 3 | 0.24 |
| Chimeric anti-AGE | 0.23 | 1.00 | 3 | 0.69 |

Antibody purity was evaluated by capillary electrophoresis sodium-dodecyl sulfate (CE-SDS) analysis using LabChip® GXII, (PerkinElmer).

Example 4: Binding of Murine (Parental) and Chimeric Anti-AGE Antibodies

The binding of the murine (parental) and chimeric anti-AGE antibodies described in Example 3 was investigated by a direct binding ELISA. An anti-carboxymethyl lysine (CML) antibody (R&D Systems, MAB3247) was used as a control. CML was conjugated to KLH (CML-KLH) and both CML and CML-KLH were coated overnight onto an ELISA plate. HRP-goat anti-mouse Fc was used to detect the control and murine (parental) anti-AGE antibodies. HRP-goat anti-human Fc was used to detect the chimeric anti-AGE antibody.

The antigens were diluted to 1 μg/mL in 1× phosphate buffer at pH 6.5. A 96-well microtiter ELISA plate was coated with 100 μL/well of the diluted antigen and let sit at 4° C. overnight. The plate was blocked with 1×PBS, 2.5% BSA and allowed to sit for 1-2 hours the next morning at room temperature. The antibody samples were prepared in serial dilutions with 1×PBS, 1% BSA with the starting concentration of 50 μg/mL. Secondary antibodies were diluted 1:5,000. 100 μL of the antibody dilutions was applied to each well. The plate was incubated at room temperature for 0.5-1 hour on a microplate shaker. The plate was washed 3 times with 1×PBS. 100 μL/well diluted HRP-conjugated goat anti-human Fc secondary antibody was applied to the wells. The plate was incubated for 1 hour on a microplate shaker. The plate was then washed 3 times with 1×PBS. 100 μL HRP substrate TMB was added to each well to develop the plate. After 3-5 minutes elapsed, the reaction was terminated by adding 100 μL of 1N HCl. A second direct binding ELISA was performed with only CML coating. The absorbance at OD450 was read using a microplate reader.

The OD450 absorbance raw data for the CML and CML-KLH ELISA is shown in the plate map below. 48 of the 96 wells in the well plate were used. Blank wells in the plate map indicate unused wells.

Plate Map of CML and CML-KLH ELISA:

| | Conc. (ug/mL) | | | | | | |
|---|---|---|---|---|---|---|---|
| | 1 | 2 | 3 | 4 | 5 | 6 | 7 |
| 50 | 0.462 | 0.092 | 0.42 | | 1.199 | 0.142 | 1.852 |
| 16.67 | 0.312 | 0.067 | 0.185 | | 0.31 | 0.13 | 0.383 |
| 5.56 | 0.165 | 0.063 | 0.123 | | 0.19 | 0.115 | 0.425 |
| 1.85 | 0.092 | 0.063 | 0.088 | | 0.146 | 0.099 | 0.414 |
| 0.62 | 0.083 | 0.072 | 0.066 | | 0.108 | 0.085 | 0.248 |
| 0.21 | 0.075 | 0.066 | 0.09 | | 0.096 | 0.096 | 0.12 |
| 0.07 | 0.086 | 0.086 | 0.082 | | 0.098 | 0.096 | 0.098 |
| 0 | 0.09 | 0.085 | 0.12 | | 0.111 | 0.083 | 0.582 |
| | R&D Positive Control | Parental Anti-AGE | Chimeric Anti-AGE | | R&D Positive Control | Parental Anti-AGE | Chimeric Anti-AGE |
| | CML-KLH Coat | | | | CML Coat | | |

The OD450 absorbance raw data for the CML-only ELISA is shown in the plate map below. 24 of the 96 wells in the well plate were used. Blank wells in the plate map indicate unused wells.

Plate Map of CML-Only ELISA:

| | Conc. (ug/mL) | | | | | |
|---|---|---|---|---|---|---|
| | 1 | 2 | 3 | 4 | 5 | 6 | 7 |
| 50 | 1.913 | 0.165 | 0.992 | | | | |
| 16.66667 | 1.113 | 0.226 | 0.541 | | | | |
| 5.555556 | 0.549 | 0.166 | 0.356 | | | | |
| 1.851852 | 0.199 | 0.078 | 0.248 | | | | |
| 0.617284 | 0.128 | 0.103 | 0.159 | | | | |
| 0.205761 | 0.116 | 0.056 | 0.097 | | | | |
| 0.068587 | 0.073 | 0.055 | 0.071 | | | | |
| 0 | 0.053 | 0.057 | 0.06 | | | | |
| | R&D Positive Control | Parental Anti-AGE | Chimeric Anti-AGE | | | | |

The control and chimeric anti-AGE antibodies showed binding to both CML and CML-KLH. The murine (parental) anti-AGE antibody showed very weak to no binding to either CML or CML-KLH. Data from repeated ELISA confirms binding of the control and chimeric anti-AGE to CML. All buffer control showed negative signal.

Example 5: Humanized Antibodies

Humanized antibodies were designed by creating multiple hybrid sequences that fuse select parts of the parental (mouse) antibody sequence with the human framework sequences. Acceptor frameworks were identified based on the overall sequence identity across the framework, matching interface position, similarly classed CDR canonical positions, and presence of N-glycosylation sites that would have to be removed. Three humanized light chains and three humanized heavy chains were designed based on two different heavy and light chain human acceptor frameworks. The amino acid sequences of the heavy chains are shown in SEQ ID NO: 29, 31 and 33, which are encoded by the DNA sequences shown in SEQ ID NO: 30, 32 and 34, respectively. The amino acid sequences of the light chains are shown in SEQ ID NO: 35, 37 and 39, which are encoded by the DNA sequences shown in SEQ ID NO: 36, 38 and 40, respectively. The humanized sequences were methodically analyzed by eye and computer modeling to isolate the sequences that would most likely retain antigen binding. The goal was to maximize the amount of human sequence in the final humanized antibodies while retaining the original antibody specificity. The light and heavy humanized chains could be combined to create nine variant fully humanized antibodies.

The three heavy chains and three light chains were analyzed to determine their humanness. Antibody humanness scores were calculated according to the method described in Gao, S. H., et al., "Monoclonal antibody humanness score and its applications", BMC Biotechnology, 13:55 (Jul. 5, 2013). The humanness score represents how human-like an antibody variable region sequence looks. For heavy chains a score of 79 or above is indicative of looking human-like; for light chains a score of 86 or above is indicative of looking human-like. The humanness of the three heavy chains, three light chains, a parental (mouse) heavy chain and a parental (mouse) light chain are shown below in Table 6:

TABLE 6

Antibody humanness

| Antibody | Humanness (Framework + CDR) |
|---|---|
| Parental (mouse) heavy chain | 63.60 |
| Heavy chain 1 (SEQ ID NO: 29) | 82.20 |
| Heavy chain 2 (SEQ ID NO: 31) | 80.76 |
| Heavy chain 3 (SEQ ID NO: 33) | 81.10 |
| Parental (mouse) light chain | 77.87 |
| Light chain 1 (SEQ ID NO: 35) | 86.74 |
| Light chain 2 (SEQ ID NO: 37) | 86.04 |
| Light chain 3 (SEQ IN NO: 39) | 83.57 |

Full-length antibody genes were constructed by first synthesizing the variable region sequences. The sequences were optimized for expression in mammalian cells. These variable region sequences were then cloned into expression vectors that already contain human Fc domains; for the heavy chain, the IgG1 was used.

Small scale production of humanized antibodies was carried out by transfecting plasmids for the heavy and light chains into suspension HEK293 cells using chemically defined media in the absence of serum. Whole antibodies in the conditioned media were purified using MabSelect SuRe Protein A medium (GE Healthcare).

Nine humanized antibodies were produced from each combination of the three heavy chains having the amino acid sequences shown in SEQ ID NO: 29, 31 and 33 and three light chains having the amino acid sequences shown in SEQ ID NO: 35, 37 and 39. A comparative chimeric parental antibody was also prepared. The antibodies and their respective titers are shown below in Table 7:

TABLE 7

Antibody titers

| Antibody | Titer (mg/L) |
|---|---|
| Chimeric parental | 23.00 |
| SEQ ID NO: 29 + SEQ ID NO: 35 | 24.67 |
| SEQ ID NO: 29 + SEQ ID NO: 37 | 41.67 |
| SEQ ID NO: 29 + SEQ ID NO: 39 | 29.67 |

TABLE 7-continued

Antibody titers

| Antibody | Titer (mg/L) |
|---|---|
| SEQ ID NO: 31 + SEQ ID NO: 35 | 26.00 |
| SEQ ID NO: 31 + SEQ ID NO: 37 | 27.33 |
| SEQ ID NO: 31 + SEQ ID NO: 39 | 35.33 |
| SEQ ID NO: 33 + SEQ ID NO: 35 | 44.00 |
| SEQ ID NO: 33 + SEQ ID NO: 37 | 30.33 |
| SEQ ID NO: 33 + SEQ ID NO: 39 | 37.33 |

The binding of the humanized antibodies may be evaluated, for example, by dose-dependent binding ELISA or cell-based binding assay.

REFERENCES

1. International Application Pub. No. WO 2009/143411 to Gruber (26 Nov. 2009).
2. U.S. Pat. No. 5,702,704 to Bucala (issued Dec. 30, 1997).
3. U.S. Pat. No. 6,380,165 to Al-Abed et al. (issued Apr. 30, 2002).
4. U.S. Pat. No. 6,387,373 to Wright et al. (issued May 14, 2002).
5. U.S. Pat. No. 4,217,344 to Vanlerberghe et al. (issued Aug. 12, 1980).
6. U.S. Pat. No. 4,917,951 to Wallach (issued Apr. 17, 1990).
7. U.S. Pat. No. 4,911,928 to Wallach (issued Mar. 27, 1990).
8. U.S. Patent Application Publication Pub. No. US 2010/226932 to Smith et al. (Sep. 9, 2010).
9. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999).
10. Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009).
11. Bierhaus A, "AGEs and their interaction with AGE-receptors in vascular disease and diabetes mellitus. I. The AGE concept," Cardiovasc Res, Vol. 37(3), 586-600 (1998).
12. Meuter A., et al. "Markers of cellular senescence are elevated in murine blastocysts cultured in vitro: molecular consequences of culture in atmospheric oxygen" J Assist Reprod Genet. 2014 Aug. 10. [Epub ahead of print].
13. Baker, D. J. et al., "Clearance of p16Ink4a-positive senescent cells delays ageing-associated disorders", Nature, vol. 479, pp. 232-236, (2011).
14. Jana Hadrabová, et al. "Chicken immunoglobulins for prophylaxis: Effect of inhaled antibodies on inflammatory parameters in rat airways" Journal of Applied Biomedicine (in press; Available online 5 May 2014).
15. Vlassara, H. et al., "High-affinity-receptor-mediated Uptake and Degradation of Glucose-modified Proteins: A Potential Mechanism for the Removal of Senescent Macromolecules", *Proc. Natl. Acad. Sci.* USA, Vol. 82, 5588, 5591 (1985).
16. Roll, P. et al., "Anti-CD20 Therapy in Patients with Rheumatoid Arthritis", *Arthritis & Rheumatism*, Vol. 58, No. 6, 1566-1575 (2008).
17. Kajstura, J. et al., "Myocite Turnover in the Aging Human Heart", *Circ. Res.*, Vol. 107(11), 1374-86, (2010).

18. de Groot, K. et al., "Vascular Endothelial Damage and Repair in Antineutrophil Cytoplasmic Antibody-Associated Vasculitis", *Arthritis and Rheumatism*, Vol. 56(11), 3847, 3847 (2007).
19. Manesso, E. et al., "Dynamics of β-Cell Turnover: Evidence for β-Cell Turnover and Regeneration from Sources of β-Cells other than β-cell Replication in the HIP Rat", *Am. J. Physiol. Endocrinol. Metab.*, Vol. 297, E323, E324 (2009).
20. Kirstein, M. et al., "Receptor-specific Induction of Insulin-like Growth Factor I in Human Monocytes by Advanced Glycosylation End Product-modified Proteins", *J. Clin. Invest.*, Vol. 90, 439, 439-440 (1992).
21. Murphy, J. F., "Trends in cancer immunotherapy", *Clinical Medical Insights: Oncology*, Vol. 14(4), 67-80 (2010).
22. Virella, G. et al., "Autoimmune Response to Advanced Glycosylation End-Products of Human LDL", *Journal of Lipid Research*, Vol. 44, 487-493 (2003).
23. Ameli, S. et al., "Effect of Immunization With Homologous LDL and Oxidized LDL on Early Atherosclerosis in Hypercholesterolemic Rabbits", *Arteriosclerosis, Thrombosis, and Vascular Biology*, Vol. 16, 1074 (1996).
24. "Sarcopenia", available online at en.wikipedia.org/wiki/Sarcopenia (Nov. 14, 2014).
25. "What is sarcopenia?", available online at www.iofbonehealth.org/what-sarcopenia (2014).
26. Bland, W., "Sarcopenia with aging", available online at www.webmd.com/healthy-aging/sarcopenia-with-aging (Aug. 3, 2014).
27. "Keyhole limpet hemocyanin", available online at en.wikipedia.org/wiki/Keyhole_limpet_hemocyanin (Apr. 18, 2014).
28. "CML-BSA Product Data Sheet", available online at www.cellbiolabs.com/sites/default/files/STA-314-cml-bsa.pdf (2010).
29. "CML (N-epsilon-(Carboxymethyl)Lysine) Assays and Reagents", available online at www.cellbiolabs.com/cml-assays (Accessed on Dec. 15, 2014).
30. Cruz-Jentoft, A. J. et al., "Sarcopenia: European consensus on definition and diagnosis", *Age and Ageing*, Vol. 39, pp. 412-423 (Apr. 13, 2010).
31. Rolland, Y. et al., "Sarcopenia: its assessment, etiology, pathogenesis, consequences and future perspectives", *J. Nutr. Health Aging*, Vol. 12(7), pp. 433-450 (2008).
32. Mera, K. et al., "An autoantibody against $N^\varepsilon$-(carboxyethyl)lysine (CEL): Possible involvement in the removal of CEL-modified proteins by macrophages", *Biochemical and Biophysical Research Communications*, Vol. 407, pp. 420-425 (Mar. 12, 2011).
33. Reddy, S. et al., "$N^\varepsilon$-(carboxymethyl)lysine is a dominant advanced glycation end product (AGE) antigen in tissue proteins", *Biochemistry*, Vol. 34, pp. 10872-10878 (Aug. 1, 1995).
34. Naylor, R. M. et al., "Senescent cells: a novel therapeutic target for aging and age-related diseases", *Clinical Pharmacology & Therapeutics*, Vol. 93(1), pp. 105-116 (Dec. 5, 2012).
35. Katcher, H. L., "Studies that shed new light on aging", *Biochemistry (Moscow)*, Vol. 78(9), pp. 1061-1070 (2013).
36. Ahmed, E. K. et al., "Protein Modification and Replicative Senescence of WI-38 Human Embryonic Fibroblasts", *Aging Cells*, Vol. 9, 252, 260 (2010).
37. Vlassara, H. et al., "Advanced Glycosylation Endproducts on Erythrocyte Cell Surface Induce Receptor-Mediated Phagocytosis by Macrophages", *J. Exp. Med.*, Vol. 166, 539, 545 (1987).
38. Fielding, R. A., et al., "Sarcopenia: an undiagnosed condition in older adults. Current consensus definition: prevalence, etiology, and consequences", *Journal of the American Medical Directors Association*, Vol. 12(4), pp. 249-256 (May 2011).
39. Maass, D. R. et al., "Alpaca (*Lama pacos*) as a convenient source of recombinant camelid heavy chain antibodies (VHHs)", Journal of Immunological Methods, Vol. 324, No. 1-2, pp. 13-25 (Jul. 31, 2007).
40. Strietzel, C. J. et al., "In vitro functional characterization of feline IgGs", Veterinary Immunology and Immunopathology, Vol. 158, pp. 214-223 (2014).
41. Patel, M. et al., "Sequence of the dog immunoglobulin alpha and epsilon constant region genes", Immunogenetics, Vol. 41, pp. 282-286 (1995).
42. Wagner, B. et al., "The complete map of the Ig heavy chain constant gene region reveals evidence for seven IgG isotypes and for IgD in the horse", The Journal of Immunology, Vol. 173, pp. 3230-3242 (2004).
43. Hamers-Casterman, C. et al., "Naturally occurring antibodies devoid of light chains", Nature, Vol. 363, pp. 446-448 (Jun. 3, 1993).
44. De Genst, E. et al., "Antibody repertoire development in camelids", Developmental & Comparative Immunology, Vol. 30, pp. 187-198 (available online Jul. 11, 2005).
45. Griffin, L. M. et al., "Analysis of heavy and light chain sequences of conventional camelid antibodies from *Camelus dromedarius* and *Camelus bactrianus* species", Journal of Immunological Methods, Vol. 405, pp. 35-46 (available online Jan. 18, 2014).
46. Nguyen, V. K. et al., "Camel heavy-chain antibodies: diverse germline $V_HH$ and specific mechanisms enlarge the antigen-binding repertoire", The European Molecular Biology Organization Journal, Vol. 19, No, 5, pp. 921-930 (2000).
47. Muyldermans, S. et al., "Sequence and structure of $V_H$ domain from naturally occurring camel heavy chain immunoglobulins lacking light chains", Protein Engineering, Vol. 7, No. 9, pp. 1129-1135 (1994).
48. Wesolowski, J. et al., "Single domain antibodies: promising experimental and therapeutic tools in infection and immunity", Medical Microbiology and Immunology, Vol. 198, pp. 157-174 (Jun. 16, 2009).
49. Yan, S. F. et al., "Soluble RAGE: therapy & biomarker in unraveling the RAGE axis in chronic disease and aging", Biochemical Pharmacology, Vol. 79, No. 10, pp. 1379-1386 (May 15, 2010).
50. Chen, K. S. et al., "Monoclonal antibody therapy for malignant glioma", Glioma: Immunotherapeutic Approaches, pp. 121-141 (2012).
51. Gao, S. H., et al., "Monoclonal antibody humanness score and its applications", BMC Biotechnology, 13:55 (Jul. 5, 2013).
52. Feige, M. J. et al., "The structural analysis of shark IgNAR antibodies reveals evolutionary principles of immunoglobulins", Proceedings of the National Academy of Sciences of the United States of America, Vol. 111, No. 22, pp. 8155-8160 (Jun. 3, 2014).

What is claimed is:

1. An anti-AGE antibody, comprising
   a heavy chain, and
   a light chain,
   wherein the heavy chain comprises an amino acid sequence having at least 90% sequence identity with an amino acid sequence selected from the group consisting of SEQ ID NO: 29, SEQ ID NO: 31, and SEQ ID NO: 33,
   the light chain comprises an amino acid sequence having at least 90% sequence identity with an amino acid sequence selected from the group consisting of SEQ ID NO: 35, SEQ ID NO: 37, and SEQ ID NO: 39, and
   the antibody binds to a protein or peptide that exhibits a carboxymethyllysine modification.

2. The anti-AGE antibody of claim 1, wherein the antibody is substantially non-immunogenic to a species selected from the group consisting of humans, goats, sheep, cows, horses, dogs and cats.

3. The anti-AGE antibody of claim 1, wherein the antibody is monoclonal.

4. The anti-AGE antibody of claim 1, wherein the antibody is substantially non-immunogenic to humans.

5. The anti-AGE antibody of claim 1, wherein the antibody has a rate of dissociation ($k_d$) of at most $9 \times 10^{-3}$ $sec^{-1}$.

6. The anti-AGE antibody of claim 1, wherein the antibody includes constant regions which permit destruction of targeted cells by a subject's immune system.

7. A pharmaceutical composition, comprising
   the anti-AGE antibody of claim 1, and
   a pharmaceutically acceptable carrier.

8. The pharmaceutical composition of claim 7, wherein the composition is sterile.

9. The pharmaceutical composition of claim 7, wherein the composition is in unit dosage form.

10. The pharmaceutical composition of claim 7, wherein the composition is injectable.

11. The anti-AGE antibody of claim 1, wherein the heavy chain comprises an amino acid sequence having at least 95% sequence identity with an amino acid sequence selected from the group consisting of SEQ ID NO: 29, SEQ ID NO: 31, and SEQ ID NO: 33, and
    the light chain comprises an amino acid sequence having at least 95% sequence identity with an amino acid sequence selected from the group consisting of SEQ ID NO: 35, SEQ ID NO: 37, and SEQ ID NO: 39.

12. The anti-AGE antibody of claim 1, wherein the heavy chain comprises an amino acid sequence having at least 98% sequence identity with an amino acid sequence selected from the group consisting of SEQ ID NO: 29, SEQ ID NO: 31, and SEQ ID NO: 33, and
    the light chain comprises an amino acid sequence having at least 98% sequence identity with an amino acid sequence selected from the group consisting of SEQ ID NO: 35, SEQ ID NO: 37, and SEQ ID NO: 39.

13. The anti-AGE antibody of claim 1, wherein the heavy chain comprises an amino acid sequence selected from the group consisting of SEQ ID NO: 29, SEQ ID NO: 31, and SEQ ID NO: 33, and
    the light chain comprises an amino acid sequence selected from the group consisting of SEQ ID NO: 35, SEQ ID NO: 37, and SEQ ID NO: 39.

14. An antibody conjugate, comprising
    an anti-AGE antibody, having
    a heavy chain, and
    a light chain, and
    an agent that causes the destruction of AGE-modified cells, conjugated to the anti-AGE antibody,
    wherein the heavy chain comprises an amino acid sequence having at least 90% sequence identity with an amino acid sequence selected from the group consisting of SEQ ID NO: 29, SEQ ID NO: 31, and SEQ ID NO: 33,
    the light chain comprises an amino acid sequence having at least 90% sequence identity with an amino acid sequence selected from the group consisting of SEQ ID NO: 35, SEQ ID NO: 37, and SEQ ID NO: 39, and
    the anti-AGE antibody binds to a protein or peptide that exhibits a carboxymethyllysine modification.

15. The antibody conjugate of claim 14, wherein the agent is selected from the group consisting of a toxin, a cytotoxic agent, magnetic nanoparticles, and magnetic spin-vortex discs.

16. The antibody conjugate of claim 14, wherein the antibody is substantially non-immunogenic to a species selected from the group consisting of humans, goats, sheep, cows, horses, dogs and cats.

17. The antibody conjugate of claim 14, wherein the antibody is monoclonal.

18. The antibody conjugate of claim 14, wherein the antibody is substantially non-immunogenic to humans.

19. The antibody conjugate of claim 14, wherein the antibody has a rate of dissociation (IQ of at most $9 \times 10^{-3}$ sec$^{-1}$.

20. A pharmaceutical composition, comprising
    the antibody conjugate of claim 14, and
    a pharmaceutically acceptable carrier.

21. The pharmaceutical composition of claim 20, wherein the composition is sterile.

22. The pharmaceutical composition of claim 20, wherein the composition is in unit dosage form.

23. The pharmaceutical composition of claim 20, wherein the composition is injectable.

24. The antibody conjugate of claim 14, wherein the heavy chain comprises an amino acid sequence having at least 95% sequence identity with an amino acid sequence selected from the group consisting of SEQ ID NO: 29, SEQ ID NO: 31, and SEQ ID NO: 33, and
    the light chain comprises an amino acid sequence having at least 95% sequence identity with an amino acid sequence selected from the group consisting of SEQ ID NO: 35, SEQ ID NO: 37, and SEQ ID NO: 39.

25. The antibody conjugate of claim 14, wherein the heavy chain comprises an amino acid sequence having at least 98% sequence identity with an amino acid sequence selected from the group consisting of SEQ ID NO: 29, SEQ ID NO: 31, and SEQ ID NO: 33, and
    the light chain comprises an amino acid sequence having at least 98% sequence identity with an amino acid sequence selected from the group consisting of SEQ ID NO: 35, SEQ ID NO: 37, and SEQ ID NO: 39.

26. The antibody conjugate of claim 14, wherein the heavy chain comprises an amino acid sequence selected from the group consisting of SEQ ID NO: 29, SEQ ID NO: 31, and SEQ ID NO: 33, and
    the light chain comprises an amino acid sequence selected from the group consisting of SEQ ID NO: 35, SEQ ID NO: 37, and SEQ ID NO: 39.

\* \* \* \* \*

UNITED STATES PATENT AND TRADEMARK OFFICE
CERTIFICATE OF CORRECTION

PATENT NO.         : 10,889,634 B2                              Page 1 of 46
APPLICATION NO.    : 15/768425
DATED              : January 12, 2021
INVENTOR(S)        : Lewis S. Gruber It is certified that error appears in the above-identified patent and that said Letters Patent is hereby corrected as shown below:

On the Title Page

Item (56) In the References Cited:

U.S. PATENT DOCUMENTS:
Column 1, please insert the following:

| | | |
|---|---|---|
| --4,217,344 | 8/1980 | Vanlerberghe et al. |
| 4,900,747 | 2/1990 | Vlassara et al. |
| 4,911,928 | 3/1990 | Wallach |
| 4,917,951 | 4/1990 | Wallach |
| 4,965,288 | 10/1990 | Palfreyman |
| 5,494,791 | 2/1996 | Cohen |
| 5,518,720 | 5/1996 | Cohen |
| 5,601,526 | 2/1997 | Chapelon et al. |
| 5,620,479 | 4/1997 | Diederich |
| 5,664,570 | 9/1997 | Bishop |
| 5,693,762 | 12/1997 | Queen et al. |
| 5,702,704 | 12/1997 | Bucala |
| 5,766,590 | 6/1998 | Founds et al. |
| 5,811,075 | 9/1998 | Vlassara et al. |
| 5,817,771 | 10/1998 | Bayley et al. |
| 5,984,882 | 11/1999 | Rosenschein et al. |
| 6,067,859 | 5/2000 | Kas et al. |
| 6,090,382 | 7/2000 | Salfeld et al. |
| 6,176,842 | 1/2001 | Tachibana et al. |
| 6,245,318 | 6/2001 | Klibanov et al. |
| 6,309,355 | 10/2001 | Cain et al. |
| 6,380,165 | 4/2002 | Al-Abed et al. |
| 6,387,373 | 5/2002 | Wright et al. |
| 6,410,598 | 6/2002 | Vitek |

Signed and Sealed this
Fifth Day of October, 2021

Drew Hirshfeld
*Performing the Functions and Duties of the
Under Secretary of Commerce for Intellectual Property
and
Director of the United States Patent and Trademark
Office*

CERTIFICATE OF CORRECTION (continued)
U.S. Pat. No. 10,889,634 B2

| | | |
|---|---|---|
| 6,670,136 | 12/2003 | Schmidt et al. |
| 6,676,963 | 1/2004 | Lanza et al. |
| 6,818,215 | 11/2004 | Smith et al. |
| 6,821,274 | 11/2004 | McHale et al. |
| 7,033,574 | 4/2006 | Schneider et al. |
| 7,101,838 | 9/2006 | Stern et al. |
| 7,256,273 | 8/2007 | Basi et al. |
| 7,347,855 | 3/2008 | Eshel et al. |
| 7,358,226 | 4/2008 | Dayton et al. |
| 7,367,988 | 5/2008 | Litovitz |
| 7,751,057 | 7/2010 | Oldenburg et al. |
| 7,815,570 | 10/2010 | Eshel et al. |
| 8,318,164 | 11/2012 | Warne |
| 8,323,651 | 12/2012 | Gu et al. |
| 8,343,420 | 1/2013 | Cioanta et al. |
| 8,398,977 | 3/2013 | Bleck et al. |
| 8,721,571 | 5/2014 | Gruber |
| 9,161,810 | 10/2015 | Gruber |
| 9,320,919 | 4/2016 | Gruber |
| 9,649,376 | 5/2017 | Gruber |
| 9,993,535 | 6/2018 | Gruber |
| 10,226,531 | 3/2019 | Gruber |
| 10,584,180 | 3/2020 | Gruber |
| 10/358,502 | 7/2019 | Gruber |
| 2002/0193784 | 12/2002 | McHale et al. |
| 2003/0073138 | 4/2003 | Kientsch-Engel et al. |
| 2003/0170173 | 9/2003 | Klaveness et al. |
| 2003/0229283 | 12/2003 | Craig et al. |
| 2004/0039416 | 2/2004 | Myhr |
| 2004/0141922 | 7/2004 | Klaveness et al. |
| 2004/0208826 | 10/2004 | Schneider et al. |
| 2004/0229830 | 11/2004 | Tachibana et al. |
| 2005/0084538 | 4/2005 | Dayton et al. |
| 2005/0283098 | 12/2005 | Conston et al. |
| 2006/0078501 | 4/2006 | Goertz et al. |
| 2006/0122543 | 6/2006 | Mayer et al. |
| 2006/0188883 | 8/2006 | Murray et al. |
| 2007/0059247 | 3/2007 | Lindner et al. |
| 2007/0065415 | 3/2007 | Kleinsek et al. |
| 2007/0065443 | 3/2007 | Tobia |
| 2007/0078290 | 4/2007 | Esenaliev |
| 2007/0083120 | 4/2007 | Cain et al. |
| 2007/0128117 | 6/2007 | Bettinger et al. |
| 2007/0129633 | 6/2007 | Lee et al. |
| 2007/0225242 | 9/2007 | Erler |
| 2008/0019986 | 1/2008 | Stern et al. |

| | | |
|---|---|---|
| 2008/0051680 | 2/2008 | Luebcke |
| 2008/0063603 | 3/2008 | Schneider et al. |
| 2008/0139942 | 6/2008 | Gaud et al. |
| 2008/0160506 | 7/2008 | Liu et al. |
| 2009/0022659 | 1/2009 | Olson et al. |
| 2009/0076390 | 3/2009 | Lee et al. |
| 2009/0306552 | 12/2009 | Furuzono et al. |
| 2010/0028359 | 2/2010 | Gu et al. |
| 2010/0226932 | 9/2010 | Smith et al. |
| 2011/0105961 | 5/2011 | Gruber |
| 2011/0319499 | 12/2011 | Semba et al. |
| 2012/0130287 | 5/2012 | Gruber |
| 2012/0156134 | 6/2012 | Squires |
| 2012/0183534 | 7/2012 | Gruber |
| 2013/0058921 | 3/2013 | Van Rhee |
| 2013/0243785 | 9/2013 | Gruber |
| 2013/0288980 | 10/2013 | De Keizer et al. |
| 2013/131006 | 5/2013 | Lee et al. |
| 2014/0234339 | 8/2014 | Ohlsen |
| 2014/0303526 | 10/2014 | Gruber |
| 2014/234343 | 8/2014 | Lee et al. |
| 2015/0376279 | 12/2015 | Hansen |
| 2016/0101299 | 4/2016 | Gruber |
| 2016/0152697 | 11/2015 | Gruber |
| 2016/0175413 | 6/2016 | Gruber |
| 2016/0193358 | 7/2016 | Algate |
| 2016/0215043 | 7/2016 | Gruber |
| 2016/0339019 | 11/2016 | Laberge et al. |
| 2016/0340418 | 11/2016 | Baron |
| 2017/0216435 | 8/2017 | Gruber |
| 2017/0247472 | 8/2017 | Gruber |
| 2018/0044411 | 2/2018 | Gruber |
| 2018/0111982 | 4/2018 | Gruber |
| 2018/0298087 | 10/2018 | Gruber |
| 2018/0312577 | 11/2018 | Gruber |
| 2018/0326026 | 11/2018 | Gruber |
| 2019/0031781 | 1/2019 | Gruber |
| 2019/0119371 | 4/2019 | Gruber |
| 2019/0328873 | 10/2019 | Gruber |
| 2019/0328876 | 10/2019 | Gruber |
| 2020/0055957 | 2/2020 | Gruber-- |

FOREIGN PATENT DOCUMENTS:
Page 2, Column 2, please insert the following:
--AU    2009248945           11/2012
AU    2009248945           4/2013

CERTIFICATE OF CORRECTION (continued)
U.S. Pat. No. 10,889,634 B2

| | | |
|---|---|---|
| AU | 2009248945 | 2/2014 |
| AU | 2011332143 | 6/2015 |
| AU | 2014202548 | 6/2015 |
| AU | 2014202548 | 1/2016 |
| AU | 2011332143 | 1/2016 |
| AU | 2011332143 | 1/2016 |
| AU | 2014202548 | 4/2016 |
| AU | 2014202548 | 6/2016 |
| AU | 2016204196 | 8/2016 |
| AU | 2009/248945 | 5/2014 |
| CA | 2,724,886 | 6/2014 |
| CA | 2,724,886 | 2/2015 |
| CA | 2,724,886 | 9/2015 |
| CA | 2,724,886 | 4/2016 |
| CA | 2,818,647 | 10/2016 |
| CA | 2,724,886 | 2/2017 |
| CA | 2,724,886 | 5/2017 |
| CA | 2,818,647 | 4/2017 |
| CA | 2,818,647 | 10/2017 |
| CA | 2,818,647 | 11/2017 |
| CA | 2,818,647 | 6/2018 |
| CA | 2,818,647 | 7/2018 |
| CN | 200980118817.6 | 5/2012 |
| CN | 200980118817.6 | 2/2013 |
| CN | 200980118817.6 | 10/2013 |
| CN | 200980118817.6 | 5/2014 |
| CN | 200980118817.6 | 10/2014 |
| CN | 200980118817.6 | 3/2015 |
| CN | 201510303227.8 | 6/2016 |
| CN | 201510303227.8 | 12/2016 |
| CN | 201510303227.8 | 5/2017 |
| CN | 201580056616.3 | 4/2020 |
| DE | 102008009461 | 8/2009 |
| EP | 9751639.7 | 11/2011 |
| EP | 9751639.7 | 6/2012 |
| EP | 9751639.7 | 1/2013 |
| EP | 9751639.7 | 7/2013 |
| EP | 9751639.7 | 1/2014 |
| EP | 14170802.4 | 9/2014 |
| EP | 14170802.4 | 7/2015 |
| EP | 14170802.4 | 12/2015 |
| EP | 16198527 | 2/2017 |
| EP | 11776932.3 | 3/2017 |
| EP | 14170802.4 | 11/2016 |
| EP | 11776932.3 | 8/2017 |
| EP | 11776932.3 | 3/2018 |

| | | |
|---|---|---|
| EP | 15772116.8 | 9/2018 |
| EP | 17708098.3 | 1/2019 |
| EP | 17708098.3 | 2/2019 |
| EP | 18184822.7 | 6/2019 |
| EP | 17708098.3 | 7/2019 |
| EP | 14170802.4 | 4/2016 |
| EP | 11776932.3 | 9/2017 |
| EP | 11776932.3 | 1/2018 |
| EP | 11776932.3 | 2/2018 |
| EP | 11776932.3 | 3/2018 |
| EP | 15772116.8 | 1/2019 |
| EP | 17737078 | 8/2019 |
| EP | 18184822.7 | 1/2019 |
| EP | 15772116.8 | 2/2019 |
| EP | 11776932.3 | 2/2019 |
| EP | 18726656.4 | 12/2019 |
| EP | 15772116.8 | 3/2020 |
| EP | 259893 | 3/1988 |
| EP | 1219639 | 7/2002 |
| EP | 1415997 | 5/2004 |
| EP | 1867659 | 12/2007 |
| EP | 2294178 | 7/2014 |
| IL | 209513 | 8/2012 |
| IL | 209513 | 5/2013 |
| IL | 209513 | 5/2014 |
| IL | 209513 | 12/2014 |
| IL | 240242 | 4/2016 |
| IL | 240242 | 1/2017 |
| IL | 248652 | 5/2017 |
| IN | 4875/KOLNP/2010 | 12/2016 |
| JP | 2011-511734 | 11/2013 |
| JP | 2011-511734 | 12/2014 |
| JP | 2015-076575 | 6/2015 |
| JP | 2015-076575 | 1/2016 |
| JP | 2016-098558 | 7/2016 |
| JP | 2016-098558 | 12/2016 |
| JP | 2017-086871 | 4/2018 |
| JP | 2017086871 | 3/2019 |
| JP | 2017-515740 | 7/2019 |
| JP | 2017-515740 | 1/2020 |
| JP | 2018-543120 | 3/2020 |
| JP | 9178740 | 7/1997 |
| JP | 11246599 | 9/1999 |
| JP | 2003/160599 | 6/2003 |
| JP | 2006-249015 | 9/2006 |
| KR | 10-2012-7026063 | 7/2012 |

| | | |
|---|---|---|
| KR | 10-2010-7026063 | 2/2013 |
| KR | 10-2010-7026063 | 9/2013 |
| KR | 10-2010-7026063 | 12/2013 |
| KR | 10-2013-7028228 | 6/2014 |
| KR | 10-2010-7026063 | 7/2014 |
| KR | 10-2012-7026483 | 7/2014 |
| KR | 10-2012-7026483 | 2/2015 |
| KR | 10-2013-7028228 | 4/2015 |
| KR | 10-2015-7007520 | 4/2015 |
| KR | 10-2015-7007520 | 11/2015 |
| MX | 2010/012473 | 7/2013 |
| MX | 2010/012473 | 3/2014 |
| MX | 2010/012473 | 6/2014 |
| MX | MX/a/2013/013310 | 7/2015 |
| MX | MX/a/2013/013310 | 4/2016 |
| MX | MX/a/2013/013310 | 2/2017 |
| RU | 2010152693 | 12/2012 |
| RU | 2010152693 | 4/2013 |
| RU | 2010152693 | 5/2014 |
| RU | 2010152693 | 12/2014 |
| RU | 2015114990 | 7/2016 |
| RU | 2015114990 | 1/2017 |
| RU | 2017113349 | 5/2017 |
| RU | 2015114990 | 8/2017 |
| RU | 2015114990 | 10/2017 |
| RU | 2017113349 | 12/2018 |
| RU | 2017113349 | 4/2019 |
| RU | 2018110885 | 1/2020 |
| RU | 2018110885 | 1/2020 |
| RU | 2017113349 | 3/2020 |
| RU | 2270029 | 1/2006 |
| WO | PCT/US2009/44951 | 7/2009 |
| WO | PCT/US2009/44951 | 12/2010 |
| WO | PCT/US2011/053399 | 4/2012 |
| WO | PCT/US2011/061387 | 6/2012 |
| WO | PCT/US12/31446 | 6/2012 |
| WO | PCT/US2011/061387 | 5/2013 |
| WO | 11776932.3 | 4/2013 |
| WO | PCT/US2012/031446 | 10/2013 |
| WO | PCT/US2015/050154 | 3/2016 |
| WO | PCT/US2016/039076 | 12/2016 |
| WO | PCT/US2016/034880 | 8/2016 |
| WO | PCT/US2017/018185 | 5/2017 |
| WO | PCT/US2016/034880 | 8/2016 |
| WO | PCT/US2015/050154 | 3/2017 |
| WO | PCT/US2017/027773 | 9/2017 |

CERTIFICATE OF CORRECTION (continued)
U.S. Pat. No. 10,889,634 B2

| | | |
|---|---|---|
| WO | PCT/US2017/018185 | 8/2018 |
| WO | PCT/US2017/027773 | 10/2018 |
| WO | PCT/US2016/039076 | 12/2018 |
| WO | PCT/US2018/030931 | 11/2019 |
| WO | 1995/20979 | 8/1995 |
| WO | 1996/20958 | 7/1996 |
| WO | 1997/49429 | 12/1997 |
| WO | 1999/07893 | 2/1999 |
| WO | 1999/14587 | 3/1999 |
| WO | 1999/64463 | 12/1999 |
| WO | 2000/20458 | 4/2000 |
| WO | 2001/00245 | 1/2001 |
| WO | 2004/011460 | 2/2004 |
| WO | 2004/016229 | 2/2004 |
| WO | 2004/076677 | 9/2004 |
| WO | 2006/012415 | 2/2006 |
| WO | 2006/017647 | 2/2006 |
| WO | 2006/040597 | 4/2006 |
| WO | 2009/136382 | 11/2009 |
| WO | 2009/143411 | 11/2009 |
| WO | 2010/005531 | 1/2010 |
| WO | 2012/047629 | 4/2012 |
| WO | 2012/071269 | 5/2012 |
| WO | 2012/135616 | 10/2012 |
| WO | 2013/009785 | 1/2013 |
| WO | 2013/043161 | 3/2013 |
| WO | 2013/070468 | 5/2013 |
| WO | 2014/136114 | 9/2014 |
| WO | 2015/112835 | 7/2015 |
| WO | 2015/116740 | 8/2015 |
| WO | 2016/044252 | 3/2016 |
| WO | 2017/065837 | 4/2017 |
| WO | 2017/143073 | 8/2017 |
| WO | 2017/181116 | 10/2017 |
| WO | 2017/222535 | 12/2017 |
| WO | 2018/191718 | 10/2018 |
| WO | 2018/204679 | 11/2018 |
| WO | 2020/023532 | 1/2020 |
| WO | 2020/041625 | 2/2020-- |

OTHER PUBLICATIONS:
Page 3, Column 2, please insert the following:
--Jun. 14, 2012, U.S. Appl. No. 12/994,421.
Jul. 2, 2012, U.S. Appl. No. 12/951,768.
Mar. 30, 2012, U.S. Appl. No. 12/951,768.
Jul.20, 2012, U.S. Appl. No. 12/994,421.

Sept. 10, 2012, U.S. Appl. No. 12/994,421.
Nov. 5, 2012, U.S. Appl. No. 12/951,768.
Feb. 26, 2013, U.S. Appl. No. 12/994,421.
Mar. 21, 2013, U.S. Appl. No. 12/951,768.
Mar. 27, 2013, U.S. Appl. No. 12/951,768.
May 21, 2013, U.S. Appl. No. 12/994,421.
Jul. 18, 2013, U.S. Appl. No. 12/994,421.
Jul. 29, 2013, U.S. Appl. No. 12/951,768.
Nov. 15, 2013, U.S. Appl. No. 12/951,768.
Dec. 20, 2013, U.S. Appl. No. 12/951,768.
Sept. 3, 2014, U.S. Appl. No. 13/332,976.
Sept. 9, 2014, U.S. Appl. No. 14/247,081.
Nov. 18, 2014, U.S. Appl. No. 13/332,976.
Nov. 18, 2014, U.S. Appl. No. 12/994,421.
Jan. 13, 2015, U.S. Appl. No. 14/247,081.
Feb. 2, 2015, U.S. Appl. No. 14/247,081.
Mar. 13, 2015, U.S. Appl. No. 12/994,421.
Mar. 13, 2015, U.S. Appl. No. 13/332,976.
Mar. 27, 2015, U.S. Appl. No. 12/994,421.
Apr. 1, 2015, U.S. Appl. No. 13/332,976.
Apr. 23, 2015, U.S. Appl. No. 13/332,976.
May 1, 2015, U.S. Appl. No. 13/332,976.
May 6, 2015, U.S. Appl. No. 14/247,081.
Jun. 11, 2015, U.S. Appl. No. 13/332,976.
Jul. 10, 2015, U.S. Appl. No. 14/247,081.
Jul. 21, 2015, U.S. Appl. No. 14/278,081.
Sept. 10, 2015, U.S. Appl. No. 13/876,157.
Sept. 2, 2015, U.S. Appl. No. 12/994,421.
Jan. 19, 2016, U.S. Appl. No. 12/994,421.
Mar. 30, 2016, U.S. Appl. No. 13/876,157.
Oct. 17, 2016, U.S. Appl. No. 13/876,157.
Sept. 22, 2016, U.S. Appl. No. 14/974,095.
Jan. 5, 2017, U.S. Appl. No. 13/876,157.
Feb. 13, 2017, U.S. Appl. No. 14/974,095.
Jun. 13, 2017, U.S. Appl. No. 14/974,561.
Jun. 27, 2017, U.S. Appl. No. 14/974,095.
Sept. 22, 2017, U.S. Appl. No. 14/974,095.
Nov. 15, 2017, U.S. Appl. No. 14/974,561.
Nov. 30, 2017, U.S. Appl. No. 14/932,200.
Jan. 11, 2018, U.S. Appl. No. 14/974,095.
Jan. 30, 2018, U.S. Appl. No. 14/974,095.
Feb. 8, 2018, U.S. Appl. No. 14/974,561.
Feb. 21, 2018, U.S. Appl. No. 14/932,200.
May 11, 2018, U.S. Appl. No. 14/974,095.
May 14, 2018, U.S. Appl. No. 14/920,737.
May 21, 2018, U.S. Appl. No. 15/511,731.

May 21, 2018, U.S. Appl. No. 15/489,624.
May 29, 2018, U.S. Appl. No. 14/974,561.
Sept. 5, 2018, U.S. Appl. No. 14/932,200.
Sept. 12, 2018, U.S. Appl. No. 14/920,737.
Sept. 25, 2018, U.S. Appl. No. 14/974,561.
Oct. 23, 2018, U.S. Appl. No. 15/489,624.
Nov. 15, 2018, U.S. Appl. No. 15/511,731.
Nov. 28, 2018, U.S. Appl. No. 15/720,912.
Dec. 13, 2018, U.S. Appl. No. 14/932,200.
Jan. 23, 2019, U.S. Appl. No. 15/489,624.
Feb. 4, 2019, U.S. Appl. No. 15/863,811.
Feb. 6, 2019, U.S. Appl. No. 14/974,561.
Feb. 11, 2019, U.S. Appl. No. 15/863,784.
Feb. 14, 2019, U.S. Appl. No. 15/511,731.
Mar. 4, 2019, U.S. Appl. No. 14/920,737.
Mar. 12, 2019, U.S. Appl. No. 14/974,561.
Mar. 26, 2019, U.S. Appl. No. 15/720,912.
Apr. 10, 2019, U.S. Appl. No. 15/863,741.
Mar. 20, 2019, U.S. Appl. No. 15/863,828.
Jun. 7, 2019, U.S. Appl. No. 14/932,200.
Aug. 15, 2019, U.S. Appl. No. 14/920,737.
Jun. 27, 2019, U.S. Appl. No. 15/511,731.
Sept. 25, 2019, U.S. Appl. No. 15/863,811.
Sept. 30, 2019, U.S. Appl. No. 15/863,784.
Oct. 7, 2019, U.S. Appl. No. 15/863,828.
Oct. 11, 2019, U.S. Appl. No. 15/953,244.
Oct. 15, 2019, U.S. Appl. No. 16/092,743.
Oct. 21, 2019, U.S. Appl. No. 15/511,731.
Oct. 30, 2019, U.S. Appl. No. 15/720,912.
Nov. 1, 2019, U.S. Appl. No. 15/863,811.
Nov. 20, 2019, U.S. Appl. No. 14/932,200.
Nov. 21, 2019, U.S. Appl. No. 15/863,784.
Dec. 5, 2019, U.S. Appl. No. 15/863,741.
Dec. 11, 2019, U.S. Appl. No. 15/977,587.
Dec. 20, 2019, U.S. Appl. No. 15/863,828.
Jan. 13, 2020, U.S. Appl. No. 14/920,737.
Jan. 27, 2020, U.S. Appl. No. 15/511,731.
Feb. 13, 2020, U.S. Appl. No. 15/863,741.
Feb. 7, 2020, U.S. Appl. No. 15/863,784.
Feb. 11, 2020, U.S. Appl. No. 15/863,811.
Mar. 20, 2020, U.S. Appl. No. 15/953,244.
Mar. 31, 2020, U.S. Appl. No. 14/920,737.
Mar. 18, 2020, U.S. Appl. No. 16/092,743.
Apr. 16, 2020, U.S. Appl. No. 15/863,828.
Apr. 20, 2020, U.S. Appl. No. 15/863,741.
International Search Report dated July 21, 2009 for PCT application number PCT/US2009/44951.

Lindsey, J.B. et al., "Receptor for advanced glycation end-products (RAGE) and soluble RAGE (sRAGE): Cardiovascular implications", Diabetes Vascular Disease Research, vol. 6, no. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, no. 2, pp. 101-105, (2000).
Horiuchi, S. et al., "Immunochemical approach to characterize advanced glycation end products of the maillard reaction", The Journal of Biological Chemistry, vol. 266, no. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, no. 5B, pp. 3070-3073, (1998).
Harja, E. et al., "Vascular and inflammatory stresses mediate atherosclerosis via RAGE and its ligands in apoE-/- mice", The Journal of Clinical Investigation, vol. 118, no. 1, pp. 183-194, (2008).
Carstensen, E.L. et al., "Lysis of erythrocytes by exposure to cw ultrasound", Ultrasound in Medicine and Biology, vol. 19, no. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, no. 4, pp. 635-638, (1997).
Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-γ activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, no. 29, pp 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).

Christian, S. et al., "Nucleolin expressed at the cell surface is a marker of endothelial cells in angiogenic blood vessels", Journal of Cell Biology, vol. 163, no. 4, pp. 871-878, (2003).

Loo, T.W. et al., "Identification of residues in the drug translocation pathway of the human multidrug resistance P-glycoprotein by arginine mutagenesis", Journal of Biological Chemistry, vol. 284, no. 36, pp. 24074-24087, (2009).

Brundin, P. et al., "Prion-like transmission of protein aggregates in neurodegenerative diseases", Nature Reviews Molecular Cell Biology, vol. 11, no. 4, pp. 301-307, (2010).

Perez, C. et al., Translational control of the abundance of cytoplasmic poly(A) binding protein in human cytomegalovirus-infected cells", Journal of Virology, vol. 85, no. 1, pp. 156-164, (2011).

Persson, J. et al., "Interleukin-Ibeta and tumour necrosis factor-alpha impede neutral lipid turnover in macrophage-derived foam cells", BMC Immunology, vol. 9, no. 70, pp. 1-11, (2008).

Vergne, I. et al., "Cell biology of mycobacterium tuberculosis phagosome", Annu. Rev. Cell Dev. Biology, vol. 20, pp. 367-394, (2004).

Moskowitz, S.M. et al., "The role of pseudomonas lipopolysaccharide in cystic fibrosis airway Infection", Subcell Biochemistry, vol. 53, pp. 241-253, (2010).

Hall-Stoodley, L. et al., "Direct detection of bacterial biofilms on the middle-ear mucosa of children with chronic otitis media", JAMA, vol. 296, no. 2, pp. 202-211, (2006).

Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).

Zhang, S. et al., "Delineation of diverse macrophage activation programs in response to intracellular parasites and cytokines", PLoS Neglected Tropical Diseases, vol. 4, no. 3, e648 (2010).

Ma, Y. et al., "NS3 helicase domains involved in infectious intracellular hepatitis C virus particle assembly", Journal of Virology, vol. 82, no. 15, pp. 7624-7639, (2008).

Korant, B.D. et al., "Inhibition by zinc of rhinovirus protein cleavage: interaction of zinc with capsid polypeptides", Journal of Virology, vol. 18, no. 1, pp. 298-306, (1976).

Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).

Nilsson, J. et al., "Inflammation and immunity in diabetic vascular complications", Current Opinion in Lipidology, vol. 19, issue 5, pp. 519-524, (2008)

Schiopu, A. et al., "Recombinant antibodies to an oxidized low-density lipoprotein epitope induce rapid regression of atherosclerosis in apobec-1-/-/low-density lipoprotein receptor-/-mice", Journal of the American College of Cardiology, vol. 50, no. 24, pp. 2313-2318, (2007).

Schiopu, A. et al., "Recombinant human antibodies against aldehyde-modified apolipoprotein B-100 peptide sequences inhibit atherosclerosis", Circulation, vol. 110, pp. 2047-2052, (2004).

Bassirat, M. et al., "Short- and long-term modulation of microvascular responses in streptozotocin-induced diabetic rats by glycosylated products", Journal of Diabetes and its Complications, vol. 24, pp. 64-72, (2010).

Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).

Gugliucci, A. et al., "Circulating advanced glycation peptides in streptozotocin-induced diabetic rats: evidence for preferential modification of IgG light chains", Life Sciences, vol. 62, no. 23, pp. 2141-2150, (1998).

Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, no. 4, pp. 665-673, (2010).
Kyte, J.A. et al., "Third international conference on cancer vaccines/adjuvants/delivery for the next decade (CVADD 2009)", Expert Reviews Vaccines, vol. 9, no. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, no. 10, pp. 1753-1760, (2008).
Li, Y.M. et al., "Glycation products in aged thioglycollate medium enhance the elicitation of peritoneal macrophages", Journal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, no. 2, pp. 83-97, (2001).
Jiang, Z-H. et al., "Synthetic vaccines: the role of adjuvants in immune targeting", Current Medicinal Chemistry, vol. 10, no. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, no. 9, pp. 751-762, (2010).
Shcheglova, T. et al., "Reactive immunization suppresses advanced glycation and mitigates diabetic nephropathy", Journal of the American Society of Nephrology, vol. 20, no. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in Escherichia coli", Microbial Cell Factories, vol. 9, no. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in Escherichia coli", The Journal of Biological Chemistry, vol. 278, no. 51, pp. 51068-51074, (2003).

Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated November 8, 2011 for PCT application number PCT/US2009/044951.
Bierhaus, A. et al., "AGEs and their interaction with AGE-receptors in vascular disease and diabetes mellitus. I. the AGE concept", Cardiovascular Research, vol. 37, no. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, no. 6, pp. 277-285, (2009).
Coler, R.N. et al., "Development and characterization of synthetic glucopyranosyl lipid adjuvant system as a vaccine adjuvant", PLoS One, vol. 6, no. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11th Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11th Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/ 18410.aspx, 1 page, published October 8, 2009.
Ellis, G., "The myth of the glycemic index and its child: good carbs-bad carbs", Targeted Body Systems, www.targetedbodysystems.com/tag/low-carb-diet-plans/, pp. 1-5, published February 16, 2009.
"Diabetic glycation and inflammation – what diabetes does to your coronary arteries", www.rebelheartsurgeon-antioxidants.net/diabetic-glycation.html, pp. 1-9, downloaded August 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, no. 32, pp. 20431-20436, (1994).
Peters Jr. T.,"5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).

Roll, P. et al., "Anti-CD20 therapy in patients with rheumatoid arthritis", Arthritis & Rheumatism, vol. 58, no. 6, pp. 1566-1575, (2008).

Kajstura J. et al., "Myocyte turnover in the aging human heart", Circulation Research, vol. 107, pp. 1374-1386, (2010).

Baker, D.J. et al., "Clearance of p16Ink4a-positive senescent cells delays ageing-associated disorders", Nature, vol. 479, pp. 232-236, (2011).

Breyer, V. et al., "Intracellular glycation of nuclear DNA, mitochondrial DNA, and cytosolic proteins during senescence-like growth arrest", DNA Cell Biology, vol. 30, no. 9, pp. 681-689, (2011).

Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).

International Search Report dated April 26, 2012 for PCT application number PCT/US2011/053399.

International Search Report dated June 13, 2012 for PCT application number PCT/US2011/061387.

Wautier, J. -L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, no. 16, pp. 7742-7746, (1994).

Siegel, R. J. et al., "Ultrasonic plaque ablation: A new method for recanalization of partially or totally occluded arteries", Circulation, vol. 78, no. 6, pp. 1443-1448, (1988).

International Search Report dated June 27, 2012 for PCT application number PCT/US2012/031446.

Immuno, Catalog Number: 637061, 637062, "Mouse, anti-age (advanced glycation end products), monoclonal antibody", http://www.mpbio.com/detailed_info.php?family_key=0863706, 2 pages, accessed July 26, 2012.

Ahmed, E. K. et al., "Protein modification and replicative senescence of WI-38 human embryonic fibroblasts", Aging Cell, vol. 9, pp. 252-272, (2010).

Vlassara, H. et al, "Advanced glycosylation endproducts on erythrocyte cell surface induce receptor-mediated phagocytosis by macrophages", J. Exp. Med., The Rockefeller University Press, volume 166, pp. 539-549, (1987).

Yang, Z. et al., "Two novel rat liver membrane proteins that bind advanced glycosylation endproducts: Relationship to macrophage receptor for glucose-modified proteins", J. Exp. Med., The Rockefeller University Press, volume 174, pp. 515-524, (1991).

Vlassara, H. et al, "Advanced glycation endproducts promote adhesion molecule (VCAM-1, ICAM-1) expression and atheroma formation in normal rabbits", Molecular Medicine, volume 1, number 4, pp. 447-456, (1995).

Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).

Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).

Manesso, E. et al., "Dynamics of β-cell turnover: evidence for β-cell turnover and regeneration from sources of β-cells other than β-cell replication in the HIP rat", American Journal of Physiology – Endocrinology and Metabolism, vol. 297, pp. E323-E330, (2009).

Stepanov, A.V. et al., "Design of targeted B cell killing agents", PLoS ONE, vol. 6, issue 6, e20991, pp. 1-10, (2011).

Fact Sheet, "Targeted Cancer Therapies", www.cancer.gov/cancertopics/factsheet/Therapy/Fs7_49.pdf, pp. 1-8, (2012).

Kay, M.M. "Generation of senescent cell antigen on old cells initiates IgG binding to a neoantigen", Cellular and Molecular Biology (Noisy-le-Grand, France), vol. 39, no2, pp. 131-153, (1993), Abstract Only.

Cirocchi, R. et al., "Meta-analysis of thyroidectomy with ultrasonic dissector versus conventional clamp and tie", World Journal of Surgical Oncology, vol. 8, no. 112, pp. 1-7, (2010).

Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).

de Groot, K. et al., "Vascular endothelial damage and repair in antineutrophil cytoplasmic antibody - associated vasculitis", Arthritis & Rheumatism, vol. 56, no. 11, pp. 3847-3853, (2007).

Imani, F. et al., "Advanced glycosylation endproduct-specific receptors on human and rat t-lymphocytes mediate synthesis of interferon $\gamma$: role in tissue remodeling", J. Exp. Med., vol. 178, pp. 2165-2172, (1993).

Kirstein, M. et al., "Receptor-specific induction of insulin-like growth factor I in human monocytes by advanced glycosylation end product-modified proteins", J. Clin. Invest., vol. 90, pp. 439-446, (1992).

Le Grand, F. et al., "Skeletal muscle satellite cells and adult myogenesis", Curr. Opin. Cell Biology, vol. 19, no. 6, pp. 628-633, (2007).

Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).

Misur, I. et al., "Advanced glycation endproducts in peripheral nerve in type 2 diabetes with neuropathy", Acta Diabetol, vol. 41, pp. 158-166, (2004).

Saltykov, B.B., "Mechanisms of development of diabetic macroangiopathy", Arkh Patol., vol. 63, no. 2, pp. 21-26, (2001), Abstract Only.

Grossin, N. et al., "Red blood cell adhesion in diabetes mellitus is mediated by advanced glycation end product receptor and is modulated by nitric oxide", Biorheology, vol. 46, no. 1, pp. 63-72, (2009).

Liang, Y. et al., "Rituximab for children with immune thrombocytopenia: A systematic review", PLoS ONE, vol. 7, issue 1, pp. 1-11, (2012).

Fehrenbach, H. et al., "Up-regulated expression of the receptor for advanced glycation end products in cultured rat hepatic stellate cells during transdifferentiation to myofibroblasts", Hepatology, vol. 34, no. 5, pp. 943-952, (2001).

Agostini, A. et al., "Targeted cargo delivery in senescent cells using capped mesoporous silica nanoparticles", Angewandte Chemie International Edition, vol. 51, pp. 10556-10560, (2012).

Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on June 11, 2013.

Hansel, T.T. et al., "The safety and side effects of monoclonal antibodies", Nature Reviews, vol. 9, pp. 325-337, (2010).

Nass, N. et al., "Advanced glycation end products, diabetes and ageing", Zeitschrift fur Gerontologie und Geriatrie, vol. 40, issue 5, pp. 349-356, (2007).

Shcheglova, T. et al., "Reactive immunization suppresses advanced glycation and mitigates diabetic nephropathy", Journal of the American Society of Nephrology, vol. 20, no. 5, pp. 1012-1019, (2009).
Wautier, J.-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, no. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online 5 May 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, no. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (Lama pacos) as a convenient source of recombinant camelid heavy chain antibodies (VHHs)", Journal of Immunology Methods, vol. 324, issues 1-2, pp. 13-25, (2007).
European Search Report dated September 12, 2014 for EP application number EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, November 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, CM. et al., Abstract of "T-cell aging in rheumatoid arthritis", Current Opinion in Rheumatology, vol. 26, no. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, October 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on September 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on September 17, 2014.

CERTIFICATE OF CORRECTION (continued)
U.S. Pat. No. 10,889,634 B2

"Pulmatrix demonstrates iSPERSE capabilities for inhaled dry powder delivery of antibiotics and antibodies", data presented at Respiratory Drug Delivery 2012, 3 pages, printed on September 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, no. 4, pp. 264-271, (2011).
Tchkonia, T. et al., "Cellular senescence and the senescent secretory phenotype: therapeutic opportunities", The Journal of Clinical Investigation, vol. 123, no. 3, pp. 966-972, (2013).
Kitada, K. et al., "Aldosterone induces p21-regulated apoptosis via increased synthesis and secretion of tumour necrosis factor-α in human proximal tubular cells", Clinical and Experimental Pharmacology and Physiology, vol. 39, no. 10, pp. 858-863, (2012).
Definition of "TNF inhibitor", printed from Wikipedia, the free encyclopedia on October 4, 2014, 4 pages, found at http://en.wikipedia.org/wiki/TNF_inhibitor?oldid=628250399.
Definition of "Etanercept", printed from Wikipedia, the free encyclopedia on August 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on August 11, 2014.
AbbVie, Inc., "Medication Guide for Humira", found at https://www.humira.com/rheumatoid-arthritis, 9 pages, printed on August 11, 2014.
AbbVie, Inc., "Humira: A biologic that targets and helps block TNF-alpha", found at https://www.humira.com/rheumatoid-arthritis/how-humira-works-for-ra, 8 pages, printed on August 11, 2014.
AbbVie, Inc., "How Humira (adalimumab) works video transcript", found at https://www.humira.com/rheumatoid-arthritis/how-humira-works-video-transcript, 5 pages, printed on August 11, 2014.
AbbVie, Inc., "Humira and methotrexate—a combination that has demonstrated results", found at https://www.humira.com/rheumatoid-arthritis/humira-and-methotrexate, 7 pages, printed on August 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, no. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody – Product Details", Antibodies Online, 4 pages, found at www.web.archive.org/web/20081229071154/http://www.antibodies-online.com/antibody/289931/AGEs+All+Species/, printed on December 10, 2014.
"Antibody Engineering", Fusion Antibodies, 2 pages, found at www.web.archive.org/web/20080628225818/http://www.fusionantibodies.com/index.cfm/area/information/page/engineering?, printed on December 16, 2014.

Hargreaves, R.E.G. et al., "Selective depletion of activated T cells: the CD40L-specific antibody experience", TRENDS in Molecular Medicine, vol. 10, no. 3, pp. 130-135, (2004).

Leinenga, G. et al., "Scanning ultrasound removes amyloid-β and restores memory in an Alzheimer's disease mouse model", Science Translational Medicine, vol. 7, issue 278, pp. 1-11, (2015).

Peppa, M. et al., "Glucose, advanced glycation end products, and diabetes complications: What is new and what works", Clinical Diabetes, vol. 21, no. 4, pp. 186-187, (2003).

Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).

Campisi, J. et al., "Cellular senescence: when bad things happen to good cells", Nature Reviews: Molecular Cell Biology, vol. 8, pp. 729-749, (2007).

"ALSUntangled No. 23: The Rife Machine and retroviruses", Amyotrophic Lateral Sclerosis and Frontotemporal Degeneration, vol. 15, pp. 157-159, (2014).

Roylance, D., "Mechanical properties of materials", pp. 1-128, (2008), available at www.web.mit.edu/course/3/3.225/book.pdf.

Vidarsson, G. et al., "IgG subclasses and allotypes: from structure to effector functions", Frontiers in Immunology, vol. 5, article 520, pp. 1-17, (2014).

Lin, H-T. et al., "Stem cell therapy: an exercise in patience and prudence", Philosophical Transactions of the Royal Society B: Biological Sciences 368, (2013).

Waldmann, T.A., "Immunotherapy:past, present and future", Nature Medicine, vol. 9, no. 3, pp. 269-277, (2003).

Okamoto, T. et al., "Advanced glycation end products induce angiogenesis in vivo", Microvascular Research, vol. 63, pp. 186-195, (2002).

Nagal, R. et al., "Application of monoclonal antibody libraries for the measurement of glycation adducts", Biochemical Society Transactions, vol. 31, part 6, pp. 1438-1440, (2003).

De Genst, E. et al., "Antibody repertoire development in camelids", Developmental and Comparative Immunology, vol. 30, pp. 187-198, (2006).

Griffin, L.M. et al., "Analysis of hevy and light chain sequences of conventional camelid antibodies from Camelus dromedarius and Camelus bactrianus species", Journal of Immunological Methods, vol. 405, pp. 35-46, (2014).

Hamers-Casterman, C. et al., "Naturally occurring antibodies devoid of light chains", Nature, vol. 363, pp. 446-448, (1993).

Muyldermans, S. et al., "Sequence and structure of VH domain from naturally occurring camel heavy chain immunoglobulins lacking light chains", Protein Engineering, vol. 7, no. 9, pp. 1129-1135, (1994).

Nguyen, V. K. et al., "Camel heavy-chain antibodies: diverse germline VHH and specific mechanisms enlarge the antigen-binding repertoire", The EMBO Journal, vol. 19, no. 5, pp. 921-930, (2000).

Kirstein, et al., "Advanced protein glycosylation induces transendothelial human monocyte chemotaxis and secretion of platelet-derived growth factor: roll in vascular disease of diabetes and aging", PNAS, vol. 87, no. 22, pp. 9010-9014, (1990).

Invitation to Pay Additional Fees and Partial International Search Report dated January 13, 2016 for PCT application number PCT/US2015/050154.

Feldmann, M. et al., "Anti-TNFalpha therapy of rheumatoid arthritis: What have we learned?", Annual Review of Immunology, vol. 19, pp. 163-196, (2001).

Drinda, S. et al., "Identification of the advanced glycation end products N-carboxymethyllysine in the synovial tissue of patients with rheumatoid arthritis", Annals of the Rheumatic Diseases, vol. 61, no. 6, pp. 488-492, (2002).

Ahmad, S. et al., "Preferential recognition of epitopes on AGE-IgG by the autoantibodies in rheumatoid arthritis patients", Human Immunology, vol. 74, no. 1, pp. 23-27, (2013).

Johns, L.D., "Nonthermal effects of therapeutic ultrasound: The frequency resonance hypothesis", Journal of Athletic Training, vol. 37, no. 3, pp. 293-299, (2002).

Wang, B-L. et al., "Identification of monoclonal antibody of advanced glycation end products", Chinese Journal of Arteriosclerosis, vol. 14, no. 5, pp. 409-412, (2006).

Wang, J.C. et al., "Aging and Atherosclerosis mechanisms, functional consequences, and potential therapeutics for cellular senescence", Circulation Research, vol. 111, pp. 245-259, (2012).

Minamino, T. et al., "Vascular cell senescence contribution to Atherosclerosis", Circulation Research, vol. 100, pp. 15-26, (2007).

Isoda, K. et al., "Glycated LDL increases monocyte CC chemokine receptor 2 expression and monocyte chemoattractant protein-1-mediated chemotaxis", Atherosclerosis, vol. 198, no. 2, pp. 307-312, (2008).

Roos, C.M. et al., "Chronic senolytic treatment alleviates established vasomotor dysfunction in aged or atherosclerotic mice", Aging Cell, 8 pages, (2016).

Hall, B.M. et al., "Aging of mice is associated with p16(Ink4a)- and β-galactosidase-positive macrophage accumulation that can be induced in young mice by senescent cells", Aging, vol. 8, no. 7, pp. 1-18, (2016).

Mera, K. et al., "An autoantibody against Nε-(carboxyethyl)lysine (CEL): Possible involvement in the removal of CEL-modified proteins by macrophages", Biochemical and Biophysical Research Communications, vol. 407, pp. 420-425, (2011).

Reddy, S. et al., "Nε-(Carboxymethyl)lysine is a dominant advanced glycation end product (AGE) antigen in tissue proteins". Biochemistry, vol. 34, pp. 10872-10878, (1995).

Katcher, H.L., "Studies that shed new light on aging", Biochemistry (Moscow), vol. 78, no. 9, pp. 1061-1070, (2013).

Naylor, R.M. et al., "Senescent Cells: A novel therapeutic target for aging and age-related diseases", Clinical Pharmacology & Therapeutics, vol. 93, no. 1, pp. 105-116, (2013).

Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).

Ulrich, P. et al., "Protein glycation, diabetes, and aging", Recent Progress in Hormone Research, vol. 56, pp. 1-21, (2000).

Van Heijst, J.W.J. et al., "Advanced glycation end products in human cancer tissues: detection of Nε-(carboxymethyl)lysine and argpyrimidine", Annals of the New York Academy of Sciences, vol. 1043, pp. 725-733, (2005).

Fielding, R.A. et al., "Sarcopenia: An undiagnosed condition in older adults. Current consensus definition: Prevalence, etiology, and consequences", Journal of the American Medical Directors Association, vol. 12, no. 4, pp. 249-256, (2011).

Definition of "Sarcopenia", printed from Wikipedia, the free encyclopedia on July 25, 2016, 5 pages, found at http://en.wikipedia.org/wiki/Sarcopenia.

"What is Sarcopenia?", International Osteoporosis Foundation, 2 pages, found at www.iofbonehealth.org/what-sarcopenia, (2014).

"Sarcopenia with aging", Webmd, 2 pages, found at www.webmd.com/healthy-aging/sarcopenia-with-aging, (2014).

Definition of "Keyhole limpet hemocyanin", printed from Wikipedia, the free encyclopedia on July 25, 2016, 4 pages, found at https://en.wikipedia.org/wiki/Keyhole_limpet_hemocyanin.

Cell Biolabs, Inc., "CML-BSA Product Data Sheet", 3 pages, found at http://www.cellbiolabs.com/sites/default/files/STA-314-cml-bsa.pdf, (2010).

Cell Biolabs, Inc., "CML (N-epsilon-(Caboxymethyl)Lysine) Assays and Reagents", 1 page, found at http://www.cellbiolabs.com/cml-assays, (2014).

Cruz-Jentoft, A.J. et al., "Sarcopenia: European consensus on definition and diagnosis", Age and Ageing, vol. 39, pp. 412-423, (2010).

Rolland, Y. et al., "Sarcopenia: Its assessment, etiology, pathogenesis, consequences and future perspectives", The Journal of Nutrition, Health & Aging, vol. 12, no. 7, pp. 433-450, (2008).

Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).

Definition of "N(6)-Carboxymethyllysine", printed from Wikipedia, the free encyclopedia on December 8, 2013, 1 page, found at http://en.wikipedia.org/wiki/N(6)-Carboxymethyllysine.

Definition of "Lysine", printed from Wikipedia, the free encyclopedia on December 8, 2013, 1 page, found at http://en.wikipedia.org/wiki/Lysine.

Jarvis, L.M., "Rethinking antibody-drug conjugates", Chemical & Engineering News, vol. 90, issue 25, pp. 12-18, (2012).

Mullin, R., "Cell-free approach to antibody-drug conjugates", Chemical & Engineering News, vol. 91, issue 44, 2 pages, (2013).

Thayer, A.M., "Building antibody-drug conjugates", Chemical & Engineering News, vol. 92, issue 3, pp. 13-21, (2014).

Feige, M.J. et al., "The structural analysis of shark IgNAR antibodies reveals evolutionary principles of immunoglobulins", Proceedings of the National Academy of Sciences, vol. 111, no. 22, pp. 8155-8160, (2014).

Philipot, D. et al.,"p16INK4a and its regulator miR-24 link senescence and chondrocyte terminal differentiation-associated matrix remodeling in osteoarthritis", Arthritis Research & Therapy, vol. 16, no. 1, pp. 1-12, (2014).

International Search Report and Written Opinion dated March 31, 2016 for PCT application number PCT/US2015/050154.

Zhu, Y. et al., "The achilles' heel of senescent cells: from transcriptome to senolytic drugs", Aging Cell, vol. 14, pp. 644-658, (2015).

Zhu, L. et al., "Immunization with advanced glycation end products modified low density lipoprotein inhibits atherosclerosis progression in diabetic apoE and LDLR null mice", Cardiovascular Diabetology, vol. 13, no. 151, pp. 1-12, (2014).

DeNardo, S.J. et al., "Development of tumor targeting bioprobes (111in-chimeric L6 monoclonal antibody nanoparticles) for alternating magnetic field cancer therapy", Clinical Cancer Research, vol. 11, 19 supplemental, pp. 7087s-7092s, (2005).

Chen, L. et al., "Cytolysis of human erythrocytes by a covalent antibody-selenium immunoconjugate", Free Radical Biology & Medicine, vol. 19, no. 6, pp. 713-724, (1995).

Yuan, Y. et al., "Advanced glycation end products (AGEs) increase human mesangial foam cell formation by increasing Golgi SCAP glycosylation in vitro", American Journal of Physiology-Renal Physiology, vol. 301.1, pp. F236-F243, (2011).

Hashimoto, M. et al., "Elimination of p19ARF-expressing cells enhances pulmonary function in mice", JCI Insight, vol. 1, no. 12, pp. 1-15, (2016).
Yan, S.F. et al., "Soluble RAGE: Therapy & biomarker in unraveling the RAGE axis in chronic disease and aging", Biochemical Pharmacology, vol. 79, no. 10, pp. 1379-1386, (2010).
Xue, J. et al., "Advanced glycation end product (AGE) recognition by the receptor for AGEs (RAGE)", Structure, vol. 19, no. 5, pp. 722-732, (2011).
Chang, J. et al., "Clearance of senescent cells by ABT263 rejuvenates aged hematopoietic stem cells in mice", Nature Medicine, vol. 22, no. 1, pp. 78-83, (2016).
Geiger, H., "Depleting senescent cells to combat aging", Nature Medicine, vol. 22, no. 1, pp. 23-24, (2016).
Ni, J. et al., "Plasma protein pentosidine and carboxymethyllysine, biomarkers for age-related macular degeneration", Molecular & Cellular Proteomics, vol. 8, no. 8, pp. 1921-1933, (2009).
R&D Systems, a biotechne brand, product specification of "Carboxymethyl Lysine Antibody", found at https://www.rndsystems.com/products/carboxymethyl-lysine-antibody-318003_mab3247, 1 page, (2015).
Schalkwijk, C.G. et al., "Increased accumulation of the glycoxidation product NƐ-(carboxymethyl)lysine in hearts of diabetic patients: generation and characterization of a monoclonal anti-CML antibody", Biochimica et Biophysica Acta (BBA)-Molecular and Cell Biology of Lipids, vol. 1636, no. 2, pp. 82-89, (2004).
LaPak, K.M. et al., "The molecular balancing act of p16INK4a in cancer and aging", Molecular Cancer Research, vol. 12, no. 2, pp. 167-183, (2013).
Larsen, S.A. et al., "Glucose metabolite glyoxal induces senescence in telomerase-immortalized human mesenchymal stem cells", Chemistry Central Journal, vol. 6, no. 18, pp. 1-13, (2012).
Ahmed, M.U. et al., "NƐ-(carboxymethyl)lysine, a product of the chemical modification of proteins by methylglyoxal, increases with age in human lens proteins", Biochemical Journal, vol. 324, pp. 565-570, (1997).
Dunn, J.A et al., "Age-dependent accumulation of NƐ-(Carboxymethyl)lysine and NƐ-(Carboxymethyl)hydroxylysine in human skin collagen", Biochemistry, vol. 30, pp. 1205-1210, (1991).
Finco, A.B. et al., "Generation and characterization of monoclonal antibody against advanced glycation end products in chronic kidney disease", Biochemistry and Biophysics Reports, vol. 6, pp. 142-148, (2016).
International Search Report and Written Opinion dated August 10, 2016 for PCT application number PCT/US2016/034880.
Liu, H. et al., "Abstract 154: Vaccination using advanced glycation end product of low-density lipoprotein pulsed dendritic cells reduces atherosclerosis in diabetic apoe-/- mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).
Sayej, W.N. et al., "Advanced glycation end products induce obesity and hepatosteatosis in CD-1 wild-type mice", BioMed Research International, vol. 6, no. 39, pp. 1-12, (2016).
Srikanth, V. et al., "Advanced glycation endproducts and their receptor RAGE in alzheimer's disease", Neurobiology of Aging, vol. 32, no. 5, pp. 763-777, (2011).
International Search Report and Written Opinion dated December 2, 2016 for PCT application number PCT/US2016/039076.

Fu, M-X. et al., "The advanced glycation end product, N-(Carboxymethyl)lysine, is a product of both lipid peroxidation and glycoxidation reactions", The Journal of Biological Chemistry, vol. 271, no. 17, pp. 9982-9986, (1996).
Jorgensen, L. et al., "The relationship between atherosclerosis of the thoracic aorta and renal scarring in an autopsy material", Acta Pathol Microbiol Immunol Scand A., vol. 93, no. 5, pp. 251-255, (1985) Abstract Only.
"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.
Baker, D.J. et al., "Naturally occurring p16Ink4a-positive cells shorten healthy lifespan", Nature, vol. 530, issue 7589, pp. 184-189, (2016).
Raquib, R., "The key to youth via senescent cell removal", Young Investigators Review, pp. 1-4, (2017), found at sbyireview.com/2017/01/23/the-key-to-youth-via-senescent-cell-removal.
Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.
Wiley, C., "Aging Fundamentals: Cellular senescence", Science of Aging Blog at the Buck Institute, pp. 1-4, (2015), found at sage.buckinstitute.org/aging-fundamentals-cellular-senescence.
Arichika, S. et al., "Correlation of retinal arterial wall thickness with atherosclerosis predictors in type 2 diabetes without clinical retinopathy", British Journal of Ophthalmology, vol. 101, pp. 69-74, (2017).
Lin, Z. et al., "Vaccination against AGE-LDL significant attenuates atherosclerosis in diabetic apoe mice", Heart, vol. 97, no. 21, supplement 3, p. A18, (2011) Abstract Only.
Thompson, L.V., "Age-related muscle dysfunction", Experimental Gerontology, vol. 44, pp. 106-111, (2009).
Sun, K. et al., "Elevated serum carboxymethyl-Lysine, an advanced glycation end product, predicts severe walking disability in older women: The women's health and aging study I", Journal of Aging Research, vol. 2012, pp. 1-8, (2012).
Kislinger, T. et al., "NƐ-(Carboxymethyl)Lysine adducts of proteins are ligands for receptor for advanced glycation end products that activate cell signaling pathways and modulate gene expression", The Journal of Biological Chemistry, vol. 274, no. 44, pp. 31740-31749, (1999).
Nakayama, H. et al., "Production and characterization of antibodies to advanced glycation products on proteins", Biochemical and Biophysical Research Communications, vol. 162, no. 2, pp. 740-745, (1989).
Gupta, R.K., "Aluminum compounds as vaccine adjuvants", Advanced Drug Delivery Review, vol. 32, no. 3, pp. 155-172, (1998), Abstract Only.
Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.
Koito, W. et al., "Conventional antibody against NƐ-(Carboxymethyl)Lysine (CML) shows cross-reaction to NƐ-(Carboxyethyl)Lysine (CEL): Immunochemical quantification of CML with a specific antibody", The Journal of Biochemistry, vol. 135, no. 6, pp. 831-837, (2004).
Product Description of "Anti-Advanced Glycation End Products (AGE), Carboxy-Methyl Lysine (CML) [6C7] Antibody", Kerafast, www.kerafast.com/product/1779/anti-advanced-glycation-end-products-age-carboxy-methyl-lysine-cml-6c7-antibody, printed on February 2, 2017.

Ikeda, K. et al., "NƐ-(Carboxymethyl)lysine protein adduct is a major immunological epitope in proteins modified with advanced glycation end products of the maillard reaction", Biochemistry, vol. 35, no. 24, pp. 8075-8083, (1996).
Dunn, J.A. et al., "Oxidation of glycated proteins: Age-dependent accumulation of NƐ-(Carboxymethyl)lysine in lens proteins", Biochemistry, vol. 28, no. 24, pp. 9464-9468, (1989).
Peppa, M. et al., "The role of advanced glycation end products in the development of atherosclerosis", Current Diabetes Reports, vol. 4, pp. 31-36, (2004).
Glenn, J.V. et al., "The role of advanced glycation end products in retinal ageing and disease", Biochimica Et Biophysica Acta, vol. 1790, no. 10. Pp. 1109-1116, (2009).
European Search Report dated February 21, 2017 for EP application number 16198527.0.
Xu, M. et al., "Transplanted senescent cells induce an osteoarthritis-like condition in mice", The Journals of Gerontology Series A: Biological Sciences and Medical Sciences, pp. 1-6, (2016).
Ratliff, M. et al., "In senescence, age-associated B cells secrete TNFα and inhibit survival of B-cell precursors", Aging Cell, vol. 12, pp. 303-311, (2013).
Manestar-Blazic, T. et al., "The dynamic of senescent cells accumulation can explain the age-specific incidence of autoimmune diseases", Medical Hypotheses, vol. 73, pp. 667-669, (2009).
Tchkonia, T. et al., "Fat tissue, aging, and cellular senescence", Aging Cell, vol. 9, pp. 667-684, (2010).
Robbins, P. et al., "Scripps research, Mayo Clinic scientists find new class of drugs that dramatically increases healthy lifespan", The Scripps Research Institute, pp. 1-3, found at www.scripps.edu/news/press/2015/20150309agingcell.html, printed on March 14, 2015.
Dorr, J.R. et al., "Synthetic lethal metabolic targeting of cellular senescence in cancer therapy", Nature, vol. 501, no. 7467, pp. 421-425, (2013).
Xu, M. et al., "Targeting senescent cells enhances adipogenesis and metabolic function in old age", eLife, vol. 4, pp. 1-20, (2015).
Minamino, T. et al., "Endothelial cell senescence in human atherosclerosis: Role of telomere in endothelial dysfunction", Circulation, vol. 105, issue 13, pp. 1541-1544, (2002).
Takino, J-I. et al., "Cancer malignancy is enhanced by glyceraldehyde-derived advanced glycation end-products", Journal of Oncology, vol. 2010, pp. 1-8, (2010).
Laberge, R-M. et al., "Epithelial-mesenchymal transition induced by senescent fibroblasts", Cancer Microenvironment, vol. 5, pp. 39-44, (2012).
Abe, R. et al., "Regulation of human melanoma growth and metastasis by AGE-AGE receptor interactions", Journal of Investigative Dermatology, vol. 122, no. 2, pp. 461-467, (2004).
Porporato, P.E. et al., "A mitochondrial switch promotes tumor metastasis", Cell Reports, vol. 8, pp. 754-766, (2014).
Boquio, A. et al., "Reversible cell cycle inhibition and premature aging features imposed by conditional expression of p16ink4a", Aging Cell, vol. 14, pp. 139-147, (2015).
Nelson, G. et al., "A senescent cell bystander effect: senescence-induced senescence", Aging Cell, vol. 11, pp. 345-349, (2012).
Rayess, H. et al., "Cellular senescence and tumor suppressor gene p16", International Journal of Cancer, vol. 130, no. 8, pp. 1715-1725, (2012).
Greenfieldboyce, N., "Boosting life span by clearing out cellular clutter", NPR.ORG, 4 pages, found at www.npr.org/sections/health-shots/2016/02/03/465354874/boosting-lifespan-by-clearing-out-cellular-clutter, printed on February 4, 2016.
Matus, D.Q. et al., "Invasive cell fate requires G1 cell-cycle arrest and histone deacetylase-mediated changes in gene expression", Developmental Cell, vol. 35, pp. 162-174, (2015).

Stony Brook University, "Targeting invasive cells not dividing cells to halt cancer, study suggests", ScienceDaily, pp. 1-2, found at www.sciencedaily.com/releases/2015/10/151026181610.htm, (2015).
Liu, D. et al., "Senescent human fibroblasts increase the early growth of xenograft tumors via matrix metalloproteinase secretion", Cancer Research, vol. 67, no. 7, pp. 3117-3126, (2007).
Hoke, Z. "Belgian researchers discover way to block cancer metastasis", VOZ News, pp. 1-3, found at www.voanews.com/a/belgian-researchers-discover-way-to-block-cancer-metastasis/2453790.html, (2014).
Di, G-H. et al., "IL-6 secreted from senescent mesenchymal stem cells promotes proliferation and migration of breast cancer cells", PloS one, vol. 9, no. 11, pp. 1-15, (2014).
Huang, L-W. et al., "P16ink4a overexpression predicts lymph node metastasis in cervical carcinomas", Journal of Clinical Pathology, vol. 65, pp. 117-121, (2012).
Romagosa, C. et al., "P16ink4a overexpression in cancer: a tumor suppressor gene associated with senescence and high-grade tumors", Oncogene, vol. 30, pp. 2087-2097, (2011).
Terman, A. et al., "Mitochondrial turnover and aging of long-lived postmitotic cells: The mitochondrial-lysosomal axis theory of aging", Antioxidants & Redox Signaling, vol. 12, no. 4, pp. 503-535, (2010).
Ralph, A. et al., "P16 and HPV discordance in metastatic carcinoma of cervical lymph nodes of unknown primary", Clinical Case Reports, vol. 3, no. 10, pp. 817-818, (2015).
Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).
Bakala, H. et al., "Changes in rat liver mitochondria with aging Ion protease-like activity and NƐ-carboxymethyllysine accumulation in the matrix", European Journal of Biochemistry, vol. 270, no. 10, pp. 2295-2302, (2003).
Leslie, M. "Suicide of aging cells prolongs life span in mice", Sciencemag.org, pp. 1-4, found at www.sciencemag.org/news/2016/02/suicide-aging-cells-prolongs-life-span-mice, (2016).
Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).
May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).
Schmitt, C.A. "Cellular senescence and cancer treatment", Biochimica et Biophysica Acta – Reviews on Cancer, vol. 1775, no. 1, pp. 5-20, (2007).
Gordon, R.R. et al., "Cellular senescence and cancer chemotherapy resistance", Drug Resistance Updates, vol. 15, no. 1-2, pp. 123-131, (2012).
Eyman, D. et al., "CCL5 secreted by senescent aged fibroblasts induces proliferation of prostate epithelial cells and expression of genes that modulate angiogenesis", Journal of Cellular Physiology, vol. 220, no. 2, pp. 376-381, (2009).
Nguyen, D.X. et al., "Metastasis: from dissemination to organ-specific colonization", Nature Reviews Cancer, vol. 9, no. 4, pp. 274-284, (2009).
Smit, M.A. et al., "Deregulating EMT and senescence: Double impact by a single twist", Cancer Cell, pp. 5-7, (2008).
Degenhardt, T.P. et al., "Chemical modification of proteins by methylglyoxal", Cellular and Molecular Biology (Noisy-le-Grand, France), vol. 44, no. 7, pp. 1139-1145, (1998) Abstract Only.

Gao, S.H. et al., "Monoclonal antibody humanness score and its applications", BMC Biotechnology, vol. 13, no. 1, pp. 1-12, (2013).
ClinicalTrials.gov, "A study evaluating the safety of ABT-263 in combination with etoposide/cisplatin in subjects with cancer", ClinicalTrials.gov, 4 pages, found at https://clinicaltrials.gov/ct2/show/NCT00878449?term=A+study+evaluating+the+safety+of+ABT-263+in+combination+with+etoposide%2Fcisplatin+in+subjects+with+cancer&rank=1, printed on August 4, 2016.
Keating, D.J. "Mitochondrial dysfunction, oxidative stress, regulation of exocytosis and their relevance to neurodegenerative diseases", vol. 104, no. 2, pp. 298-305, (2008). Abstract Only
Sas, K. et al., "Mitochondria, metabolic disturbances, oxidative stress and the kynurenine system, with focus on neurodegenerative disorders", Journal of the neurological sciences, vol. 257, no. 1, pp. 221-239, (2007). Abstract Only
Ott, M. et al., "Mitochondria, oxidative stress and cell death", Apoptosis, vol. 12, no. 5, pp. 913-922, (2007). Abstract Only
Trushina, E. et al., "Oxidative stress and mitochondrial dysfunction in neurodegenerative diseases", Neuroscience, vol. 145, no. 4, pp. 1233-1248, (2007). Abstract Only
Moreira, P.I. et al., "Lipoic acid and N-acetyl cysteine decrease mitochondrial-related oxidative stress in Alzheimer disease patient fibroblasts", Journal of Alzheimer's Disease, vol. 12, no. 2, pp. 195-206, (2007). Abstract Only
Yel, L. et al., "Thimerosal induces neuronal cell apoptosis by causing cytochrome c and apoptosis-inducing factor release from mitochondria", International Journal of Molecular Medicine, vol. 16, no. 6, pp. 971-977, (2005). Abstract Only
Humphrey, M.L. et al., "Mitochondrial mediated thimerosal-induced apoptosis in a human neuroblastoma cell line (SK-N-SH)", Neurotoxicology, vol. 26, no. 3, pp. 407-416, (2005). Abstract Only
Makani, S. et al., "Biochemical and molecular basis of thimerosal-induced apoptosis in T cells: a major role of mitochondrial pathway", Genes and Immunity, vol. 3, no. 5, pp. 270-278, (2002). Abstract Only
Freitag, H. et al., "Inhibition of malate transport and activation of phosphate transport in mitochondria by ethylmercurithiosalicylate", FEBS Letters, vol. 117, no. 1, pp. 149-151, (1960). Citation Only
Freitag, H. et al., "Ethylmercurithiosalicylate—a new reagent for the study of phosphate transport in mitochondria", FEBS Letters, vol. 114, no. 2, pp. 295-298, (1980). Citation Only
Windham, G.C. et al., "Autism spectrum disorders in relation to distribution of hazardous air pollutants in the San Francisco bay area", Environmental Health Perspectives, pp. 1438-1444, (2006). Citation Only
Ooe, H. et al., "Induction of reactive oxygen species by bisphenol A and abrogation of bisphenol A-induced cell injury by DJ-1", Toxicological Sciences, vol. 88, no. 1, pp. 114-126, (2005). Abstract Only
Hanzel, C.E. et al., "Thallium induces hydrogen peroxide generation by impairing mitochondrial function", Toxicology and Applied Pharmacology, vol. 216, no. 3, pp. 485-492, (2006). Abstract Only
Murugavel, P. et al., "Cadmium induced mitochondrial injury and apoptosis in vero cells: protective effect of diallyl tetrasufide from garlic", The International Journal of Biochemistry & Cell Biology, vol. 39, no. 1, pp. 161-170, (2007). Abstract Only
Lasfer, M. et al., "Cadmium induces mitochondria-dependent apoptosis of normal human hepatocytes", Cell Biology and Toxicology, vol. 24, no. 1, pp. 55-62, (2008). Abstract Only Gash, D.M. et al., Trichloroethylene: Parkinsonism and complex 1 mitochondrial neurotoxicity", Annals of neurology, vol. 63, no. 2, pp. 184-192, (2008). Abstract Only Banerjee, N. et al., "Arsenic-induced mitochondrial instability leading to programmed cell death in the exposed individuals", Toxicology, vol. 246, no. 2, pp. 101-111, (2008). Abstract Only Partridge, M.A. et al., "Arsenic induced mitochondrial DNA damage and altered mitochondrial oxidative function: Implication for genotoxic mechanisms in mammalian cells", Cancer Research, vol. 67, no. 11, pp. 5239-5247, (2007). Abstract Only Santra, A. et al., "Arsenic induces apoptosis in mouse liver is mitochondria dependent and is abrogated by N-acetylcysteine", Toxicology and Applied Pharmacology, vol. 220, no. 2, pp. 146-155, (2007). Abstract Only Bouchard, H. et al., "Antibody-drug conjugates-A new wave of cancer drugs", Bioorganic & Medicinal Chemistry Letters, vol. 24, pp. 5357-5363, (2014).

Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).

Childs, B.G. et al., "Senescent intimal foam cells are deleterious at all stages of atherosclerosis", Science, vol. 354, no. 6311, pp. 472-477, (2016).

Loaiza, N. et al., "Cellular senescence and tumor promotion: Is aging the key?", Biochimica et Biophysica Acta, vol. 1865, pp. 155-167, (2016).

Rodier, F. et al., "Four faces of cellular senescence", The Journal of Cell Biology, vol. 192, no. 4, pp. 547-556, (2011).

Shay, J.W. et al., "Hallmarks of senescence in carcinogenesis and cancer therapy", Oncogene, vol. 23, pp. 2919-2933, (2004).

Davalos, A.R. et al., "Senescent cells as a source of inflammatory factors for tumor progression", Cancer Metastasis Reviews, vol. 29, pp. 273-283, (2010).

Roninson, I.B., "Tumor cell senescence in cancer treatment", Cancer Research, vol. 63, pp. 2705-2715, (2003).

International Search Report and Written Opinion dated May 17, 2017 for PCT application number PCT/US2017/018185.

Kobayashi, S. et al., "Overproduction of N(epsilon) – (carboxymethyl) lysine-induced neovascularization in cultured choroidal explant of aged rat", Biological & Pharmaceutical Bulletin, vol. 30, no. 1, pp. 133-138, (2007).

Foster, D. et al., "AGE metabolites: A biomarker linked to cancer disparity?" Cancer Epidemiology, Biomarkers and Prevention, vol. 23, no. 10, pp. 2186-2191, (2014).

Mir, A.R. et al., "Structural changed in histone H2A by methylglyoxal generate highly immunogenic amorphous aggregates with implications in auto-immune response in cancer", Glycobiology, vol. 26, no. 2, pp. 129-141, (2016).

Ko, S-Y. et al., "Cell migration is regulated by AGE-RAGE interaction in human oral cancer cells in vitro", PLOS One, vol. 9, no. 10, pp. 1-9, e0110542, (2014).

Chen, H. et al., "Advanced glycation end products increase carbohydrate responsive element binding protein expression and promote cancer cell proliferation", Molecular and Cellular Endocrinology, vol. 395, no. 1-2, pp. 69-78, (2014).

Mercado-Pimentel, M.E. et al., The S100P/RAGE signaling pathway regulates expression of microRNA-21 in colon cancer cells", FEBS Letters, vol. 589, no. 18, pp. 2388-2393, (2015).

Product description, "Carboxymethyl Lysine Antibody", R&D Systems, a biotechne brand, catalog number MAB3247, 1 page, found at https://resources.mdsystems.com/pdfs/datasheets/mab3247.pdf, (2015).

Bhat, R. et al., "Astrocyte senescence as a component of Alzheimer's Disease", PLOS One, vol. 7, no. 9, pp. 1-10, (2012).

Flanary, B.E. et al., "Evidence that aging and amyloid promote microglial cell senescence", Rejuvenation Research, vol. 10, no. 1, pp. 61-74, (2007).

Takeda, A. et al., "Advanced glycation end products co-localize with astrocytes and microglial cells in Alzheimer's disease brain", Acta Neuropathologica, vol. 95, pp. 555-558, (1998).

Chinta, S.J. et al., "Environmental stress, ageing and glial cell senescence: a novel mechanistic link to Parkinson's disease?", Journal of Internal Medicine, vol. 273, pp. 429-436, (2013).

Mori, M., The Parkinsonian Brain: Cellular senescence and neurodegeneration", SAGE, found at sage.buckinstitute.org/the-parkinsonian-brain-cellular-senescence-and-neurodegeneration, (2015).

Das, M.M. et al., "Astrocytes show reduced support of motor neurons with aging that is accelerated in a rodent model of ALS", Neurobiology of Aging, vol. 36, pp. 1130-1139, (2015).

Luessi, F. et al., "Neurodegeneration in multiple sclerosis: novel treatment strategies", Expert Review of Neurotherapeutics, vol. 12, no. 9, pp. 1061-1077, (2012).

Wright, W.E., "Myoblast senescence in Muscular Dystrophy", Experimental Cell Research, vol. 157, pp. 343-354, (1985).

King, O.D., et al., The tip of the iceberg: RNA-binding proteins with prion-like domains in neurodegenerative disease", Brain Research, vol. 1462, pp. 61-80, (2012).

Dobson, D.M., "The structural basis of protein folding and its links with human disease", Philosophical Transactions of the Royal Society of London B: Biological Sciences, vol. 356, no. 1406, pp. 133-145, (2001).

Kato, S. et al., "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation", Acta Neuropathologica, vol. 100, pp. 490-505, (2000).

International Search Report and Written Opinion dated September 29, 2017 for PCT application number PCT/US2017/027773.

Capparelli, C. et al., "Autophagy and senescence in cancer-associated fibroblasts metabolically supports tumor growth and metastasis via glycolysis and ketone production", Cell Cycle, vol. 11, no. 12, pp. 2285-2302, (2012).

""Shelf life" of blood? Shorter than we think", Johns Hopkins Medicine, pp. 1-2 found at www.hopkinsmedicine.org/news/media/releases/shelf_life_of_blood_shorter_than_we_think, (2013).

Garay-Sevilla, M.E. et al., "Advanced glycosylation end products in skin, serum, saliva and urine and its association with complications of patients with Type 2 diabetes mellitus", Journal of Endocrinological Investigation, vol. 28, no. 5, pp. 223-230, (2005).

Joyal, S.V., "Aging and Glycation", Life Extension Magazine, issue 4, pp. 1-7, found at www.lifeextension.com/Magazine/2008/4/Aging-And-Glycation/Page-01, (2008)

Egberts, J-H. et al., "Anti-tumor necrosis factor therapy inhibits pancreatic tumor growth and metastasis", Cancer Research, vol. 68, pp. 1443-1450, (2008).

Lowe, R. et al., "Buccals are likely to be a more informative surrogate tissue than blood for epigenome-wide association studies", Epigenetics, vol. 8, no. 4, pp. 445-454, (2013).

Bian, C. et al., "Clinical outcome and expression of mutant P53, P16, and Smad4 in lung adenocarcinoma: a prospective study", World Journal of Surgical Oncology, vol. 13, no. 128, pp. 1-8, (2015).

Tape, C.J. et al., "Oncogenic KRAS regulates tumor cell signaling via stromal reciprocation", Cell, vol. 165, pp. 910-920, (2016).

Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on August 16, 2017.

Warrington, K.J. et al., "CD28 loss in senescent CD4+ T cells: reversal by interleukin-12 stimulation", Blood, vol. 101, no. 9, pp. 3543-3549, (2003).

Kared, H. et al., "CD57 in human natural killer cells and T-lymphocytes", Cancer Immunology, Immunotherapy, vol. 65, issue 4, pp. 441-452, (2016).

Li, Z. et al., "Cdkn2a suppresses metastasis in squamous cell carcinomas induced by the gain-of-function mutant p53R172H", The Journal of Pathology, vol. 240, issue 2, pp. 224-234, (2016). (Abstract Only).

Demaria, M. et al., "Cellular senescence promotes adverse effects of chemotherapy and cancer relapse", Cancer Discovery, vol. 7, pp. 165-176, (2017).

Niu, L. et al., "Free and protein-bound Nε-carboxymethyllysine and Nε-carboxyethyllysine in fish muscle: Biological variation and effects of heat treatment", Journal of Food Composition and Analysis, vol. 57, pp. 56-63, (2017).

Yoon, M-S. et al., "Characterisation of advanced glycation endproducts in saliva from patients with diabetes mellitus", Biochemical and Biophysical Research Communications, vol. 323, issue 2, pp. 377-381, (2004).

Product description for "Carboxymethyl Lysine (CML) ELISA", Kamiya Biomedical Company, pp. 1-7, found at www.k-assay.com/pdf/KT-32428.pdf, printed on August 16, 2017.

Baar, M.P. et al., "Targeted apoptosis of senescent cells restores tissue homeostasis in response to chemotoxicity and aging", Cell, vol. 169, pp 132-147, (2017).

Kim, Y.H. et al., "Senescent tumor cells lead the collective invasion in thyroid cancer", Nature Communications, pp. 1-14, (2017).

Ciccone, T.G. et al., "Reversing OA-new treatment on the horizon", Practical Pain Management, pp. 1-5, found at www.practicalpainmanagement.com/resources/news-and-research/reversing-oa-new-treatment-horizon, printed on August 17, 2017.

Cook, L.S., "Learning about blood component therapy", Nursing, vol. 39, no. 4, pp. 30-33, (2009).

Landesberg, R. et al., The expression of the receptor for glycation endproducts (RAGE) in oral squamous cell carcinomas", Oral Surgery Oral Medicine Oral Pathology Oral Radiology, vol. 105, issue 5, pp. 617-624, (2008).

Zhou, H.W., "Recovery of function in osteoarthritic chondrocytes induced by p16INK4a-specific siRNA in vitro", Rheumatology, vol. 43, pp. 555-568, (2004).

Fuijkschot, W.W. et al., "Prevention of age-induced N(ε)-(carboxymethyl)lysine accumulation in the microvasculature", European Journal of Clinical Investigation, vol. 46, issue 4, pp. 334-341, (2016). (Abstract Only).

Rasheed, Z.A. et al., "Pathology of pancreatic stroma in PDAC", Pancreatic Cancer and Tumor Microenvironment, pp. 1-10, (2012).

Morton, J.P. et al., "Mutant p53 drives metastasis and overcomes growth arrest/senescence in pancreatic cancer", PNAS, vol. 107, no. 1, pp. 246-251, (2010).

Verzijl, N. et al., "AGEing and osteoarthritis: a different perspective", Current Opinion in Rheumatology, vol. 15, issue 5, pp. 616-622, (2003).

Frescas, D. et al., "Senescent cells expose and secrete an oxidized form of membrane-bound vimentin as revealed by a natural polyreactive antibody", PNAS, vol. 114, no. 9, pp. E1668-E1677, (2017).

Oren, M. et al., "Mutant p53 gain-of-function in cancer", Cold Spring Harbor Perspectives in Biology, vol. 2, pp. 1-15, (2010).

"Senescence promotes chemotherapy side effects and cancer relapse", Medical Xpress, pp. 1-4, found at https://m.medicalxpress.com/news/2017-01-senescence-chemotherapy-side-effects-cancer.html, (2017).

Oh, J. et al., "Local clearance of senescent cells attenuates the development of post-traumatic osteoarthritis and creates a pro-regenerative environment", Nature Medicine, vol. 23, no. 6, pp. 1-9, (2017).

Protocols for "Isolation of untouched human T cells from peripheral blood mononuclear cells (PBMC)", Thermo Fisher Scientific, pp. 1-4, found at www.thermofisher.com/us/en/home/references/ protocols/proteins-expression-isolation-and-analysis/cell-separation-methods/human-cell-separation-protocols/isolation-of-untouched-human-t-cells-.html, printed on August 17, 2017.

Henrich, C.J. et al., "Isolation and characterization of a glycopeptide from human senescent erythrocytes", Carbohydrate Research, vol. 120, pp. 55-66, (1983).

Tsai, K.K.C. et al., "Low-dose radiation-induced senescent stromal fibroblasts render nearby breast cancer cells radioresistant", Radiation Research, vol. 172, pp. 306-313, (2009).

Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).

Garcia-Matas, S. et al., "Dysfunction of astrocytes in senescence-accelerated mice SAMP8 reduces their neuroprotective capacity", Aging Cell, vol. 7, pp. 630-640, (2008).

Danysz, W. et al., "Alzheimer's disease, β-amyloid, glutamate, NMDA receptors and memantine-searching for the connections", British Journal of Pharmacology, vol. 167, pp. 324-352, (2012).

Blasko, I. et al., "Glial cells: Astrocytes and oligodendrocytes during normal brain aging", Encyclopedia of Neuroscience, pp. 743-747, (2009).

Leonard, B.W. et al., "Subventricular zone neural progenitors from rapid brain autopsies of elderly subjects with and without neurodegenerative disease", The Journal of Comparative Neurology, vol. 515, pp. 269-294, (2009).

Louveau, A. et al., "Structural and functional features of central nervous system lymphatic vessels", Nature, vol. 523, issue 7560, pp. 337-341, (2015).

Torgan, C., "Lymphatic vessels discovered in central nervous system", NIH Research Matters, pp. 1-4, found at www.nih.gov/news-events/nih-research-matters/lymphatic-vessels-discovered-central-nervous-system, June 15, 2015.

Boskovitz, A. et al., "Monoclonal antibodies for brain tumour treatment", Expert Opinion on Biological Therapy, vol. 4, no. 9, pp. 1453-1471, (2004).

Takami, A. et al., Treatment of primary central nervous system lymphoma with induction of complement-dependent cytotoxicity by intraventricular administration of autologous-serum-supplemented rituximab", Cancer Science, vol. 97, no. 1, pp. 80-83, (2006).

Biran, A. et al., "Senescent cells communicate via intercellular protein transfer", Genes & Development, vol. 29, pp. 791-802, (2015).

Golde, T.E. et al., "Proteinopathy-induced neuronal senescence: a hypothesis for brain failure in Alzheimer's and other neurodegenerative diseases", Alzheimer's Research & Therapy, vol. 1, no. 2, pp. 1-12, (2009).

Ouroboros, "Sweet madness: Sporadic prion disease and age-related changes in protein glycosylation", Research in the Biology of Aging, pp. 1-4, found at https://ouroboros.wordpress.com/

2006/12/14/sweet-madness-sporadic-prion-disease-and-age-related-changes-in-protein-glycosylation/, (2006).

Xellbiogene, "Amyotrophic lateral sclerosis, immunotherapy is offering some hope", Xellbiogene.com, pp. 1-3, (2014).

Definition of "Complement system" printed from Wikipedia, the free encyclopedia on August 4, 2015 found at http://en.wikipedia.org/wiki/Complement_system.

Definition of "Ventricular system" printed from Wikipedia, the free encyclopedia on October 30, 2017 found at http://en.wikipedia.org/wiki/Ventricular_system.

Urushitani, M., "Future perspectives of immunotherapy against ALS", Rinsho Shinkeigaku, vol. 49, no. 11, pp. 818-820, (2009). (Abstract Only)

Cabezas, I.L. et al., "The role of glial cells in Alzheimer disease: potential therapeutic implications", Neurologia, vol. 29, no. 5, pp. 305-309, (2014).

Definition of "Prion" printed from Wikipedia, the free encyclopedia on November 17, 2015 found at http://en.wikipedia.org/wiki/Prion. "Prion Diseases", National Institute of Allergy and Infectious Diseases, pp. 1-2, found at www.niaid.nih.gov/diseases-conditions/prion-diseases, printed on October 30, 2017.

"Alzheimer basics: Plaques and tangles", ALZ.org, pp. 1-2, found at www.alz.org/norcal/in_my_community_20545.asp, printed on November 17, 2015.

Definition of "Lewy body" printed from Wikipedia, the free encyclopedia on November 17, 2015 found at http://en.wikipedia.org/wiki/Lewy_body.

Definition of "Myocyte" printed from Wikipedia, the free encyclopedia on November 17, 2015 found at http://en.wikipedia.org/wiki/Myocyte.

Definition of "Myosatellite cell" printed from Wikipedia, the free encyclopedia on November 17, 2015 found at http://en.wikipedia.org/wiki/Myosatellite_cell.

Definition of "Microglia" printed from Wikipedia, the free encyclopedia on October 30, 2017 found at http://en.wikipedia.org/wiki/Microglia.

Definition of "Astrocyte" printed from Wikipedia, the free encyclopedia on October 30, 2017 found at http://en.wikipedia.org/wiki/Astrocyte.

Ouroboros, "A role for microglial senescence in Alzheimer's?", Research in the Biology of Aging, pp. 1-3, found at https://ouroboros.wordpress.com/?s=a+role+for+microglial, (2007).

Chen, K.S. et al., "Monoclonal antibody therapy for malignant glioma", Glioma: Immunotherapeutic Approaches, chapter 10, pp. 121-141, (2012).

Reardon, S., "Alzheimer's drug sneaks through blood-brain barrier", Nature News, pp. 1-4, (2014).

"Astrocytes as a novel target in Alzheimer's disease", Expertsvar, pp. 1-2, (2012).

Myslinski, N., "Alzheimer's disease and the blood-brain barrier", Today's Geriatric Medicine, vol. 7, no. 1, pp. 1-10, (2014).

Hutter-Saunders, J.A.L. et al., "Pathways towards an effective immunotherapy for Parkinson's disease", Expert Reviews in Neurotherapeutics, vol. 11, no. 12, pp. 1703-1715, (2011).

Definition of "Intrathecal administration" printed from Wikipedia, the free encyclopedia on October 30, 2017 found at http://en.wikipedia.org/wiki/Intrathecal_administration.

"What is ALS?", ALSA.org, found at www.alsa.org/2015-non-responsive-pages/about-als/what-is-als.html, printed on March 31, 2016.

Rouger, K. et al., "Systemic delivery of allogenic muscle stem cells induces long-term muscle repair and clinical efficacy in Duchenne muscular dystrophy dogs", The American Journal of Pathology, vol. 179, no. 5, pp. 2501-2518, (2011).

Anderson, J.L. et al., "Brain function in Duchenne muscular dystrophy", Brain, vol. 125, pp. 4-13, (2002).
Jarius, S. et al., "AQP4 antibodies in neuromyelitis optica: diagnostic and pathogenetic relevance", Nature Reviews, vol. 6, pp. 383-392, (2010).
Wesolowski, J. et al., "Single domain antibodies: promising experimental and therapeutic tools in infection and immunity", Medical Microbiology and Immunology, vol. 198, pp. 157-174, (2009).
Definition of "Antibody" printed from Wikipedia, the free encyclopedia on September 21, 2015 found at http://en.wikipedia.org/wiki/Antibody.
Definition of "Antibody-dependent cell-mediated cytotoxicity" printed from Wikipedia, the free encyclopedia on December 28, 2015 found at http://en.wikipedia.org/wiki/Antibody-dependent_cell-mediated_cytotoxicity.
Definition of "Blocking antibody" printed from Wikipedia, the free encyclopedia on December 28, 2015 found at http://en.wikipedia.org/wiki/Blocking_antibody.
Definition of "Fc receptor" printed from Wikipedia, the free encyclopedia on December 28, 2015 found at http://en.wikipedia.org/wiki/Fc_receptor.
Definition of "Fragment crystallizable region" printed from Wikipedia, the free encyclopedia on December 28, 2015 found at http://en.wikipedia.org/wiki/Fragment_crystallizable_region.
Definition of "Neutralizing antibody" printed from Wikipedia, the free encyclopedia on December 28, 2015 found at http://en.wikipedia.org/wiki/Neutralizing_antibody.
Company Information on "NantKwest", pp. 1-4, found at www.nantkwest.com, printed on April 1, 2016.
Forbes, J.M. et al., "Below the radar: Advanced glycation end products that detour "around the side"", Clinical Biochemist Reviews, vol. 26, pp. 123-134, (2005).
Paul, W.E., "Fundamental immunology, third edition", Raven Press New York, chapter 9, pp. 292-295, (1993).
Rudikoff, S. et al., "Single amino acid substitution altering antigen-binding specificity", Proceedings of the National Academy of Science USA, vol. 79, pp. 1979-1983, (1982).
Wu, H. et al., "Humanization of a murine monoclonal antibody by simultaneous optimization of framework and CDR residues", Journal of Molecular Biology, vol. 294, pp. 151-162, (1999).
Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).
Tang, S-S. et al., "Reaction of aortic lysyl oxidase with β-Aminopropionitrile", The Journal of Biological Chemistry, vol. 258, no. 7, pp. 4331-4338, (1983).
Saito, H. et al., "Regulation of a novel gene encoding a lysyl oxidase-related protein in cellular adhesion and senescence", The Journal of Biological Chemistry, vol. 272, no. 13, pp. 8157-8160, (1997).
Choi, Y-G. et al., "Nε-carboxymethyl modification of lysine residues in pathogenic prion isoforms", Molecular Neurobiology, vol. 53, pp. 3102-3112, (2016).
Wendel, U. et al., "A novel monoclonal antibody targeting carboxymethyllysine, an advanced glycation end product in atherosclerosis and pancreatic cancer", PLoS One, vol. 13, no. 2, pp. 1-22, (2018).
Hsia, T-C. et al., "Carboxymethyllysine, an advanced glycation end-product, promotes the invasion and migration of lung cancer A549 cells", Clinical Medicine Research, vol. 6, no. 5, pp. 149-156, (2017).
Nowotny, K. et al., "Advanced glycation end products and oxidative stress in type 2 diabetes mellitus", Biomolecules, vol. 5, pp. 194-222, (2015).

Yun, M.H. et al., "Recurrent turnover of senescent cells during regeneration of a complex structure", eLIFE, elifesciences.org, pp. 1-16, (2015).

Barja, G., "Aging in vertebrates, and the effect of caloric restriction: a mitochondrial free radical production-DNA damage mechanism?", Biological Reviews, vol. 79, no. 2, pp. 235-251, (2004). Abstract Only Pamplona, R. et al., "Aging increases nepsilon-(carboxymethyl)lysine and caloric restriction decreases nepsilon-(carboxyethyl)lysine and nepsilon-(malondialdehyde)lysine in rat heart mitochondrial proteins", Free Radical Research, vol. 36, no. 1, pp. 47-54, (2002). Abstract Only Yun, M.H., "Cellular senescence in regeneration", The Node, pp. 1-8, found at http://thenode.biologists.com/cellular-senescence-in-regeneration/research/, June 28, 2015.

Kasper, M. et al., "Age-related changes in cells and tissues due to advanced glycation end products (AGEs)", Archives of Gerontology and Geriatrics, vol. 32, issue 3, pp. 233-243, (2001).

Wang, Z. et al., "Advanced glycation end-product NƐ-carboxymethyl-Lysine accelerates progression of atherosclerotic calcification in diabetes", Atherosclerosis, vol. 221, issue 2, pp. 387-396, (2012). Abstract Only Draber, P. et al., "Stability of monoclonal IgM antibodies freeze-dried in the presence of trehalose", Journal of Immunological Methods, vol. 181, issue 1, pp. 37-43, (1995).

Kesari, S. et al., "Pritumumab binding to glioma cells induces ADCC and inhibits tumor growth", Journal of Clinical Oncology, vol. 35, no. 15 Supplemental, e14004-e14004, (2017). Abstract Only Babic, I. et al., "Pritumumab, the first therapeutic antibody for glioma patients", Human Antibodies, vol. 26, no. 2, pp. 95-101, (2017). Abstract Only Riva, P. et al., "Treatment of intracranial human glioblastoma by direct intratumoral administration of 131I-labelled anti-tenascin monoclonal antibody BC-2", International Journal of Cancer, vol. 51, no. 1, pp. 7-13, (1992). Abstract Only Ruster, M. et al., "Detection of elevated NƐ-carboxymethyllysine levels in muscular tissue and in serum of patients with fibromyalgia", Scandinavian Journal of Rheumatology, vol. 34, issue 6, pp. 460-463, (2005). Abstract Only Niwa, H. et al., "Accelerated formation of NƐ-(carboxymethyl) lysine, an advanced glycation end product, by glyoxal and 3-deoxyglucosone in cultured rat sensory neurons", Biochemical and Biophysical Research Communications, vol. 248, issue 1, pp. 93-97, (1998). Abstract Only Daly, C. et al., "Monocyte chemoattractant protein-1 (CCL2) in inflammatory disease and adaptive immunity: Therapeutic opportunities and controversies", Microcirculation, vol. 10, pp. 247-257, (2003).

Lee, S.T. et al., "Decreased number and function of endothelial progenitor cells in patients with migraine", Neurology, vol. 70, no. 17, pp. 1510-1517, (2008). Abstract Only Brown, J.N. et al., "Class effect of erythropoietin therapy on hemoglobin A1c in a patient with diabetes mellitus and chronic kidney disease not undergoing hemodialysis", Pharmacotherapy, The Journal of Human Pharmacology and Drug Therapy, vol. 29, no. 4, pp. 468-472, (2009). Abstract Only Liu, J. et al., "Accelerated senescence of renal tubular epithelial cells is associated with disease progression of patients with immunoglobulin A (IgA) nephropathy", Translational Research, vol. 159, issue 6, pp. 454-463, (2012). Abstract Only Khaw, K-T. et al., "Association of hemoglobin A1c with cardiovascular disease and mortality in adults: The European prospective investigation into cancer in Norfolk", Annals of Internal Medicine, vol. 141, pp. 413-420, (2004).

Kohnert, K.D. et al., "Destruction of pancreatic beta cells in rats by complete Freund's adjuvant combined with non-diabetogenic doses of streptozotocin", Diabetes Research, vol. 5, no. 1, pp. 1-11, (1987). Abstract Only Staud, R., "Fibromyalgia pain: do we know the source?", Current Opinion in Rheumatology, vol. 16, issue 2, pp. 157-163, (2004). Abstract Only Fleurence, J. et al., "Targeting and killing glioblastoma with monoclonal antibody to O-acetyl GD2 ganglioside", Oncotarget, vol. 7, no. 27, pp. 41172-41185, (2016).

Velarde, M.C. et al., "Senescent cells and their secretory phenotype as targets for cancer therapy", Interdisciplinary Topics in Gerontology, vol. 38, pp. 17-27, (2013).

Wang, Z. et al., "CML/RAGE signal induces calcification cascade in diabetes", Diabetology & Metabolic Syndrome, vol. 8, no. 83, pp. 1-12, (2016).

Freise, A.C. et al., "In vivo imaging with antibodies and engineered fragments", Molecular Immunology, vol. 67, issue 2, pp. 142-152, (2015).

Pavlides, S. et al., "The reverse Warburg effect: Aerobic glycolysis in cancer associated fibroblasts and the tumor stroma", Cell Cycle, vol. 8, no. 23, pp. 3984-4001, (2009).

Dunn, G.P. et al., "Principles of immunology and its nuances in the central nervous system", Neuro-Oncology, vol. 17, pp. vii3-vii8, (2015).

Rettig, M.P. et al., "Evaluation of biochemical changes during in vivo erythrocyte senescence in the dog", Blood, vol. 93, no. 1, pp. 376-384, (1999).

Baraibar, M.A. et al., "Proteomic quantification and identification of carbonylated proteins upon oxidative stress and during cellular aging", Journal of Proteomics, vol. 92, pp. 63-70, (2013). Abstract Only Chaudhuri, J. et al., "A Caenorhabditis elegans model elucidates a conserved role for TRPA1-Nrf signaling in reactive α-dicarbonyl detoxification", Current Biology, vol. 26, pp. 3014-3025, (2016).

Saleh, T. et al., "Reversibility of chemotherapy-induced senescence is independent of autophagy and a potential model for tumor dormancy and cancer recurrence", bioRxiv, pp. 1-29, 5 figures, (2017).

Hubert, P. et al., "Antibody-dependent cell cytotoxicity in monoclonal antibody-mediated tumor immunotherapy", OncoImmunology, vol. 1, issue 1, pp. 103-105, (2012).

Ouchi, R. et al., "Senescence from glioma stem cell differentiation promotes tumor growth", Biochemical and Biophysical Research Communications, vol. 470, no. 2, pp. 275-281, (2016).

Evans, A. et al., "Differentiating benign from malignant solid breast masses: value of shear wave elastography according to lesion stiffness combined with grayscale ultrasound according to BI-RADS classification", British Journal of Cancer, vol. 107, pp. 224-229, (2012).

Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).

Virella, G. et al., "Development of capture assays for different modifications of human low-density lipoprotein", Clinical and Diagnostic Laboratory Immunology, vol. 12, no. 1, pp. 68-75, (2005).

Moghaddam, A.E. et al., "Reactive carbonyls are a major Th2-inducing damage-associated molecular pattern generated by oxidative stress", The Journal of Immunology, vol. 187, pp. 1626-1633, (2011).

Kuilman, T. et al., "The essence of senescence", Genes & Development, vol. 24, pp. 2463-2479, (2010).

James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).

Hein, G. et al., "Are advanced glycation end-product-modified proteins of pathogenetic importance in fibromyalgia?" Rheumatology, vol. 41, pp. 1163-1167, (2002).
Beausejour, C.M. et al., "Reversal of human cellular senescence: roles of the p53 and p16 pathways", The EMBO Journal, vol. 22, no. 16, pp. 4212-4222, (2003).
Simpson, R.J., "Aging, persistent viral infections, and immunosenescence: Can exercise "make space"?". Exercise and Sport Sciences Reviews, vol. 39, no. 1, pp. 23-33, (2011).
Gudkov, A., "Andrei Gudkov taped an expanded presentation of the slides he presented at 2017 Biology of Aging conference at Scripps, Florida, 22-27 January", Everon Biosciences, found at everonbio.com/Andrei-gudkov-taped-an-expanded-presentation-of-the-slides-he-presented-at-2017-biology-of-aging-conference-at-scripps-florida-22-27-january, 2 pages, March 21, 2017. Abstract Only
Radoi, V. et al., "Advanced glycation end products in diabetes mellitus: Mechanism of action and focused treatment", Proceedings of the Romanian Academy, Series B, vol. 1, pp. 9-19, (2012).
Sieben, C.J. et al., "Two-step senescence-focused cancer therapies", Trends in Cell Biology, pp. 1-15, (2018).
Gaens, K.H.J, et al., "Nε-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, pp. s1-s9, (2014).
Semba, R.D. et al., "Relationship of an advanced glycation end product, plasma carboxymethyl-lysine, with slow walking speed in older adults: the inCHIANTI study", European Journal of Applied Physiology, vol. 108, no. 1, pp. 191-195, (2010).
Wu, J. et al., "Sonoporation, anti-cancer drug and antibody delivery using ultrasound", Ultrasonics, vol. 44, supplement, pp. e21-e25, (2006). Abstract Only
Meerwaldt, R. et al., "Skin autofluorescence is a strong predictor of cardiac mortality in diabetes", Diabetes Care, vol. 30, no. 1, pp. 107-112, (2007).
Nagai, R. et al., "Antibody-based detection of advanced glycation end-products: promises vs. limitations", Glycoconjugate Journal, vol. 33, no. 4, pp. 545-552, (2016).
Schmidt, A.M. et al., "The biology of the receptor for advanced glycation end products and its ligands", Biochimica et Biophysica Acta, vol. 1498, pp. 99-111, (2000).
Berens, M.E. et al., ""...those left behind." Biology and oncology of invasive glioma cells", Neoplasia, vol. 1, no. 3, pp. 208-219, (1999).
Hansen, K. et al., "Microneedle enabled intradermal delivery of biologics", 3M Drug Delivery Systems, 1 page, printed on July 25, 2018.
Ikeda, K. et al., "Immunochemical approaches to AGE-structures: characterization of anti-AGE antibodies", Journal of Immunological Methods, vol. 215, no. 1-2, pp. 95-104, (1998).
De Vriese, A.S. et al., "Inhibition of the interaction of AGE-RAGE prevents hyperglycemia-induced fibrosis of the peritoneal membrane", Journal of the American Society of Nephrology, vol. 14, pp. 2109-2118, (2003).
Ott, C. et al., "Role of advanced glycation end products in cellular signaling", Redox Biology, vol. 2, pp. 411-429, (2014).
International Search Report and Written Opinion dated August 7, 2018 for PCT application number PCT/US2018/027653.
International Search Report and Written Opinion dated September 10, 2018 for PCT application number PCT/US2018/030931.

Edwards, B.M. et al., "The remarkable flexibility of the human antibody repertoire; Isolation of over one thousand different antibodies to a single protein, BLyS", The Journal of Molecular Biology, vol. 334, pp. 103-118, (2003).

Lloyd, C. et al., "Modelling the human immune response: performance of a 1011 human antibody repertoire against a broad panel of therapeutically relevant antigens", Protein Engineering, Design & Selection, vol. 22, no. 3, pp. 159-168, (2009).

Ansari, N.A. et al., "Glycated lysine residues: A marker for non-enzymatic protein glycation in age-related diseases", Disease Markers, vol. 30, pp. 317-324, (2011).

Blagosklonny, M.V. et al., "Cancer and aging", Cell Cycle, vol. 7, no. 17, pp. 2615-2618, (2008).

Chow, H-M. et al., "Senescent neurons in the alzheimer's brain kill nearby healthy neurons by blocking their WNT lifeline: The continuing saga of the zombie apocalypse", Alzheimer's & Dementia, vol. 12, no. 7(S), p. P658, (2016).

Dvorakova, E. et al., "Development of monoclonal antibodies specific for glycated prion protein", Journal of Toxicology and Environmental Health, Part A, vol. 74, pp. 1469-1475, (2011).

Search Results for "Carboxy Methyl Lysine Anitbody", 7 pages, antibodies-online.com, (2018).

Awwad, S. et al., "Overview of antibody drug delivery", Pharmaceutics, vol. 10, no. 83, pp. 1-24, (2018).

Farr, J.N. et al., "Targeting cellular senescence prevents age-related bone loss in mice", Nature Medicine, vol. 23, no. 9, pp. 1072-1079, (2017).

Hoenicke, L. et al., "Immune surveillance of senescent cells—biological significance in cancer- and non-cancer pathologies", Carcinogenesis, vol. 33, no. 6, pp. 1123-1126, (2012).

Kemmler, W. et al., "Prevalence of sarcopenia in Germany and the corresponding effect of osteoarthritis in females 70 years and older living in the community: results of the FORMoSA study", Clinical Interventions in Aging, vol. 10, pp. 1565-1573, (2015).

Myrianthopoulos, V. et al., "Senescence and senotherapeutics: a new field in cancer therapy", Pharmacology & Therapeutics, vol. 193, pp. 31-49, (2019).

Salahuddin, P. et al., "The role of advanced glycation end products in various types of neurodegenerative disease: A therapeutic approach", Cellular & Molecular Biology Letters, vol. 19, pp. 407-437, (2014).

Schosserer, M. et al., "The dual role of cellular senescence in developing tumors and their response to cancer therapy", Frontiers in Oncology, vol. 7, article 278, pp. 1-13, (2017).

Bussian, T.J. et al., "Clearance of senescent glial cells prevents tau-dependent pathology and cognitive decline", Nature Letters, vol. 562, pp. 578-582, (2018).

Penney, J. et al., "Senescence mediates neurodegeneration", Nature, vol. 562, pp. 503-504, (2018).

Trivedi, P.M. et al., "Repurposed JAK1/JAK2 inhibitor reverses established autoimmune insulitis in NOD mice", Diabetes, vol. 66, p. 1650-1660, (2017).

Wang, C. et al., "DNA damage response and cellular senescence in tissues of aging mice", Aging Cell, vol. 8, pp. 311-323, (2009).

Iizuka, K. et al., "Dasatinib improves insulin sensitivity and affects lipid metabolism in a patient with chronic myeloid leukaemia", BMJ Case Rep, pp. 1-3, (2016).

Jeon, O.H. et al., "Local clearance of senescent cells attenuates the development of post-traumatic osteoarthritis and creates a pro-regenerative environment", Nature Medicine, vol. 23, pp. 775-781, (2017). Abstract Only Duke Health News & Media, "Duke team finds missing immune cells that could fight lethal brain tumors", Duke University School of Medicine, pp. 1-5, (2018).

Apple, S., "An old idea, revived: Starve cancer to death", NYTimes.com, pp. 1-15, (2016).

Dock, J.N. et al., "Role of CD8 T cell replicative senescence in human aging and in HIV-mediated immunosenescence", Aging and Disease, vol. 2, no. 5, pp. 382-397, (2011).

Rayavarapu, S. et al., "Idiopathic inflammatory myopathies: pathogenic mechanisms of muscle weakness", Skeletal Muscle, vol. 3, no. 13, pp. 1-13, (2013).

Kudryashova, E. et al., "Satellite cell senescence underlies myopathy in a mouse model of limb-girdle muscular dystrophy 2H", The Journal of Clinical Investigation, vol. 122, no. 5, pp. 1764-1776, (2012).

Ratelade, J. et al., "Neuromyelitis optica IgG and natural killer cells produce NMO lesions in mice without myelin loss", Acta Neuropathologica, vol. 123, issue 6, pp. 861-872, (2012).

Vincent, T. et al., "Functional consequences of neuromyelitis optica-IgG astrocyte interactions on blood-brain barrier permeability and granulocyte recruitment", The Journal of Immunology, vol. 181, pp. 5730-5737, (2008).

Baarine, M. et al., "ABCD1 deletion-induced mitochondrial dysfunction is corrected by SAHA: implication for adrenoleukodystrophy", Journal of Neurochemistry, vol. 133, pp. 380-396, (2015).

Durieu, I. et al., "Subepithelial fibrosis and degradation of the bronchial extracellular matrix in cystic fibrosis", American Journal of Respiratory and Critical Care Medicine, vol. 158, no. 2, pp. 580-588, (1998).

Shapiro, B.L. et al., "Premature senescence in cultured skin fibroblasts from subjects with cystic fibrosis", Science, vol. 203, issue 4386, pp. 1251-1253, (1979). Abstract Only Fischer, B.M. et al., "Increased expression of senescence markers in cystic fibrosis airways", American Journal of Physiology Lung Cellular and Molecular Physiology, vol. 304, no. 6, pp. L394-L400, (2013).

Thom, M. et al., "An investigation of the expression of G1-phase cell cycle proteins in focal cortical dysplasia type IIB", Journal of Neuropathology and Experimental Neurology, vol. 66, no. 11, pp. 1045-1055, (2007).

Valdivieso, A.G. et al., "CFTR activity and mitochondrial function", Redox Biology, vol. 1, pp. 190-202, (2013).

Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only Ribeiro, C.M.P., "The role of intracellular calcium signals in inflammatory responses of polarized cystic fibrosis human airway epithelia", Drugs in R&D, vol. 7, issue 1, pp. 17-31, (2006). Abstract Only Velisek L. et al., "Aging: effects of aging on seizures and epilepsy", Encyclopedia of Basic Epilepsy Research, pp. 37-40, (2009). Abstract Only Muller, S. et al., "Analysis of senescence markers in rodent pancreatic stellate cells", The Pancreapedia, pp. 1-8, (2013).

Lim, M., "Acute immunology, temporal lobe epilepsy and other disorders", YoungEpilepsy.Org, pp. 1-70, found at http://youngepilepsy.org.uk/dmdocuments/MIND-THE-GAP2015_Ming%20Lim.pdf, (2015).

Definition of "Cachexia" printed from Wikipedia, the free encyclopedia on December 28, 2015 found at http://en.wikipedia.org/wiki/Cachexia.

Lok, C., "The last illness, researchers are gaining insight into the causes of Cachexia—a devastating form of muscle wasting that is often the final stage of cancer and other diseases", Nature, vol. 528, pp. 182-183, (2015).

da Rocha, O.M. et al., "Sarcopenia in rheumatoid cachexia: definition, mechanisms, clinical consequences and potential therapies", Revista Brasileira de Reumatologia, vol. 49, no. 3, pp. 294-301, (2009).
Tisdale, M.J., "Biology of Cachexia", Journal of the National Cancer Institute, vol. 89, no. 23, pp. 1763-1773, (1997).
Romanick, M. et al., "Murine models of atrophy, cachexia, and sarcopenia in skeletal muscle", Biochimica et Biophysica Acta – Molecular Basis of Disease, vol. 1832, issue 9, pp. 1410-1420, (2013).
Ali, S. et al., "Sarcopenia, cachexia and aging: Diagnosis, mechanisms and therapeutic options", Gerontology, vol. 60, no. 4, pp. 294-305, (2014).
Angelini, P.D. et al., "Constitutive HER2 signaling promotes breast cancer metastasis through cellular senescence", Cancer Research, vol. 73, no. 1, pp. 450-458, (2013).
Arai, Y. et al., "Inflammation, but not telomere length, predicts successful ageing at extreme old age: A longitudinal study of semi-supercentenarians", EBioMedicine, vol. 2, pp. 1549-1558, (2015).
Bedard, N. et al., "Inactivation of the ubiquitin-specific protease 19 deubiquitinating enzyme protects against muscle wasting", The FASEB Journal, vol. 29, no. 9, pp. 3889-3898, (2016).
Figueroa-Clarevega, A. et al., "Malignant drosophila tumors interrupt insulin signaling to induce cachexia-like wasting", Developmental Cell, vol. 33, pp. 47-55, (2015).
Giacconi, R. et al., "Cellular senescence and inflammatory burden as determinants of mortality in elderly people until the extreme old age", EBioMedicine, vol. 2, pp. 1316-1317, (2015).
Jin, H. et al., "Protein modifications as potential biomarkers in breast cancer", Biomarker Insights, vol.4, pp. 191-200, (2009).
Lee, S-J. et al., "Treating cancer cachexia to treat cancer", Skeletal Muscle, vol. 1, no. 2, pp. 1-5, (2011).
Mohamed, M.M. et al., "Human monocytes augment invasiveness and proteolytic activity of inflammatory breast cancer", Biological Chemistry, vol. 389, no. 8, pp. 1117-1121, (2008).
Pare, R. et al., "The significance of the senescence pathway in breast cancer progression", Journal of Clinical Pathology, vol. 66, pp. 491-495, (2013). Abstract Only
Pinto, N.I. et al., "Cancer as a proinflammatory environment: Metastasis and cachexia", Mediators of Inflammation, vol. 2015, pp. 1-13, (2015).
Tchkonia, T. et al., "Cellular senescence and the senescent secretory phenotype: therapeutic opportunities", The Journal of Clinical Investigation, vol. 123, no. 3, pp. 966-972, (2013).
Tesarova, P. et al., "Carbonyl and oxidative stress in patients with breast cancer – is there a relation to the stage of the disease?", Neoplasma, vol. 54, no. 3, pp. 219-224, (2007).
Tseng, Y-C., et al., "Preclinical investigation of the novel histone deacetylase inhibitor AR-42 in the treatment of cancer-induced cachexia", Journal of the National Cancer Institute, vol. 107, no. 12, pp. 1-14, (2015).
Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only
Yang, S. et al., "Impact of oxidative stress biomarkers and carboxymethyllysine (an advanced glycation end product) on prostate cancer: A prospective study", Clinical Genitourinary Cancer, vol. 13, issue 5, pp. e347-e351, (2015).
"Global Arthritis Research Network: 4th World Congress on Arthritis in Montreal", Arthritis Research & Therapy, vol. 6, supplement 3, meeting abstracts, pp. S1-S41, September 20-22, (2004).

Miller, R.E. et al., "Osteoarthritis joint pain: The cytokine connection", Cytokine, vol. 70, no. 2, pp. 185-193, (2014).
LifeExtension, "Chronic Pain", Lifeextension.com, pp. 1-18, found at www.lifeextension.com/protocols/health-concerns/chronic-pain/page-03, (2016).
Rush University Medical Center, "Scientists home in on cause of osteoarthritis pain". Science Daily, found at www.sciencedaily.com/releases/2012/12/121227173053.htm, pp. 1-4, (2012).
Kidd, B.L. et al., "Mechanisms of inflammatory pain", British Journal of Anesthesia, vol. 87, no. 1, pp. 3-11, (2001).
Price, J.S. et al., "The role of chondrocyte senescence in osteoarthritis", Aging Cell, vol. 1, pp. 57-65, (2002).
Morales, T.I., "Chondrocyte moves: clever strategies?", OsteoArthritis and Cartilage, vol. 15, pp. 861-871, (2007).
Martin, J.A. et al., "Effects of oxidative damage and telomerase activity on human articular cartilage chondrocyte senescence", Journal of Gerontology: Biological Sciences, vol. 59A, no. 4, pp. 324-337, (2004).
Ang, D.C. et al., "MCP-1 and IL-8 as pain biomarkers in fibromyalgia: A pilot study", Pain Medicine, vol. 12, pp. 1154-1161, (2011).
Burton, D.G.A. et al., "Microarray analysis of senescent vascular smooth muscle cells: A link to atherosclerosis and vascular calcification", Experimental Gerontology, vol. 44, issue 10, pp. 659-665, (2009).
Konttinen, Y.T. et al., "Chondrocyte-mediated collagenolysis correlates with cartilage destruction grades in osteoarthritis", Clinical and Experimental Rheumatology, vol. 23, pp. 19-26, (2005).
"Low back pain", U.S. Department of Health and Human Services, Public Health Service National Institutes of Health, 1-28, (2014).
Bicer, F. "CCL2 (MCP-1) mediates chronic pelvic pain through mast cells in experimental autoimmune cystitis", ETD Archive, pp. 1-120, (2012).
Loeser, R.F. "Aging and osteoarthritis: The role of chondrocyte senescence and aging changes in the cartilage matrix", Osteoarthritis and Cartilage, vol. 17, no. 8, pp. 971-979, (2009).
Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_osteoarthritic_human_articular_cartilage_and_difference_analysis, (2004). Abstract Only
Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, no. 1,2, pp. 145-152, (2002). Abstract Only
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only
De Ceuninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only
Chatterjea, D. "Mast cells and pain", Mastcell Basophil, pp. 1-5, found at www.mastcell-basophil.net/wiki/wiki-start/mast-cells-and-pain/, (2013).

Bach, B. "New drug promises relief for inflammatory pain, scientists say", News Center, Stanford Medicine PASiN, found at med.stanford.edu/news/all-news/2014/08/new-drug-promises-relief-for-inflammatory-pain--scientists-say.html, 3 pages, (2014).

Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).

"MMP13gene", NIH U.S. National Library of Medicine, found at ghr.nlm.nih.gov/gene/MMP13, 4 pages, (2016).

Hayami, T. et al., "MMP-1 (Collagenase-1) and MMP-13 (Collagenase-3) differentially regulate markers of osteoblastic differentiation in osteogenic cells", Matrix Biology, vol. 27, issue 8, pp. 682-692, (2008).

Attur, M.G. et al., "Autocrine production of IL-1 beta by human osteoarthritis-affected cartilage and differential regulation of endogenous nitric oxide, IL-6, prostaglandin E2, and IL-8", Proceedings of the Association of American Physicians, vol. 110, no. 1, pp. 65-72, (1998). Abstract Only Xu, Y-K. et al., "The role of MCP-1-CCR2 ligand-receptor axis in chondrocyte degradation and disease progress in knee osteoarthritis", Biological Research, vol. 48, no. 64, pp. 1-8, (2015).

Goldring, M.B., "The role of the chondrocyte in osteoarthritis", Arthritis & Rheumatism, vol. 43, no. 9, pp. 1916-1926, (2000).

Mobasheri, A. et al., "Chondrocyte and mesenchymal stem cell-based therapies for cartilage repair in osteoarthritis and related orthopaedic conditions", Maturitas, vol. 78, pp. 188-198, (2014).

"What are chondrocytes?", wiseGeek, found at www.wisegeek.org/what-are-chondrocytes.htm, 1 page, printed on November 29, 2016.

Woolf, A.D. et al., "Burden of major musculoskeletal conditions", Bulletin of the World Health Organization, vol. 81, no. 9, pp. 646-656, (2003).

Pereira, D. et al., "The effect of osteoarthritis definition on prevalence and incidence estimates: a systematic review", Osteoarthritis and Cartilage, vol. 19, pp. 1270-1285, (2011).

Martin, J.A. et al., "Aging, articular cartilage chondrocyte senescence and osteoarthritis", Biogerontology, vol. 3, pp. 257-264, (2002).

"What is osteoarthritis?", NIH National Institute of Arthritis and Musculoskeletal and Skin Diseases, pp. 1-4, (2014).

Definition of "Osteoarthritis" printed from Wikipedia, the free encyclopedia, found at en.wikipedia.org/wiki/Osteoarthritis, December 13, 2016

"At a glance 2016, Arthritis, Improving the quality of life for people with arthritis", National Center for Chronic Disease Prevention and Health Promotion, pp. 1-4, (2016).

"IASP Taxonomy", International Association for the Study of Pain, found at www.iasp-pain.org/Taxonomy, pp. 1-9, (2014).

"Pain: Hope through research", National Institute of Neurological Disorders and Stroke, National Institutes of Health, pp. 1-46, (2014).

Definition of "Allodynia" printed from Wikipedia, the free encyclopedia, found at en.wikipedia.org/wiki/Allodynia, December 13, 2016.

Quadros, A.U. et al., "Dynamic weight bearing is an efficient and predictable method for evaluation of arthritic nociception and its pathophysiological mechanisms in mice", Nature, Scientific Reports, pp. 1-11, (2015).

Leung, L. et al., "TNF-α and neuropathic pain – a review", Journal of Neuroinflammation, vol. 7, no. 27, pp. 1-11, (2010).

Schafers, M. et al., Tumor necrosis factor-α induces mechanical allodynia after spinal nerve ligation by activation of p38 MAPK in primary sensory neurons", The Journal of Neuroscience, vol. 23, no. 7, pp. 2517-2521, (2003).
Sun, J.L. et al., "CX3CL1/CX3CR1 regulates nerve injury-induced pain hypersensitivity through the ERK5 signaling pathway", Journal of Neuroscience Research, vol. 91, no. 4, pp. 545-553, (2013). Abstract Only
Watkins, L.R. et al., "Mechanisms of tumor necrosis factor-α (TNF-α) hyperalgesia", Brain Research, vol. 692, issues 1-2, pp. 244-250, (1995). Abstract Only
American Diabetes Association, "Diagnosis and classification of diabetes mellitus", Diabetes Care, vol. 31, supp. 1, pp. S55-S60, (2008).
"Global report on diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, no. 3, pp. 259-272, (2014).
O'Brien, P.D. et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, no. 3, pp. 278-284, (2011).
Hudkins, K.L. et al., "BTBR ob/ob mutant mice model progressive diabetic nephropathy", Journal of the American Society of Nephrology, vol. 21, pp. 1533-1542, (2010).
O'Brien, K.D. et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only
Lee, J-T. et al., "Macrophage metalloelastase (MMP12) regulates adipose tissue expansion, insulin sensitivity, and expression of inducible nitric oxide synthase", Endocrinology, vol. 155, no. 9, pp. 3409-3420, (2014).
Xu, X. et al., "A glimpse of matrix metalloproteinases in diabetic nephropathy", Current Medicinal Chemistry, vol. 21, no. 28, pp. 3244-3260, (2014).
Tsioufis, C. et al., "The role of matrix metalloproteinases in diabetes mellitus", Current Topics in Medicinal Chemistry, vol.12, no.10, pp. 1159-1165, (2012). Abstract Only
Pechhold, K. et al., "Blood glucose levels regulate pancreatic β-cell proliferation during experimentally-induced and spontaneous autoimmune diabetes in mice". PLoS One, vol. 4, no. 3, pp. e4827, (2009).
Oh, K-J. et al., "Metabolic adaptation in obesity and type II diabetes: myokines, adipokines and hepatokines", International Journal of Molecular Sciences, vol. 18, no. 1, article 8, pp. 1-31, (2017).
Micov, A. et al., "Levetiracetam synergises with common analgesics in producing antinociception in a mouse model of painful diabetic neuropathy", Pharmacological Research, vol. 97, pp. 131-142, (2015). Abstract Only
Feldman, E., "Tail flick assay", Animal Models of Diabetic Complications Consortium, pp. 1-3, (2004).
Bratwur, W., "ABT 263 was formulated in 10 ethano", found at www.selleckchem.com/blog/ABT-263-was-formulated-in-10-ethano.html, (2013). Abstract Only "Beta cell dysfunction", Diabetes and the Environment, found at www.diabetesandenvironment.org/home/mech/betacells, pp. 1-7, printed on February 27, 2019.

Edelman, D., "Understanding beta cell exhaustion in Type 2 diabetics", Diabetes Daily, found at www.diabetesdaily.com/blog/2008/06/podcast-understanding-beta-cell-exhaustion-in-type-2-diabetics, pp. 1-6, (2008).

Cao, Y. et al., "Mechanisms of endothelial to mesenchymal transition in the retina in diabetes", Investigative Ophthalmology & Visual Science, vol. 55, pp. 7321-7331, (2014).

Palmer, A.K. et al., "Cellular senescence in Type 2 diabetes: a therapeutic opportunity", Diabetes, vol. 64, pp. 2289-2298, (2015).

Cummings, B.P. et al., "Maternal ileal interposition surgery confers metabolic improvements to offspring independent of effects on maternal body weight in UCD-T2DM rats". Obesity Surgery, vol. 23, no. 12, pp. 2042-2049, (2013).

Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).

Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, no. 2, pp. 443-456, (2013).

Cummings, B.P. et al., "Vertical sleeve gastrectomy improves glucose and lipid metabolism and delays diabetes onset in the UCD-T2DM rats", Endocrinology, vol. 153, no. 8, pp. 3620-3632, (2012).

Cummings, B.P. et al., "Ileal interposition surgery improves glucose and lipid metabolism and delays diabetes onset in the UCD-T2DM rat", Gastroenterology, vol. 138, pp. 2437-2446, (2010).

American Diabetes Association, "Standards of medical care in diabetes – 2016 abridged for primary care providers", Diabetes, vol. 34, no. 1, pp. 3-21, (2016).

Definition of "Methylglyoxal" printed from Wikipedia, the free encyclopedia, found at en.wikipedia.org/wiki/Methylglyoxal, June 5, 2017.

Boesten, D.M.P.H.J. et al., "Effect of Nε-carboxymethyllysine on oxidative stress and the glutathione system in beta cells", Toxicology Reports, vol. 1, pp. 973-980, (2014).

Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).

Kender, Z. et al., "Effect of metformin on methylglyoxal metabolism in patients with type 2 diabetes", Experimental and Clinical Endocrinology & Diabetes, vol. 122, no. 5, pp. 316-319, (2014). Abstract Only Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).

Glover, A., "Of mice and men", European Biophamaceutical Review, pp. 30-34, (2016).

The basic guide to magnetic bead cell separation", Sepmag.eu, pp. 1-15, found at www.sepmag.eu/free-basic-guide-magnetic-bead-cell-separation, (2017).

Su, W-S. et al., "Controllable permeability of blood-brain barrier and reduced brain injury through low-intensity pulsed ultrasound stimulation", Oncotarget, vol. 6, no. 39, pp. 42290-42299, (2015).

Haslbeck, K.M. et al., "The RAGE pathway in inflammatory myopathies and limb girdle muscular dystrophy", Acta Neuropathologica, vol. 110, issue 3, pp. 247-254, (2005).

Sternberg, Z. et al., "AGE-RAGE in multiple sclerosis brain", Immunological Investigations, vol. 40, issue 2, pp. 197-205, (2011). Abstract Only Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).
Mulrennan, S. et al., "The role of receptor for advanced glycation end products in airway inflammation in CF and CF related diabetes", Scientific Reports, vol. 5, no. 8931, pp. 1-9, (2015).
Weber, K. et al., "Distribution of advanced glycation end products in the cerebellar neurons of dogs", Brain Research, vol. 791, pp. 11-17, (1998).
Berg, T.J. et al., "The advanced glycation end product Nε-(carboxymethyl)lysine is increased in serum from children and adolescents with type 1 diabetes", Diabetes Care, vol. 21, no. 11, pp. 1997-2002, (1998).
Degenhardt, T.P. et al., "The serum concentration of the advanced glycation end-product Nε-(carboxymethyl)lysine is increased in uremia", Kidney International, vol. 52, pp. 1064-1067, (1997).
Hayase, F. et al., "Aging of proteins: Immunological detection of a glucose-derived pyrrole formed during maillard reaction in vivo", The Journal of Biological Chemistry, vol. 263, no. 7, pp. 3758-3764, (1989).
Ikeda, K. et al., "Immunochemical approaches to AGE-structures: characterization of anti-AGE antibodies", The Maillard Reaction in Foods and Medicine, pp. 310-315, (1998).
Kume, S. et al., "Immunohistochemical and ultrastructural detection of advanced glycation end products in atherosclerotic lesions of human aorta with a novel specific monoclonal antibody", American Journal of Pathology, vol. 147, no. 3, pp. 654-667, (1995).
Makita, A. et al., "Immunochemical detection of advanced glycosylation end products in vivo", The Journal of Biological Chemistry, vol. 267, no. 8, pp. 5133-5138, (1992).
Niwa, T. et al., "Immunohistochemical detection of advanced glycation end products in dialysis-related amyloidosis", Kidney International, vol. 48, pp. 771-778, (1995).
Papanastasiou, P. et al., "Immunological quantification of advanced glycosylation end-products in the serum of patients on hemodialysis of CAPD", Kidney International, vol. 46, pp. 216-222, (1994).
Schleicher, E.D. et al., "Increased accumulation of the glycoxidation product N(epsilon)-(carboxymethyl)lysine in human tissues in diabetes and aging", The Journal of Clinical Investigation, vol. 99, no. 3, pp. 457-468, (1997).
Takeuchi, M. et al., "Immunological detection of a novel advanced glycation end-product", Molecular Medicine, vol. 7, no. 11, pp. 783-791, (2001).
Kobayashi, S. et al., "Nε-(Carboxymethyl)lysine-induced choroidal angiogenic potential facilitates retinal neovascularization in advanced-diabetic rat in vitro", The Open Pharmacology Journal vol. 2, pp. 79-85, (2008).
Tamemoto, H. et al., "AGE inhibitor-recent development", Diabetes Frontier, vol. 16, no. 5, pp. 541-546, (2005).
Nagai, R. et al., "Prevention of diabetic complication by AGE inhibitors", Progress of Medicine, vol. 207, no. 9, pp. 663-667, (2003)
Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, no. 1, pp. 283-287, (2008). Abstract Only
Chen, Z. et al., "Senescent cells re-engineered to express soluble programmed death receptor-1 for inhibiting programmed death receptor-1/programmed death ligand-1 as a vaccination approach against breast cancer", Cancer Science, vol. 109, pp. 1753-1763, (2018).

Leontieva, O.V. et al., "Yeast-like chronological senescence in mammalian cells: phenomenon, mechanism and pharmacological suppression", Aging, vol. 3, no. 11, pp. 1-14, (2011).

Moser, A.C. et al., "Immunoaffinity chromatography: an introduction to applications and recent developments", Bioanalysis, vol. 2, no. 4, pp. 769-790, (2010).

Prosser, C.G. et al., "NƐ-carboxymethyllysine in nutritional milk formulas for infants", Food Chemistry, vol. 274, pp. 886-890, (2019).

Takeuchi, M. et al., "Detection of noncarboxymethyllysine and carboxymethyllysine advanced glycation end products (AGE) in serum of diabetic patients", Molecular Medicine, vol. 5, pp. 393-405, (1999).

Teodorowicz, M. et al., "Immunomodulation by processed animal feed: The role of maillard reaction products and advanced glycation end-products (AGEs), Frontiers in Immunology, vol. 9, article 2088, pp. 1-15, (2018).

Kwak, T. et al., "Targeting of RAGE-ligand signaling impairs breast cancer cell invasion and metastasis", Oncogene, vol. 11, pp. 1559-1572, (2017). Abstract Only Inui, H. et al., "A scFv antibody-based immunoaffinity chromatography column for clean-up of bisphenol a-contaminated water samples", Journal of Agricultural and Food Chemistry, vol. 57, no. 2, pp. 353-358, (2009). Abstract Only Casset, F. et al., "A peptide mimetic of an anti-CD4 monoclonal antibody by rational design", Biochemical and Biophysical Research Communications, vol. 307, pp. 198-205, (2003).

Chikazawa, M. et al., "Multispecificity of immunoglobulin M antibodies raised against advanced glycation end products", The Journal of Biological Chemistry, vol. 288, no. 19, pp. 13204-13214, (2013).

De Pascalis, R. et al., "Grafting of "abbreviated" complementarity-determining regions containing specificity-determining residues essential for ligand contact to engineer a less immunogenic humanized monoclonal antibody", The Journal of Immunology, vol. 169, pp. 3076-3084, (2002).

Hirose, J. et al., "Immunohistochemical distribution of advanced glycation end products (AFEs) in human osteoarthritic cartilage", Acta Histochemica, vol. 113, no. 6, pp. 613-618, (2011).

Kumar, S. et al., "Molecular cloning and expression of the fabs of human autoantibodies in escherichia coli", The Journal of Biological Chemistry, vol. 275, no. 45, pp. 35129-35136, (2000).

Lamminmaki, U. et al., "Crystal structure of a recombinant anti-estradiol fab fragment in complex with 17β-estradiol", The Journal of Biological Chemistry, vol. 276, no. 39, pp. 36687-36694, (2001).

Padlan, E.A. et al., "Structure of an antibody-antigen complex: Crystal structure of the hyhel-10 fab-lysozyme complex", Proceedings of the National Academy of Science, fol. 86, pp. 5938-5942, (1989).

Schwab, W. et al., "Immunohistochemical demonstration of NƐ-(carboxymethyl)lysine protein adducts in normal and osteoarthritic cartilage", Histochemistry and Cell Biology, vol. 117, issue 6, pp. 541-546, (2002).

Smith-Gill, S.J. et al., "Contributions of immunoglobulin heavy and light chains to antibody specificity for lysozyme and two haptens" The Journal of Immunology, vol. 139, no. 12, pp. 4135-4144, (1987).

Song, M-K, et al., "Light chain of natural antibody plays a dominant role in protein antigen binding", Biochemical and Biophysical Research Communications, vol. 268, pp. 390-394, (2000).

Ward, E.S. et al., "Binding activities of a repertoire of single immunoglobulin variable domains secreted from escherichia coli". Nature, vol. 341, pp. 544-546, (1989).

Jeon O.H. et al., "Senescent cells and osteoarthritis: a painful connection", The Journal of Clinical Investigation, vol. 128, no. 4, pp. 1229-1237, (2018).

Guan, Z. et al., "Contemporary views on inflammatory pain mechanisms: TRPing over innate and microglial pathways", F1000Research, vol. 5, pp. 1-11, (2016).
Musi, N. et al., "Tau protein aggregation is associated with cellular senescence in the brain", Aging Cell, vol. 17, pp. 1-13, (2018).
International Search Report and Written Opinion dated November 25, 2019 for PCT application number PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, no. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
Linetsky, M. et al., "UVA light-excited kynurenines oxidize ascorbate and modify lens proteins through the formation of advanced glycation end products, Implications for Human Lens Aging and Cataract Formation", Journal of Biological Chemistry, vol. 289, no. 24, pp. 17111-17123, (2014).
Chaudhary, M.K. et al., "Redox imbalance in a model of rat mimicking Hutchinson-Gilford progeria syndrome", Biochemical and Biophysical Research Communications, vol. 491, no. 2, pp. 361-367, (2017). Abstract Only
Hause F. et al., "Accumulation of glycated proteins suggesting premature ageing in lamin B receptor deficient mice", Biogerontology, vol. 19, no. 1, pp. 95-100, (2017). Abstract Only
International Search Report and Written Opinion dated November 27, 2019 for PCT application number PCT/US2019/043071.
Zhang, J-M. et al., "Cytokines, Inflammation and Pain", International Anesthesiology Clinics, vol. 45, no. 2, pp. 27-37, (2007).
Bhatt A.N. et al., "Transient elevation of glycolysis confers radio-resistance by facilitating DNA repair in cells", BMC Cancer, vol. 15, Article 335, pp. 1-12, (2015).
Callier, V., "Cancer cells can't proliferate and invade at the same time", Scientific American, pp. 1-5, (2016), found at www.scientificamerican.com/article/cancer-cells-can-t-proliferate-and-invade-at-the-same-time.
Drews, G. et al., "Oxidative stress and beta-cell dysfunction", European Journal of Physiology, vol. 460, pp. 703-718, (2010).
Huang, C-C. et al., "Glycolytic inhibitor 2-deoxyglucose simultaneously targets cancer and endothelial cells to suppress neuroblastoma growth in mice", Disease Models and Mechanisms, vol. 8, pp. 1247-1254, (2015).
Kehm, R. et al., "age-related oxidative changes in pancreatic islets are predominantly located in the vascular system", Redox Biology, vol. 15, pp. 387-393, (2018).

Kohrman, A.Q. et al., "Divide or conquer: Cell cycle regulation of invasive behavior", Trends in Cell Biology, vol. 27, issue 1, pp. 12-25, (2017).
Menini, S. et al., "The advanced glycation end-product NƐ-carboxymethyllysine promotes progression of pancreatic cancer: implications for diabetes-associated risk and its prevention", Journal of Pathology, vol. 245, pp. 197-208, (2018).
Wang, J. et al., "Oxidative stress in pancreatic beta cell regeneration", Oxidative Medicine and Cellular Longevity, vol. 2017, Article id 1930261, pp. 1-9, (2017).
Nerlich, A.G. et al., "NƐ-(carboxymethyl)lysine in atherosclerotic vascular lesions as a marker for local oxidative stress", Atherosclerosis, vol. 144, issue 1, pp. 41-47, (1999). Abstract Only
Soreide, K. et al., "Epidemiological-molecular evidence of metabolic reprogramming on proliferation, autophagy and cell signaling in pancreas cancer", Cancer Letters, vol. 356, issue 2, part A, pp. 281-288, (2015) Abstract Only
Krautwald, M. et al., "Advanced glycation end products as biomarkers and gerontotoxins – a basis to explore methylglyoxal-lowering agents for Alzheimer's disease?", Experimental Gerontology, vol. 45, issue 10, pp. 744-751, (2010). Abstract Only
Leclerc, E., "Development of monoclonal antibodies to Inhibit RAGE activation in pancreatic tumors", North Dakota State University, Center for diagnostic and therapeutic strategies in pancreatic cancer, 1 page, (2019), found at www.ndsu.edu/centers/pancreaticcancer/former_investigators/leclerc_project/
Yamagishi, S-I., et al., "DNA-aptamers raised against AGEs as a blocker of various aging-related disorders", Glycoconjugate Journal, vol. 33, pp. 683-690, (2016).
Kawaguchi, M. et al., "Glyoxal inactivates glutamate transporter-1 in cultured rat astrocytes", Neuropathology, vol. 25, pp. 27-36, (2005).
Scicchitano, B.M. et al., "Counteracting muscle wasting in aging and neuromuscular diseases: the critical role of IGF-1", Aging, vol. 1, no. 5, pp. 451-457, (2009).
Southern, L. et al., "Immunohistochemical study of N-epsilon-carboxymethyl lysine (CML) in human brain: relation to vascular dementia", BMC Neuology, vol. 7, article no. 35, pp. 1-8, (2007).
Hanssen, N.M.J. et al., "Higher levels of advanced glycation endproducts in human carotid atherosclerotic plaques are associated with a rupture-prone phenotype", European Heart Journal, vol. 35, pp. 1137-1146, (2014).
Ramunas, J. et al., "Transient delivery of modified mRNA encoding TERT rapidly extends telomeres in human cells", The FASEB Journal, vol. 29, no. 5, pp. 1930-1939, (2015).
Gutierrez-Reyes, G. et al., "Cellular senescence in livers from children with end stage liver disease", Plos One, vol. 5, issue 4, pp. 1-5, (2010).
Oct. 22, 2015, U.S. Appl. No. 14/920,737.
Nov. 4, 2015, U.S. Appl. No. 14/932,200.
Sept. 29, 2017, U.S. Appl. No. 15/720,912.
Jan. 5, 2018, U.S. Appl. No. 15/863,741.
Jan. 5, 2018, U.S. Appl. No. 15/863,784.
Jan. 5, 2018, U.S. Appl. No. 15/863,811.
Jan. 5, 2018, U.S. Appl. No. 15/863,828.
Apr. 13, 2018, U.S. Appl. No. 15/953,244.
May 11, 2018, U.S. Appl. No. 15/977,587.
Dec. 20, 2018, U.S. Appl. No. 16/228,293.
Feb. 1, 2019, U.S. Appl. No. 16/265,875.
Apr. 12, 2019, U.S. Appl. No. 16/383,348.

Jun. 13 2019, U.S. Appl. No. 16/440,747.
Jan. 31, 2020, U.S. Appl. No. 16/779,369.
U.S. Appl. No. 16/311,149, filed Dec. 18, 2018, International Filing Date Jun. 23, 2016.
U.S. Appl. No. 16/092,743, International Filing Date Apr. 14, 2017.
U.S. Appl. No. 16/077,713, International Filing Date Feb. 16, 2017.
U.S. Appl. No. 16/610,473, International Filing Date May 3, 2018.--

SEQUENCE LISTING

<160> NUMBER OF SEQ ID NOS: 46

<210> SEQ ID NO 1
<211> LENGTH: 463
<212> TYPE: PRT
<213> ORGANISM: Artificial sequence
<220> FEATURE:
<223> OTHER INFORMATION: Modified Homo sapiens immunoglobulin G1 heavy
      chain

<400> SEQUENCE: 1

Met Asn Leu Leu Leu Ile Leu Thr Phe Val Ala Ala Val Ala Gln
1               5                   10                  15

Val Gln Leu Leu Gln Pro Gly Ala Glu Leu Val Lys Pro Gly Ala Ser
            20                  25                  30

Val Lys Leu Ala Cys Lys Ala Ser Gly Tyr Leu Phe Thr Thr Tyr Trp
        35                  40                  45

Met His Trp Leu Lys Gln Arg Pro Gly Gln Gly Leu Glu Trp Ile Gly
    50                  55                  60

Glu Ile Ser Pro Thr Asn Gly Arg Ala Tyr Tyr Asn Ala Arg Phe Lys
65                  70                  75                  80

Ser Glu Ala Thr Leu Thr Val Asp Lys Ser Ser Asn Thr Ala Tyr Met
                85                  90                  95

Gln Leu Ser Ser Leu Thr Ser Glu Ala Ser Ala Val Tyr Tyr Cys Ala
            100                 105                 110

Arg Ala Tyr Gly Asn Tyr Glu Phe Ala Tyr Trp Gly Gln Gly Thr Leu
        115                 120                 125

Val Thr Val Ser Val Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

```
Ser Lys Ala Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
    450                 455                 460

<210> SEQ ID NO 2
<211> LENGTH: 118
<212> TYPE: PRT
<213> ORGANISM: Mus musculus

<400> SEQUENCE: 2

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
            20                  25                  30

Trp Met His Trp Leu Lys Gln Arg Pro Gly Gln Gly Leu Glu Trp Ile
        35                  40                  45

Gly Glu Ile Ser Pro Thr Asn Gly Arg Ala Tyr Tyr Asn Ala Arg Phe
    50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
                85                  90                  95

Ala Arg Ala Tyr Gly Asn Tyr Glu Phe Ala Tyr Trp Gly Gln Gly Thr
            100                 105                 110

Leu Val Thr Val Ser Val
        115

<210> SEQ ID NO 3
<211> LENGTH: 234
<212> TYPE: PRT
<213> ORGANISM: Artificial sequence
<220> FEATURE:
<223> OTHER INFORMATION: Modified Homo sapiens immunoglobulin G1 kappa
      light chain

<400> SEQUENCE: 3

Met Asn Leu Leu Leu Ile Leu Thr Phe Val Ala Ala Ala Val Ala Asp
1               5                   10                  15

Val Val Met Thr Gln Thr Pro Leu Ser Leu Pro Val Ser Leu Gly Asp
            20                  25                  30

Gln Ala Ser Ile Ser Cys Arg Ser Arg Gln Ser Leu Val Asn Ser Asn
        35                  40                  45

Gly Asn Thr Phe Leu Gln Trp Tyr Leu Gln Lys Pro Gly Gln Ser Pro
    50                  55                  60

Lys Leu Leu Ile Tyr Lys Val Ser Leu Arg Phe Ser Gly Val Pro Asp
65                  70                  75                  80
```

-continued

```
Arg Phe Ser Gly Ser Gly Ser Gly Thr Asp Phe Thr Leu Lys Ile Ser
                85                  90                  95

Arg Val Glu Ala Glu Asp Leu Gly Leu Tyr Phe Cys Ser Gln Ser Thr
            100                 105                 110

His Val Pro Pro Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 4
<211> LENGTH: 113
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

Arg

<210> SEQ ID NO 5
<211> LENGTH: 327
<212> TYPE: PRT
<213> ORGANISM: Equus caballus

<400> SEQUENCE: 5

Ala Ser Thr Thr Ala Pro Lys Val Phe Pro Leu Ala Ser His Ser Ala
1               5                   10                  15

Ala Thr Ser Gly Ser Thr Val Ala Leu Gly Cys Leu Val Ser Ser Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ser Ser Gly Leu Tyr Ser
```

```
                        50                   55                  60
Leu Ser Ser Met Val Thr Val Pro Ala Ser Ser Leu Lys Ser Gln Thr
 65                  70                  75                  80

Tyr Ile Cys Asn Val Ala His Pro Ala Ser Ser Thr Lys Val Asp Lys
                 85                  90                  95

Lys Ile Val Ile Lys Glu Cys Asn Gly Gly Cys Pro Ala Glu Cys Leu
            100                 105                 110

Gln Val Gly Pro Ser Val Phe Ile Phe Pro Pro Lys Pro Lys Asp Val
            115                 120                 125

Leu Met Ile Ser Arg Thr Pro Thr Val Thr Cys Val Val Val Asp Val
130                 135                 140

Gly His Asp Phe Pro Asp Val Gln Phe Asn Trp Tyr Val Asp Gly Val
145                 150                 155                 160

Glu Thr His Thr Ala Thr Thr Glu Pro Lys Gln Glu Gln Phe Asn Ser
                165                 170                 175

Thr Tyr Arg Val Val Ser Val Leu Pro Ile Gln His Lys Asp Trp Leu
            180                 185                 190

Ser Gly Lys Glu Phe Lys Cys Lys Val Asn Asn Lys Ala Leu Pro Ala
        195                 200                 205

Pro Val Glu Arg Thr Ile Ser Lys Pro Thr Gly Gln Pro Arg Glu Pro
210                 215                 220

Gln Val Tyr Val Leu Ala Pro His Arg Asp Glu Leu Ser Lys Asn Lys
225                 230                 235                 240

Val Ser Val Thr Cys Leu Val Lys Asp Phe Tyr Pro Thr Asp Ile Asp
                245                 250                 255

Ile Glu Trp Lys Ser Asn Gly Gln Pro Glu Pro Glu Thr Lys Tyr Ser
            260                 265                 270

Thr Thr Pro Ala Gln Leu Asp Ser Asp Gly Ser Tyr Phe Leu Tyr Ser
            275                 280                 285

Lys Leu Thr Val Glu Thr Asn Arg Trp Gln Gln Gly Thr Thr Phe Thr
        290                 295                 300

Cys Ala Val Met His Glu Ala Leu His Asn His Tyr Thr Glu Lys Ser
305                 310                 315                 320

Val Ser Lys Ser Pro Gly Lys
                325

<210> SEQ ID NO 6
<211> LENGTH: 415
<212> TYPE: PRT
<213> ORGANISM: Equus caballus

<400> SEQUENCE: 6

Ser Leu Glu Asp Thr Ala Val Ile Pro Leu Phe Ser Glu Cys Lys Ala
  1               5                  10                  15

Pro Lys Glu Asp Asp Val Val Ser Leu Ala Cys Leu Val Lys Gly Tyr
             20                  25                  30

Phe Pro Glu Pro Val Gln Val Thr Trp Glu Pro Glu Met Gln Asn Gln
        35                   40                  45

Lys Pro Trp Thr Phe Pro Ala Met Lys Lys Gly Gln Glu Tyr Ile His
    50                  55                  60

Val Phe Ser Leu Thr Thr Trp Trp Lys Pro Gly Ser His Ser Cys Thr
 65                  70                  75                  80

Val His His Lys Ala Ser Ser Phe Arg Lys Lys Met Thr Phe Gln Glu
                 85                  90                  95
```

```
Pro Ala Ser Trp Ala Pro Gln Arg Thr Ser Ala Leu Pro Val Thr Ser
                100                 105                 110

Lys Glu Pro Thr Pro Ala Pro Thr Thr Leu Arg Lys Ser Glu Pro Ser
            115                 120                 125

Thr Arg His Thr Gln Pro Glu Thr Gln Lys Pro Arg Ile Pro Val Asp
        130                 135                 140

Thr Pro Leu Lys Glu Cys Gln Ser His Thr His Pro Pro Ser Ile Tyr
145                 150                 155                 160

Leu Leu His Pro Pro Leu Gln Gly Leu Trp Leu Lys Gly Glu Ala Thr
                165                 170                 175

Phe Thr Cys Leu Val Val Gly Asp Asp Leu Lys Asp Ala His Leu Ser
            180                 185                 190

Trp Glu Leu Ser Glu Arg Ser Asn Gly Met Phe Val Glu Ser Gly Pro
        195                 200                 205

Leu Glu Lys His Thr Asn Gly Ser Gln Ser Arg Ser Ser Arg Leu Ala
    210                 215                 220

Leu Pro Arg Ser Ser Trp Ala Met Gly Thr Ser Val Thr Cys Lys Leu
225                 230                 235                 240

Ser Tyr Pro Asn Leu Leu Ser Ser Met Glu Val Val Gly Leu Lys Glu
                245                 250                 255

His Ala Ala Ser Ala Pro Arg Ser Leu Thr Val His Ala Leu Thr Thr
            260                 265                 270

Pro Gly Leu Asn Ala Ser Pro Gly Ala Thr Ser Trp Leu Gln Cys Lys
        275                 280                 285

Val Ser Gly Phe Ser Pro Pro Glu Ile Val Leu Thr Trp Leu Glu Gly
    290                 295                 300

Gln Arg Glu Val Asp Pro Ser Trp Phe Ala Thr Ala Arg Pro Thr Ala
305                 310                 315                 320

Gln Pro Gly Asn Thr Thr Phe Gln Thr Trp Ser Ile Leu Leu Val Pro
                325                 330                 335

Thr Ile Pro Gly Pro Pro Thr Ala Thr Tyr Thr Cys Val Val Gly His
            340                 345                 350

Glu Ala Ser Arg Gln Leu Leu Asn Thr Ser Trp Ser Leu Asp Thr Gly
        355                 360                 365

Gly Leu Ala Met Thr Pro Glu Ser Lys Asp Glu Asn Ser Asp Asp Tyr
    370                 375                 380

Ala Asp Leu Asp Asp Ala Gly Ser Leu Trp Leu Thr Phe Met Ala Leu
385                 390                 395                 400

Phe Leu Ile Thr Leu Leu Tyr Ser Gly Phe Val Thr Phe Ile Lys
                405                 410                 415

<210> SEQ ID NO 7
<211> LENGTH: 334
<212> TYPE: PRT
<213> ORGANISM: Canis familiaris

<400> SEQUENCE: 7

Ser Lys Thr Ser Pro Ser Val Phe Pro Leu Ser Leu Cys His Gln Glu
1               5                   10                  15

Ser Glu Gly Tyr Val Val Ile Gly Cys Leu Val Gln Gly Phe Phe Pro
            20                  25                  30

Pro Glu Pro Val Asn Val Thr Trp Asn Ala Gly Lys Asp Ser Thr Ser
        35                  40                  45

Val Lys Asn Phe Pro Pro Met Lys Ala Ala Thr Gly Ser Leu Tyr Thr
    50                  55                  60
```

```
Met Ser Ser Gln Leu Thr Leu Pro Ala Ala Gln Cys Pro Asp Asp Ser
 65                  70                  75                  80

Ser Val Lys Cys Gln Val Gln His Ala Ser Pro Ser Lys Ala Val
                 85                  90                  95

Ser Val Pro Cys Lys Asp Asn Ser His Pro Cys His Pro Cys Pro Ser
                100                 105                 110

Cys Asn Glu Pro Arg Leu Ser Leu Gln Lys Pro Ala Leu Glu Asp Leu
            115                 120                 125

Leu Leu Gly Ser Asn Ala Ser Leu Thr Cys Thr Leu Ser Gly Leu Lys
130                 135                 140

Asp Pro Lys Gly Ala Thr Phe Thr Trp Asn Pro Ser Lys Gly Lys Glu
145                 150                 155                 160

Pro Ile Gln Lys Asn Pro Glu Arg Asp Ser Cys Gly Cys Tyr Ser Val
                165                 170                 175

Ser Ser Val Leu Pro Gly Cys Ala Asp Pro Trp Asn His Gly Asp Thr
                180                 185                 190

Phe Ser Cys Thr Ala Thr His Pro Glu Ser Lys Ser Pro Ile Thr Val
            195                 200                 205

Ser Ile Thr Lys Thr Thr Glu His Ile Pro Pro Gln Val His Leu Leu
210                 215                 220

Pro Pro Pro Ser Glu Glu Leu Ala Leu Asn Glu Leu Val Thr Leu Thr
225                 230                 235                 240

Cys Leu Val Arg Gly Phe Lys Pro Lys Asp Val Leu Val Arg Trp Leu
                245                 250                 255

Gln Gly Thr Gln Glu Leu Pro Gln Glu Lys Tyr Leu Thr Trp Glu Pro
                260                 265                 270

Leu Lys Glu Pro Asp Gln Thr Asn Met Phe Ala Val Thr Ser Met Leu
            275                 280                 285

Arg Val Thr Ala Glu Asp Trp Lys Gln Gly Glu Lys Phe Ser Cys Met
            290                 295                 300

Val Gly His Glu Ala Leu Pro Met Ser Phe Thr Gln Lys Thr Ile Asp
305                 310                 315                 320

Arg Leu Ala Gly Lys Pro Thr His Val Asn Val Ser Val Val
                325                 330

<210> SEQ ID NO 8
<211> LENGTH: 426
<212> TYPE: PRT
<213> ORGANISM: Canis familiaris

<400> SEQUENCE: 8

Thr Ser Gln Asp Leu Ser Val Phe Pro Leu Ala Ser Cys Cys Lys Asp
1               5                   10                  15

Asn Ile Ala Ser Thr Ser Val Thr Leu Gly Cys Leu Val Thr Gly Tyr
                20                  25                  30

Leu Pro Met Ser Thr Thr Val Thr Trp Asp Thr Gly Ser Leu Asn Lys
            35                  40                  45

Asn Val Thr Thr Phe Pro Thr Thr Phe His Glu Thr Tyr Gly Leu His
        50                  55                  60

Ser Ile Val Ser Gln Val Thr Ala Ser Gly Lys Trp Ala Lys Gln Arg
65                  70                  75                  80

Phe Thr Cys Ser Val Ala His Ala Glu Ser Thr Ala Ile Asn Lys Thr
                85                  90                  95

Phe Ser Ala Cys Ala Leu Asn Phe Ile Pro Pro Thr Val Lys Leu Phe
```

His Ser Ser Cys Asn Pro Val Gly Asp Thr His Thr Thr Ile Gln Leu
            100                 105                 110

Leu Cys Leu Ile Ser Gly Tyr Val Pro Gly Asp Met Glu Val Ile Trp
            115                 120                 125

Leu Val Asp Gly Gln Lys Ala Thr Asn Ile Phe Pro Tyr Thr Ala Pro
130                 135                 140

Gly Thr Lys Glu Gly Asn Val Thr Ser Thr His Ser Glu Leu Asn Ile
145                 150                 155                 160

Thr Gln Gly Glu Trp Val Ser Gln Lys Thr Tyr Thr Cys Gln Val Thr
            165                 170                 175

Tyr Gln Gly Phe Thr Phe Lys Asp Glu Ala Arg Lys Cys Ser Glu Ser
            180                 185                 190

Asp Pro Arg Gly Val Thr Ser Tyr Leu Ser Pro Ser Pro Leu Asp
            195                 200                 205

Leu Tyr Val His Lys Ala Pro Lys Ile Thr Cys Leu Val Val Asp Leu
210                 215                 220

Ala Thr Met Glu Gly Met Asn Leu Thr Trp Tyr Arg Glu Ser Lys Glu
225                 230                 235                 240

Pro Val Asn Pro Gly Pro Leu Asn Lys Lys Asp His Phe Asn Gly Thr
            245                 250                 255

Ile Thr Val Thr Ser Thr Leu Pro Val Asn Thr Asn Asp Trp Ile Glu
            260                 265                 270

Gly Glu Thr Tyr Tyr Cys Arg Val Thr His Pro His Leu Pro Lys Asp
            275                 280                 285

Ile Val Arg Ser Ile Ala Lys Ala Pro Gly Lys Arg Ala Pro Pro Asp
290                 295                 300

Val Tyr Leu Phe Leu Pro Pro Glu Glu Glu Gln Gly Thr Lys Asp Arg
305                 310                 315                 320

Val Thr Leu Thr Cys Leu Ile Gln Asn Phe Phe Pro Ala Asp Ile Ser
            325                 330                 335

Val Gln Trp Leu Arg Asn Asp Ser Pro Ile Gln Thr Asp Gln Tyr Thr
            340                 345                 350

Thr Thr Gly Pro His Lys Val Ser Gly Ser Arg Pro Ala Phe Phe Ile
            355                 360                 365

Phe Ser Arg Leu Glu Val Ser Arg Val Asp Trp Glu Gln Lys Asn Lys
            370                 375                 380

Phe Thr Cys Gln Val His Glu Ala Leu Ser Gly Ser Arg Ile Leu
385                 390                 395                 400

Gln Lys Trp Val Ser Lys Thr Pro Gly Lys
            405                 410                 415

420                 425

<210> SEQ ID NO 9
<211> LENGTH: 335
<212> TYPE: PRT
<213> ORGANISM: Felis catus

<400> SEQUENCE: 9

Ala Ser Thr Thr Ala Ser Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
            35                  40                  45

-continued

```
Gly Val His Thr Phe Pro Ser Val Leu Gln Ala Ser Gly Leu Tyr Ser
 50                  55                  60

Leu Ser Ser Met Val Thr Val Pro Ser Ser Arg Trp Leu Ser Asp Thr
 65                  70                  75                  80

Phe Thr Cys Asn Val Ala His Arg Pro Ser Ser Thr Lys Val Asp Lys
                 85                  90                  95

Thr Val Pro Lys Thr Ala Ser Thr Ile Glu Ser Lys Thr Gly Glu Gly
                100                 105                 110

Pro Lys Cys Pro Val Pro Glu Ile Pro Gly Ala Pro Ser Val Phe Ile
            115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asn Val Gln
145                 150                 155                 160

Ile Thr Trp Phe Val Asp Asn Thr Glu Met His Thr Ala Lys Thr Arg
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Ala Met Glu Arg Thr Ile Ser Lys
210                 215                 220

Ala Lys Gly Gln Pro His Glu Pro Gln Val Tyr Val Leu Pro Pro Thr
225                 230                 235                 240

Gln Glu Glu Leu Ser Glu Asn Lys Val Ser Val Thr Cys Leu Ile Lys
                245                 250                 255

Gly Phe His Pro Pro Asp Ile Ala Val Glu Trp Glu Ile Thr Gly Gln
            260                 265                 270

Pro Glu Pro Glu Asn Asn Tyr Gln Thr Thr Pro Pro Gln Leu Asp Ser
        275                 280                 285

Asp Gly Thr Tyr Phe Leu Tyr Ser Arg Leu Ser Val Asp Arg Ser His
        290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
                325                 330                 335

<210> SEQ ID NO 10
<211> LENGTH: 96
<212> TYPE: PRT
<213> ORGANISM: Camelus dromedarius

<400> SEQUENCE: 10

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Arg Glu Arg Glu Gly Val
            35                  40                  45

Ala Ala Ile Asn Ser Gly Gly Gly Ser Thr Tyr Tyr Ala Asp Ser Val
        50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95
```

<210> SEQ ID NO 11
<211> LENGTH: 96
<212> TYPE: PRT
<213> ORGANISM: Camelus dromedarius

<400> SEQUENCE: 11

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Thr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Pro Glu Asp Thr Ala Met Tyr Tyr Cys
                85                  90                  95
```

<210> SEQ ID NO 12
<211> LENGTH: 1434
<212> TYPE: DNA
<213> ORGANISM: Artificial sequence
<220> FEATURE:
<223> OTHER INFORMATION: Murine anti-AGE IgG2b heavy chain

<400> SEQUENCE: 12

| | |
|---|---|
| atggacccca agggcagcct gagctggaga atcctgctgt tcctgagcct ggccttcgag | 60 |
| ctgagctacg ccaggtgca gctgctgcag ccaggtgccg agctcgtgaa acctggcgcc | 120 |
| tctgtgaagc tggcctgcaa ggcttccggc tacctgttca ccacctactg gatgcactgg | 180 |
| ctgaagcaga ggccaggcca gggcctggaa tggatcggcg agatctcccc caccaacggc | 240 |
| agagcctact acaacgcccg gttcaagtcc gaggccaccc tgaccgtgga caagtcctcc | 300 |
| aacaccgcct acatgcagct gtcctccctg acctctgagg cctccgccgt gtactactgc | 360 |
| gccagagctt acggcaacta cgagttcgcc tactggggcc agggcaccct cgtgacagtg | 420 |
| tctgtggcta agaccacccc tcccccgtg taccctctgg ctcctggctg tggcgacacc | 480 |
| accgatcct ctgtgaccct gggctgcctc gtgaagggct acttccctga gtccgtgacc | 540 |
| gtgacctgga actccggctc cctgtcctcc tccgtgcaca cctttccagc cctgctgcag | 600 |
| tccggcctgt acaccatgtc ctccagcgtg acagtgccct cctccacctg gccttcccag | 660 |
| accgtgacat gctctgtggc ccaccctgcc tcttccacca ccgtggacaa gaagctggaa | 720 |
| ccctccggcc ccatctccac catcaaccct gccctccct gcaaagaatg ccacaagtgc | 780 |
| cctgccccca acctggaagg cggcccttcc gtgttcatct cccacccaa catcaaggac | 840 |
| gtgctgatga tctccctgac ccccaaagtg acctgcgtgg tggtgacgt tccgaggac | 900 |
| gaccctgacg tgcagatcag ttggttcgtg aacaacgtgg aagtgcacac cgcccagacc | 960 |
| cagacacaca gagaggacta caacagcacc atcagagtgg tgtctaccct gcccatccag | 1020 |
| caccaggact ggatgtccgg caaagaattc aagtgcaaag tgaacaacaa ggacctgccc | 1080 |
| agccccatcg agcggaccat ctccaagatc aagggcctcg tgcgggctcc ccaggtgtac | 1140 |
| attctgcctc caccagccga gcagctgtcc cggaaggatg tgtctctgac atgtctggtc | 1200 |
| gtgggcttca accccggcga catctccgtg gaatggacct ccaacggcca caccgaggaa | 1260 |

| | |
|---|---|
| aactacaagg acaccgcccc tgtgctggac tccgacggct cctacttcat ctactccaag | 1320 |
| ctgaacatga agacctccaa gtgggaaaag accgactcct tctcctgcaa cgtgcggcac | 1380 |
| gagggcctga agaactacta cctgaagaaa accatctccc ggtccccgg ctag | 1434 |

<210> SEQ ID NO 13
<211> LENGTH: 1416
<212> TYPE: DNA
<213> ORGANISM: Artificial sequence
<220> FEATURE:
<223> OTHER INFORMATION: Chimeric anti-AGE human IgG1 antibody heavy
      chain

<400> SEQUENCE: 13

| | |
|---|---|
| atggacccca agggcagcct gagctggaga atcctgctgt tcctgagcct ggccttcgag | 60 |
| ctgagctacg ccaggtgca gctgctgcag ccaggtgccg agctcgtgaa acctggcgcc | 120 |
| tctgtgaagc tggcctgcaa ggcttccggc tacctgttca ccacctactg gatgcactgg | 180 |
| ctgaagcaga ggccaggcca gggcctggaa tggatcggcg agatctcccc caccaacggc | 240 |
| agagcctact acaacgcccg gttcaagtcc gaggccaccc tgaccgtgga caagtcctcc | 300 |
| aacaccgcct acatgcagct gtcctccctg acctctgagg cctccgccgt gtactactgc | 360 |
| gccagagctt acggcaacta cgagttcgcc tactggggcc agggcacccct cgtgacagtg | 420 |
| tctgtggcta gcaccaaggg ccccagcgtg ttccctctgg cccccagcag caagagcacc | 480 |
| agcggcggaa ccgccgccct gggctgcctg gtgaaggact acttccccga gcccgtgacc | 540 |
| gtgtcctgga cagcggcgc tctgaccagc ggagtgcaca ccttccctgc cgtgctgcag | 600 |
| agcagcggcc tgtactccct gagcagcgtg gtgaccgtgc cagcagcag cctgggcacc | 660 |
| cagacctaca tctgcaacgt gaaccacaag ccctccaaca ccaaggtgga caagaaggtg | 720 |
| gagcctaaga gctgcgacaa gacccacacc tgccctccct gccccgcccc cgagctgctg | 780 |
| ggcggaccca gcgtgttcct gttccctccc aagcccaagg acaccctgat gatcagccgc | 840 |
| acccccgagg tgacctgcgt ggtggtggac gtgagccacg aggaccccga ggtgaagttc | 900 |
| aactggtacg tggacggcgt ggaggtgcac aacgccaaga ccaagcctcg ggaggagcag | 960 |
| tacaactcca cctaccgcgt ggtgagcgtg ctgaccgtgc tgcaccagga ctggctgaac | 1020 |
| ggcaaggagt acaagtgcaa ggtgagcaac aaggccctgc cgctcccat cgagaagacc | 1080 |
| atcagcaagg ccaagggcca gccccgggag cctcaggtgt acaccctgcc ccccagccgc | 1140 |
| gacgagctga ccaagaacca ggtgagcctg acctgcctgg tgaagggctt ctaccctcc | 1200 |
| gacatcgccg tggagtggga gagcaacggc cagcctgaga caactacaa gaccacccct | 1260 |
| cccgtgctgg acagcgacgg cagcttcttc ctgtacagca agctgaccgt ggacaagtcc | 1320 |
| cggtggcagc agggcaacgt gttcagctgc agcgtgatgc acgaggccct gcacaaccac | 1380 |
| tacacccaga gagcctgag cctgagcccc ggatag | 1416 |

<210> SEQ ID NO 14
<211> LENGTH: 720
<212> TYPE: DNA
<213> ORGANISM: Artificial sequence
<220> FEATURE:
<223> OTHER INFORMATION: Murine anti-AGE Kappa light chain

<400> SEQUENCE: 14

| | |
|---|---|
| atggagaccg acaccctgct gctctgggtg ctgctgctct gggtgcccgg ctccaccgga | 60 |
| gacgtcgtga tgacccagac ccctctgtcc ctgcctgtgt ctctgggcga ccaggcctcc | 120 |

```
atctcctgcc ggtctagaca gtccctcgtg aactccaacg gcaacacctt cctgcagtgg    180
tatctgcaga agcccggcca gtcccccaag ctgctgatct acaaggtgtc cctgcggttc    240
tccggcgtgc ccgacagatt ttccggctct ggctctggca ccgacttcac cctgaagatc    300 tcccggggtgg aagccgagga cctgggcctg tacttctgca gccagtccac ccacgtgccc    360
cctacatttg gcggaggcac caagctggaa atcaaacggg cagatgctgc accaactgta    420
tccatcttcc caccatccag tgagcagtta acatctggag gtgcctcagt cgtgtgcttc    480
ttgaacaact tctaccccaa agacatcaat gtcaagtgga agattgatgg cagtgaacga    540
caaaatggcg tcctgaacag ttggactgat caggacagca agacagcac ctacagcatg    600 agcagcaccc tcacgttgac caaggacgag tatgaacgac ataacagcta tacctgtgag    660
gccactcaca gacatcaac ttcacccatt gtcaagagct caacaggaa tgagtgttga    720

<210> SEQ ID NO 15
<211> LENGTH: 720
<212> TYPE: DNA
<213> ORGANISM: Artificial sequence
<220> FEATURE:
<223> OTHER INFORMATION: Chimeric anti-AGE human kappa light chain

<400> SEQUENCE: 15
atggagaccg acaccctgct gctctgggtg ctgctgctct gggtgcccgg ctccaccgga     60
gacgtcgtga tgacccagac ccctctgtcc ctgcctgtgt ctctgggcga ccaggcctcc    120
atctcctgcc ggtctagaca gtccctcgtg aactccaacg gcaacacctt cctgcagtgg    180
tatctgcaga agcccggcca gtcccccaag ctgctgatct acaaggtgtc cctgcggttc    240
tccggcgtgc ccgacagatt ttccggctct ggctctggca ccgacttcac cctgaagatc    300 tcccggggtgg aagccgagga cctgggcctg tacttctgca gccagtccac ccacgtgccc    360
cctacatttg gcggaggcac caagctggaa atcaagcgga ccgtggccgc ccccagcgtg    420
ttcatcttcc ctcccagcga cgagcagctg aagtctggaa ccgccagcgt ggtgtgcctg    480
ctgaacaact tctaccccg cgaggccaag gtgcagtgga aggtggacaa cgccctgcag    540
agcggcaaca gccaggagag cgtgaccgag caggactcca aggacagcac ctacagcctg    600
agcagcaccc tgaccctgag caaggccgac tacgagaagc acaaggtgta cgcctgcgag    660
gtgacccacc agggactgtc tagccccgtg accaagagct caaccgggg cgagtgctaa    720

<210> SEQ ID NO 16
<211> LENGTH: 477
<212> TYPE: PRT
<213> ORGANISM: Artificial sequence
<220> FEATURE:
<223> OTHER INFORMATION: Murine anti-AGE IgG2b heavy chain

<400> SEQUENCE: 16

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Leu Gln Pro Gly
                20                  25                  30

Ala Glu Leu Val Lys Pro Gly Ala Ser Val Lys Leu Ala Cys Lys Ala
        35                  40                  45

Ser Gly Tyr Leu Phe Thr Thr Tyr Trp Met His Trp Leu Lys Gln Arg
    50                  55                  60

Pro Gly Gln Gly Leu Glu Trp Ile Gly Glu Ile Ser Pro Thr Asn Gly
65                  70                  75                  80
```

```
Arg Ala Tyr Tyr Asn Ala Arg Phe Lys Ser Glu Ala Thr Leu Thr Val
                 85                  90                  95

Asp Lys Ser Ser Asn Thr Ala Tyr Met Gln Leu Ser Ser Leu Thr Ser
            100                 105                 110

Glu Ala Ser Ala Val Tyr Tyr Cys Ala Arg Ala Tyr Gly Asn Tyr Glu
        115                 120                 125

Phe Ala Tyr Trp Gly Gln Gly Thr Leu Val Thr Val Ser Val Ala Lys
    130                 135                 140

Thr Thr Pro Pro Ser Val Tyr Pro Leu Ala Pro Gly Cys Gly Asp Thr
145                 150                 155                 160

Thr Gly Ser Ser Val Thr Leu Gly Cys Leu Val Lys Gly Tyr Phe Pro
                165                 170                 175

Glu Ser Val Thr Val Thr Trp Asn Ser Gly Ser Leu Ser Ser Ser Val
            180                 185                 190

His Thr Phe Pro Ala Leu Leu Gln Ser Gly Leu Tyr Thr Met Ser Ser
        195                 200                 205

Ser Val Thr Val Pro Ser Ser Thr Trp Pro Ser Gln Thr Val Thr Cys
    210                 215                 220

Ser Val Ala His Pro Ala Ser Ser Thr Val Asp Lys Lys Leu Glu
225                 230                 235                 240

Pro Ser Gly Pro Ile Ser Thr Ile Asn Pro Cys Pro Cys Lys Glu
                245                 250                 255

Cys His Lys Cys Pro Ala Pro Asn Leu Glu Gly Gly Pro Ser Val Phe
            260                 265                 270

Ile Phe Pro Pro Asn Ile Lys Asp Val Leu Met Ile Ser Leu Thr Pro
        275                 280                 285

Lys Val Thr Cys Val Val Val Asp Val Ser Glu Asp Pro Asp Val
290                 295                 300

Gln Ile Ser Trp Phe Val Asn Asn Val Glu Val His Thr Ala Gln Thr
305                 310                 315                 320

Gln Thr His Arg Glu Asp Tyr Asn Ser Thr Ile Arg Val Val Ser Thr
                325                 330                 335

Leu Pro Ile Gln His Gln Asp Trp Met Ser Gly Lys Glu Phe Lys Cys
            340                 345                 350

Lys Val Asn Asn Lys Asp Leu Pro Ser Pro Ile Glu Arg Thr Ile Ser
        355                 360                 365

Lys Ile Lys Gly Leu Val Arg Ala Pro Gln Val Tyr Ile Leu Pro Pro
    370                 375                 380

Pro Ala Glu Gln Leu Ser Arg Lys Asp Val Ser Leu Thr Cys Leu Val
385                 390                 395                 400

Val Gly Phe Asn Pro Gly Asp Ile Ser Val Glu Trp Thr Ser Asn Gly
                405                 410                 415

His Thr Glu Glu Asn Tyr Lys Asp Thr Ala Pro Val Leu Asp Ser Asp
            420                 425                 430

Gly Ser Tyr Phe Ile Tyr Ser Lys Leu Asn Met Lys Thr Ser Lys Trp
        435                 440                 445

Glu Lys Thr Asp Ser Phe Ser Cys Asn Val Arg His Glu Gly Leu Lys
    450                 455                 460

Asn Tyr Tyr Leu Lys Lys Thr Ile Ser Arg Ser Pro Gly
465                 470                 475

<210> SEQ ID NO 17
<211> LENGTH: 471
<212> TYPE: PRT
```

<213> ORGANISM: Artificial sequence
<220> FEATURE:
<223> OTHER INFORMATION: Chimeric anti-AGE human IgG1 heavy chain

<400> SEQUENCE: 17

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Leu Gln Pro Gly
            20                  25                  30

Ala Glu Leu Val Lys Pro Gly Ala Ser Val Lys Leu Ala Cys Lys Ala
        35                  40                  45

Ser Gly Tyr Leu Phe Thr Thr Tyr Trp Met His Trp Leu Lys Gln Arg
50                  55                  60

Pro Gly Gln Gly Leu Glu Trp Ile Gly Glu Ile Ser Pro Thr Asn Gly
65                  70                  75                  80

Arg Ala Tyr Tyr Asn Ala Arg Phe Lys Ser Glu Ala Thr Leu Thr Val
                85                  90                  95

Asp Lys Ser Ser Asn Thr Ala Tyr Met Gln Leu Ser Ser Leu Thr Ser
            100                 105                 110

Glu Ala Ser Ala Val Tyr Tyr Cys Ala Arg Ala Tyr Gly Asn Tyr Glu
        115                 120                 125

Phe Ala Tyr Trp Gly Gln Gly Thr Leu Val Thr Val Ser Val Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
```

```
                385                 390                 395                 400
Asp Ile Ala Val Glu Trp Glu Ser Asn Gly Gln Pro Glu Asn Asn Tyr
                    405                 410                 415
Lys Thr Thr Pro Pro Val Leu Asp Ser Asp Gly Ser Phe Phe Leu Tyr
                    420                 425                 430
Ser Lys Leu Thr Val Asp Lys Ser Arg Trp Gln Gln Gly Asn Val Phe
                    435                 440                 445
Ser Cys Ser Val Met His Glu Ala Leu His Asn His Tyr Thr Gln Lys
                    450                 455                 460
Ser Leu Ser Leu Ser Pro Gly
465                 470

<210> SEQ ID NO 18
<211> LENGTH: 239
<212> TYPE: PRT
<213> ORGANISM: Artificial sequence
<220> FEATURE:
<223> OTHER INFORMATION: Murine anti-AGE kappa light chain

<400> SEQUENCE: 18

Met Glu Thr Asp Thr Leu Leu Leu Trp Val Leu Leu Leu Trp Val Pro
1               5                   10                  15
Gly Ser Thr Gly Asp Val Val Met Thr Gln Thr Pro Leu Ser Leu Pro
                20                  25                  30
Val Ser Leu Gly Asp Gln Ala Ser Ile Ser Cys Arg Ser Arg Gln Ser
            35                  40                  45
Leu Val Asn Ser Asn Gly Asn Thr Phe Leu Gln Trp Tyr Leu Gln Lys
        50                  55                  60
Pro Gly Gln Ser Pro Lys Leu Leu Ile Tyr Lys Val Ser Leu Arg Phe
65                  70                  75                  80
Ser Gly Val Pro Asp Arg Phe Ser Gly Ser Gly Ser Gly Thr Asp Phe
                85                  90                  95
Thr Leu Lys Ile Ser Arg Val Glu Ala Glu Asp Leu Gly Leu Tyr Phe
                100                 105                 110
Cys Ser Gln Ser Thr His Val Pro Pro Thr Phe Gly Gly Gly Thr Lys
            115                 120                 125
Leu Glu Ile Lys Arg Ala Asp Ala Ala Pro Thr Val Ser Ile Phe Pro
        130                 135                 140
Pro Ser Ser Glu Gln Leu Thr Ser Gly Gly Ala Ser Val Val Cys Phe
145                 150                 155                 160
Leu Asn Asn Phe Tyr Pro Lys Asp Ile Asn Val Lys Trp Lys Ile Asp
                165                 170                 175
Gly Ser Glu Arg Gln Asn Gly Val Leu Asn Ser Trp Thr Asp Gln Asp
                180                 185                 190
Ser Lys Asp Ser Thr Tyr Ser Met Ser Ser Thr Leu Thr Leu Thr Lys
            195                 200                 205
Asp Glu Tyr Glu Arg His Asn Ser Tyr Thr Cys Glu Ala Thr His Lys
        210                 215                 220
Thr Ser Thr Ser Pro Ile Val Lys Ser Phe Asn Arg Asn Glu Cys
225                 230                 235

<210> SEQ ID NO 19
<211> LENGTH: 239
<212> TYPE: PRT
<213> ORGANISM: Artificial sequence
<220> FEATURE:
<223> OTHER INFORMATION: Chimeric anti-AGE human kappa light chain
```

<400> SEQUENCE: 19

Met Glu Thr Asp Thr Leu Leu Leu Trp Val Leu Leu Leu Trp Val Pro
1               5                   10                  15

Gly Ser Thr Gly Asp Val Val Met Thr Gln Thr Pro Leu Ser Leu Pro
            20                  25                  30

Val Ser Leu Gly Asp Gln Ala Ser Ile Ser Cys Arg Ser Arg Gln Ser
        35                  40                  45

Leu Val Asn Ser Asn Gly Asn Thr Phe Leu Gln Trp Tyr Leu Gln Lys
    50                  55                  60

Pro Gly Gln Ser Pro Lys Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Leu Tyr Phe
            100                 105                 110

Cys Ser Gln Ser Thr His Val Pro Pro Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 20
<211> LENGTH: 118
<212> TYPE: PRT
<213> ORGANISM: Artificial sequence
<220> FEATURE:
<223> OTHER INFORMATION: Murine anti-AGE IgG2b heavy chain (variable
      region)

<400> SEQUENCE: 20

Gln Val Gln Leu Leu Gln Pro Gly Ala Glu Leu Val Lys Pro Gly Ala
1               5                   10                  15

Ser Val Lys Leu Ala Cys Lys Ala Ser Gly Tyr Leu Phe Thr Thr Tyr
            20                  25                  30

Trp Met His Trp Leu Lys Gln Arg Pro Gly Gln Gly Leu Glu Trp Ile
        35                  40                  45

Gly Glu Ile Ser Pro Thr Asn Gly Arg Ala Tyr Tyr Asn Ala Arg Phe
    50                  55                  60

Lys Ser Glu Ala Thr Leu Thr Val Asp Lys Ser Ser Asn Thr Ala Tyr
65                  70                  75                  80

Met Gln Leu Ser Ser Leu Thr Ser Glu Ala Ser Ala Val Tyr Tyr Cys
                85                  90                  95

Ala Arg Ala Tyr Gly Asn Tyr Glu Phe Ala Tyr Trp Gly Gln Gly Thr
            100                 105                 110

Leu Val Thr Val Ser Val
        115

<210> SEQ ID NO 21
<211> LENGTH: 112
<212> TYPE: PRT
<213> ORGANISM: Artificial sequence
<220> FEATURE:
<223> OTHER INFORMATION: Murine anti-AGE kappa light chain (variable
      region)

<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val Asn Ser
            20                  25                  30

Asn Gly Asn Thr Phe Leu Gln Trp Tyr Leu Gln Lys Pro Gly Gln Ser
        35                  40                  45

Pro Lys Leu Leu Ile Tyr Lys Val Ser Leu Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 22
<211> LENGTH: 326
<212> TYPE: PRT
<213> ORGANISM: Artificial sequence
<220> FEATURE:
<223> OTHER INFORMATION: Human constant region

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

```
Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 7
<212> TYPE: PRT
<213> ORGANISM: Artificial sequence
<220> FEATURE:
<223> OTHER INFORMATION: CDR1H (heavy chain)

<400> SEQUENCE: 23

Ser Tyr Thr Met Gly Val Ser
1               5

<210> SEQ ID NO 24
<211> LENGTH: 17
<212> TYPE: PRT
<213> ORGANISM: Artificial sequence
<220> FEATURE:
<223> OTHER INFORMATION: CDR2H (heavy chain)

<400> SEQUENCE: 24

Thr Ile Ser Ser Gly Gly Ser Thr Tyr Tyr Pro Asp Ser Val Lys
1               5                   10                  15

Gly

<210> SEQ ID NO 25
<211> LENGTH: 10
<212> TYPE: PRT
<213> ORGANISM: Artificial sequence
<220> FEATURE:
<223> OTHER INFORMATION: CDR3H (heavy chain)
<220> FEATURE:
<221> NAME/KEY: misc_feature
<222> LOCATION: (10)..(10)
<223> OTHER INFORMATION: Xaa can be any naturally occurring amino acid

<400> SEQUENCE: 25

Gln Gly Gly Trp Leu Pro Pro Phe Ala Xaa
1               5                   10

<210> SEQ ID NO 26
<211> LENGTH: 17
<212> TYPE: PRT
```

```
<213> ORGANISM: Artificial sequence
<220> FEATURE:
<223> OTHER INFORMATION: CDR1L (light chain)

<400> SEQUENCE: 26

Arg Ala Ser Lys Ser Val Ser Thr Ser Ser Arg Gly Tyr Ser Tyr Met
1               5                   10                  15

His

<210> SEQ ID NO 27
<211> LENGTH: 7
<212> TYPE: PRT
<213> ORGANISM: Artificial sequence
<220> FEATURE:
<223> OTHER INFORMATION: CDR2L (light chain)

<400> SEQUENCE: 27

Leu Val Ser Asn Leu Glu Ser
1               5

<210> SEQ ID NO 28
<211> LENGTH: 9
<212> TYPE: PRT
<213> ORGANISM: Artificial sequence
<220> FEATURE:
<223> OTHER INFORMATION: CDR3L (light chain)

<400> SEQUENCE: 28

Gln His Ile Arg Glu Leu Thr Arg Ser
1               5

<210> SEQ ID NO 29
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 29

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Leu Phe Thr Thr Tyr Trp Met His Trp Val Arg Gln Ala
        50                  55                  60

Pro Gly Gln Gly Leu Glu Trp Met Gly Glu Ile Ser Pro Thr Asn Gly
65                  70                  75                  80

Arg Ala Tyr Tyr Asn Gln Lys Phe Gln Gly Arg Val Thr Met Thr Val
                85                  90                  95

Asp Lys Ser Thr Asn Thr Val Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 30
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 30
atggacccca agggcagcct gagctggaga atcctgctgt tcctgagcct ggccttcgag    60
ctgagctacg ccaggtgca gctggtgcag tctggcgccg aagtgaagaa acctggcgcc    120
tccgtgaggt gtcctgcaag gcttccggct acctgttcac cacctactgg atgcactggg    180
tgcgacaggc ccctggacag ggcctggaat ggatgggcga gatctcccct accaacggca    240
gagcctacta caacagaaat tccagggcag agtgaccatg accgtggaca agtccaccaa    300
caccgtgtac atggaactgt cctccctgcg gagcgaggac accgccgtgt actactgcgc    360
```

```
tagagcctac ggcaactacg attcgcctac tggggccagg gcaccctcgt gacagtgtcc      420
tctgctagca ccaagggccc cagcgtgttc cctctggccc ccagcagcaa gagcaccagc      480
ggcggaaccg ccgccctggg ctgcctggga aggactactt ccccgagccc gtgaccgtgt      540
cctggaacag cggcgctctg accagcggag tgcacacctt ccctgccgtg ctgcagagca      600
gcggcctgta ctccctgagc agcgtggtga ccgtgccagc agcagcctgg cacccagac       660 ctacatctgc aacgtgaacc acaagccctc aacaccaag gtggacaaga aggtggagcc       720
taagagctgc gacaagaccc acacctgccc tccctgcccc gccccgagct gctgggcgga      780
cccagcgtgt tcctgttccc tcccaagccc aaggacaccc tgatgatcag ccgcaccccc      840
gaggtgacct gcgtggtggt ggacgtgagc cacgaggacc ccgaggtgag ttcaactggt      900
acgtggacgg cgtggaggtg cacaacgcca agaccaagcc tcgggaggag cagtacaact      960
ccacctaccg cgtggtgagc gtgctgaccg tgctgcacca ggactggctg aacggcagga     1020
gtacaagtgc aaggtgagca acaaggccct gcccgctccc atcgagaaga ccatcagcaa     1080
ggccaagggc cagccccggg agcctcaggt gtacaccctg cccccagcc gcgacgagct      1140 gacaagaacc aggtgagcct gacctgcctg gtgaagggct tctacccctc cgacatcgcc     1200
gtggagtggg agagcaacgg ccagcctgag aacaactaca agaccacccc tcccgtgctg     1260
gacagcgacg gcagcttcttc ctgtacagca agctgaccgt ggacaagtcc cggtggcagc     1320
agggcaacgt gttcagctgc agcgtgatgc acgaggccct gcacaaccac tacacccaga     1380
agagcctgag cctgagcccg gatagtaa                                        1408
```

<210> SEQ ID NO 31
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 31

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Leu Phe Thr Thr Tyr Trp Met His Trp Val Arg Gln Ala
        50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Thr Asn Thr Ala Tyr Met Glu Leu Ser Ser Leu Arg Ser
            100                 105                 110

Glu Asp Thr Ala Val Tyr Tyr Cys Ala Arg Ala Tyr Gly Asn Tyr Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 32
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 32
atggacccca agggcagcct gagctggaga atcctgctgt tcctgagcct ggccttcgag     60
ctgagctacg ccaggtgca gctggtgcag tctggcgccg aagtgaagaa acctggcgcc    120
tccgtgaggt gtcctgcaag gcttccggct acctgttcac cacctactgg atgcactggg    180
tgcgacaggc ccctggacag ggcctggaat ggatgggcga gatctcccct accaacggca    240
gagcctacta caaccaaaat tccagggcag agtgaccatg accgtggaca agtccaccaa    300
caccgcttac atggaactgt cctccctgcg gagcgaggac accgccgtgt actactgcgc    360

-continued

```
tagagcctac ggcaactacg attcgcctac tggggccagg gcaccctcgt gacagtgtcc    420
tctgctagca ccaagggccc cagcgtgttc cctctggccc ccagcagcaa gagcaccagc    480
ggcggaaccg ccgccctggg ctgcctggga aggactactt ccccgagccc gtgaccgtgt    540 cctgaacag cggcgctctg accagcggag tgcacacctt ccctgccgtg ctgcagagca    600
gcggcctgta ctccctgagc agcgtggtga ccgtgccagc agcagcctgg cacccagac    660 ctacatctgc aacgtgaacc acaagccctc aacaccaag gtggacaaga aggtggagcc    720
taagagctgc gacaagaccc acacctgccc tccctgcccc gccccgagct gctgggcgga    780
cccagcgtgt tcctgttccc tcccaagccc aaggacaccc tgatgatcag ccgcacccc    840 gaggtgacct gcgtggtggt ggacgtgagc cacgaggacc ccgaggtgag ttcaactggt    900
acgtggacgg cgtggaggtg cacaacgcca agaccaagcc tcgggaggag cagtacaact    960
ccacctaccg cgtggtgagc gtgctgaccg tgctgcacca ggactggctg aacggcagga   1020
gtacaagtgc aaggtgagca acaaggccct gcccgctccc atcgagaaga ccatcagcaa   1080 ggccaaggc cagccccggg agcctcaggt gtacaccctg cccccagcc gcgacgagct   1140 gacaagaacc aggtgagcct gacctgcctg gtgaagggct cctaccctc cgacatcgcc   1200 gtggagtggg agagcaacgg ccagcctgag aacaactaca agaccacccc tcccgtgctg   1260
gacagcgacg gcagcttcttc ctgtacagca agctgaccgt ggacaagtcc cggtggcagc   1320
agggcaacgt gttcagctgc agcgtgatgc acgaggccct gcacaaccac tacacccaga   1380
agagcctgag cctgagcccg gatagtaa                                      1408
```

<210> SEQ ID NO 33
<211> LENGTH: 468
<212> TYPE: PRT
<213> ORGANISM: Artificial Sequence
<220> FEATURE:
<223> OTHER INFORMATION: Humanized heavy chain

<400> SEQUENCE: 33

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Tyr Leu Phe Thr Thr Tyr Trp Met His Trp Val Arg Gln Ala
        50                  55                  60

Pro Gly Gln Gly Leu Glu Trp Met Gly Glu Ile Ser Pro Thr Asn Gly
65                  70                  75                  80

Arg Ala Tyr Tyr Asn Ala Lys Phe Gln Gly Arg Val Thr Met Thr Val
                85                  90                  95

Asp Lys Ser Ile Asn Thr Ala Tyr Met Glu Leu Ser Arg Leu Arg Ser
                100                 105                 110

Asp Asp Thr Ala Val Tyr Tyr Cys Ala Arg Ala Tyr Gly Asn Tyr Phe
            115                 120                 125

Ala Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 34
<211> LENGTH: 1408
<212> TYPE: DNA
<213> ORGANISM: Artificial Sequence
<220> FEATURE:
<223> OTHER INFORMATION: Humanized heavy chain

<400> SEQUENCE: 34
atggacccca agggcagcct gagctggaga atcctgctgt tcctgagcct ggccttcgag    60
ctgagctacg ccaggtgca gctggtgcag tctggcgccg aagtgaagaa acctggcgcc    120
tccgtgaggt gtcctgcaag gcttccggct acctgttcac cacctactgg atgcactggg   180
tgcgacaggc ccctggacag ggcctggaat ggatgggcga gatctcccct accaacggca   240
gagcctacta caaccaaaat tccagggcag agtgaccatg accgtggaca gtccatcaa   300 caccgcttac atggaactgt ccagactgcg gagcgatgac accgccgtgt actactgcgc   360

```
tagagcctac ggcaactacg attcgcctac tggggccagg gcaccctcgt gacagtgtcc    420
tctgctagca ccaagggccc cagcgtgttc cctctggccc ccagcagcaa gagcaccagc    480
ggcggaaccg ccgccctggg ctgcctggga aggactactt ccccgagccc gtgaccgtgt    540
cctggaacag cggcgctctg accagcggag tgcacacctt ccctgccgtg ctgcagagca    600
gcggcctgta ctccctgagc agcgtggtga ccgtgccagc agcagcctgg cacccagac     660 ctacatctgc aacgtgaacc acaagccctc aacaccaag gtggacaaga aggtggagcc    720
taagagctgc gacaagaccc acacctgccc tccctgcccc gccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgag ttcaactggt    900
acgtggacgg cgtggaggtg cacaacgcca agaccaagcc tcgggaggag cagtacaact    960
ccacctaccg cgtggtgagc gtgctgaccg tgctgcacca ggactggctg aacggcagga   1020
gtacaagtgc aaggtgagca acaaggccct gcccgctccc atcgagaaga ccatcagcaa   1080
ggccaagggc cagccccggg agcctcaggt gtacaccctg cccccagcc cgacgagct    1140 gacaagaacc aggtgagcct gacctgcctg gtgaagggct tctacccctc cgacatcgcc   1200
gtggagtggg agagcaacgg ccagcctgag aacaactaca agaccacccc tcccgtgctg   1260
gacagcgacg gcagcttcttc ctgtacagca agctgaccgt ggacaagtcc cggtggcagc   1320
agggcaacgt gttcagctgc agcgtgatgc acgaggccct gcacaaccac tacacccaga   1380
agagcctgag cctgagcccg gatagtaa                                      1408
```

```
<210> SEQ ID NO 35
<211> LENGTH: 238
<212> TYPE: PRT
<213> ORGANISM: Artificial Sequence
<220> FEATURE:
<223> OTHER INFORMATION: Humanized light chain

<400> SEQUENCE: 35

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Val Asn Ser Asn Gly Asn Thr Phe Leu Gln Trp Tyr Gln Gln Arg
        50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Ser Gln Ser Thr His Val Pro Pro Thr Phe Gly Gly Gly Thr Val
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175
```

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 36
<211> LENGTH: 715
<212> TYPE: DNA
<213> ORGANISM: Artificial Sequence
<220> FEATURE:
<223> OTHER INFORMATION: Humanized light chain

<400> SEQUENCE: 36
atggagaccg acaccctgct gctctgggtg ctgctgctct gggtgcccgg ctccaccgga      60
gacgtcgtga tgacccagtc ccctctgtcc ctgcctgtga cctgggaca gcctgcctcc     120 atctcctcag atcctcccag tccctcgtga actccaacgg caacaccttc ctgcagtggt     180
atcagcagcg gcctggccag agcccagac tgctgatcta caaggtgtcc ctgcggttct     240
ccggcgtgcc cgacgatttt ccggctctgg ctctggcacc gacttcaccc tgaagatctc     300
ccgggtggaa gccgaggacg tgggcgtgta ctactgctcc cagagcaccc acgtgccccc     360
tacatttggc ggaggcacca gtggaaaatc aagcggaccg tggccgcccc cagcgtgttc     420
atcttccctc ccagcgacga gcagctgaag tctggcaccg ccagcgtggt gtgcctgctg     480
aacaacttct accccgcga ggccaagggc agtggaaggt ggacaacgcc ctgcagagcg     540
gcaacagcca ggagagcgtg accgagcagg actccaagga cagcacctac agcctgagca     600
gcaccctgac cctgagcaag gccgactacg agaagacaag gtgtacgcct gcgaggtgac     660
ccaccaggga ctgtctagcc ccgtgaccaa gagcttcaac cggggcgagt gctaa          715

<210> SEQ ID NO 37
<211> LENGTH: 238
<212> TYPE: PRT
<213> ORGANISM: Artificial Sequence
<220> FEATURE:
<223> OTHER INFORMATION: Humanized light chain

<400> SEQUENCE: 37

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Arg Gln Ser
        35                  40                  45

Leu Val Asn Ser Asn Gly Asn Thr Phe Leu Gln Trp Tyr Gln Gln Arg
    50                  55                  60

Pro Gly Gln Ser Pro Arg Leu Leu Ile Tyr Lys Val Ser Leu Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gly Gly Thr Val

```
            115                 120                 125
Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 38
<211> LENGTH: 715
<212> TYPE: DNA
<213> ORGANISM: Artificial Sequence
<220> FEATURE:
<223> OTHER INFORMATION: Humanized light chain

<400> SEQUENCE: 38

```
atggagaccg acaccctgct gctctgggtg ctgctgctct gggtgcccgg ctccaccgga    60
gacgtcgtga tgacccagtc ccctctgtcc ctgcctgtga ccctgggaca gcctgcctcc   120
atctcctcag atccaggcag tccctcgtga actccaacgg caacaccttc ctgcagtggt   180
atcagcagcg gctggccag agccccagac tgctgatcta caaggtgtcc ctgcggttct   240
ccggcgtgcc cgacgatttt ccggctctgg ctctggcacc gacttcaccc tgaagatctc   300
ccgggtggaa gccgaggacg tgggcgtgta ctactgctcc cagagcaccc acgtgccccc   360
tacatttggc ggaggcacca gtggaaatc aagcggaccg tggccgcccc cagcgtgttc   420
atcttccctc ccagcgacga gcagctgaag tctggcaccg ccagcgtggt gtgcctgctg   480
aacaacttct accccgcga ggccaagggc agtggaaggt ggacaacgcc ctgcagagcg   540
gcaacagcca ggagagcgtg accgagcagg actccaagga cagcacctac agcctgagca   600
gcaccctgac cctgagcaag gccgactacg agaagcacaag gtgtacgcct gcgaggtgac   660
ccaccaggga ctgtctagcc ccgtgaccaa gagcttcaac cggggcgagt gctaa        715
```

<210> SEQ ID NO 39
<211> LENGTH: 238
<212> TYPE: PRT
<213> ORGANISM: Artificial Sequence
<220> FEATURE:
<223> OTHER INFORMATION: Humanized light chain

<400> SEQUENCE: 39

```
Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Ser Pro
            20                  25                  30

Val Thr Leu Gly Gln Pro Ala Ser Ile Ser Cys Arg Ser Ser Gln Ser
        35                  40                  45

Leu Val Asn Ser Asn Gly Asn Thr Phe Leu Gln Trp Tyr His Gln Arg
    50                  55                  60
```

```
Pro Gly Gln Pro Pro Arg Leu Leu Ile Tyr Lys Val Ser Leu Arg Phe
 65                  70                  75                  80

Ser Gly Val Pro Asp Arg Phe Ser Gly Ser Gly Ala Gly Lys Asp Phe
                 85                  90                  95

Thr Leu Lys Ile Ser Arg Val Glu Ala Glu Asp Val Gly Val Tyr Tyr
            100                 105                 110

Cys Ser Gln Ser Thr His Val Pro Pro Thr Phe Gly Gln Gly Thr Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 40
<211> LENGTH: 715
<212> TYPE: DNA
<213> ORGANISM: Artificial Sequence
<220> FEATURE:
<223> OTHER INFORMATION: Humanized light chain

<400> SEQUENCE: 40
atggagaccg acaccctgct gctctgggtg ctgctgctct gggtgcccgg ctccaccgga      60
gacgtcgtga tgacccagtc ccctctgtcc agtcctgtga ccctgggaca gcctgcctcc     120
atctcctcag atcctcccag tccctcgtga actccaacgg caacaccttc ctgcagtggt     180
atcaccagcg gcctggccag cctcccagac tgctgatcta caaggtgtcc ctgcggttct     240
ccggcgtgcc cgacgatttt ccggctctgg cgctggcaag gacttcaccc tgaagatctc     300
ccgggtggaa gccgaggacg tgggcgtgta ctactgctcc cagagcaccc acgtgccccc     360
tacatttggc cagggcacca actggaaatc aagcggaccg tggccgcccc cagcgtgttc     420
atcttccctc ccagcgacga gcagctgaag tctggcaccg ccagcgtggt gtgcctgctg     480
aacaacttct accccgcga ggccaagggc agtggaaggt ggacaacgcc ctgcagagcg     540
gcaacagcca ggagagcgtg accgagcagg actccaagga cagcacctac agcctgagca     600
gcaccctgac cctgagcaag gccgactacg agaagacaag gtgtacgcct gcgaggtgac     660
ccaccaggga ctgtctagcc ccgtgaccaa gagcttcaac cggggcgagt gctaa         715

<210> SEQ ID NO 41
<211> LENGTH: 5
<212> TYPE: PRT
<213> ORGANISM: Mus musculus

<400> SEQUENCE: 41

Thr Tyr Trp Met His
1               5
```

```
<210> SEQ ID NO 42
<211> LENGTH: 17
<212> TYPE: PRT
<213> ORGANISM: Mus musculus

<400> SEQUENCE: 42

Glu Ile Ser Pro Thr Asn Gly Arg Ala Tyr Tyr Asn Ala Arg Phe Lys
1               5                   10                  15

Ser

<210> SEQ ID NO 43
<211> LENGTH: 9
<212> TYPE: PRT
<213> ORGANISM: Mus musculus

<400> SEQUENCE: 43

Ala Tyr Gly Asn Tyr Glu Phe Ala Tyr
1               5

<210> SEQ ID NO 44
<211> LENGTH: 16
<212> TYPE: PRT
<213> ORGANISM: Mus musculus

<400> SEQUENCE: 44

Arg Ser Arg Gln Ser Leu Val Asn Ser Asn Gly Asn Thr Phe Leu Gln
1               5                   10                  15

<210> SEQ ID NO 45
<211> LENGTH: 7
<212> TYPE: PRT
<213> ORGANISM: Mus musculus

<400> SEQUENCE: 45

Lys Val Ser Leu Arg Phe Ser
1               5

<210> SEQ ID NO 46
<211> LENGTH: 9
<212> TYPE: PRT
<213> ORGANISM: Mus musculus

<400> SEQUENCE: 46

Ser Gln Ser Thr His Val Pro Pro Thr
1               5
```